United States Patent
Lewis et al.

(10) Patent No.: US 9,289,430 B2
(45) Date of Patent: *Mar. 22, 2016

(54) COMPOUNDS AND METHODS FOR INHIBITING PHOSPHATE TRANSPORT

(71) Applicant: Ardelyx, Inc., Fremont, CA (US)

(72) Inventors: Jason G. Lewis, Castro Valley, CA (US); Jeffrey W. Jacobs, San Mateo, CA (US); Nicholas Reich, Berkeley, CA (US); Michael R. Leadbetter, San Leandro, CA (US); Noah Bell, Berkeley, CA (US); Han-Ting Chang, Livermore, CA (US); Tao Chen, Palo Alto, CA (US); Marc Navre, Belmont, CA (US); Dominique Charmot, Campbell, CA (US); Christopher Carreras, Belmont, CA (US); Eric Labonte, Redwood City, CA (US)

(73) Assignee: Ardelyx, Inc., Fremont, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,028

(22) Filed: Jul. 21, 2014

(65) Prior Publication Data

US 2015/0164904 A1     Jun. 18, 2015

Related U.S. Application Data

(63) Continuation of application No. 13/734,562, filed on Jan. 4, 2013, now Pat. No. 8,815,910, which is a continuation of application No. PCT/US2011/043261, filed on Jul. 7, 2011.

(60) Provisional application No. 61/362,121, filed on Jul. 7, 2010.

(51) Int. Cl.
| | |
|---|---|
| *A61K 31/4439* | (2006.01) |
| *A61K 31/454* | (2006.01) |
| *C07D 401/12* | (2006.01) |
| *A61K 31/5377* | (2006.01) |
| *A61K 31/4965* | (2006.01) |
| *A61K 31/505* | (2006.01) |
| *A61K 45/06* | (2006.01) |
| *C07D 211/68* | (2006.01) |
| *C07D 231/40* | (2006.01) |
| *C07D 233/88* | (2006.01) |
| *C07D 255/02* | (2006.01) |
| *C07D 277/46* | (2006.01) |
| *C07D 285/135* | (2006.01) |
| *A61K 31/415* | (2006.01) |
| *A61K 31/4545* | (2006.01) |
| *A61K 31/59* | (2006.01) |
| *C07D 249/14* | (2006.01) |

(52) U.S. Cl.
CPC ........... *A61K 31/5377* (2013.01); *A61K 31/415* (2013.01); *A61K 31/454* (2013.01); *A61K 31/4545* (2013.01); *A61K 31/4965* (2013.01); *A61K 31/505* (2013.01); *A61K 31/59* (2013.01); *A61K 45/06* (2013.01); *C07D 211/68* (2013.01); *C07D 231/40* (2013.01); *C07D 233/88* (2013.01); *C07D 249/14* (2013.01); *C07D 255/02* (2013.01); *C07D 277/46* (2013.01); *C07D 285/135* (2013.01); *C07D 401/12* (2013.01)

(58) Field of Classification Search
None
See application file for complete search history.

(56) References Cited

U.S. PATENT DOCUMENTS

| | | | |
|---|---|---|---|
| 6,300,363 | B1 | 10/2001 | Steven et al. |
| 6,608,070 | B1 | 8/2003 | Nakao et al. |

(Continued)

FOREIGN PATENT DOCUMENTS

| | | |
|---|---|---|
| EP | 1614676 A1 | 3/2001 |
| EP | 1273575 A1 | 1/2006 |

(Continued)

OTHER PUBLICATIONS

Chou, Y-L et al., "Structure-Activity Relationships of Substituted Benzothiophene-anthranilamide Factor Xa Inhibitors", Bioorganic & Medicinal Chemistry Letters, Pergamon. GB, vol. 13, Jan. 1, 2003, pp. 507-511.

(Continued)

*Primary Examiner* — Michael Barker
(74) *Attorney, Agent, or Firm* — Cooley LLP

(57) ABSTRACT

Compounds having activity as phosphate transport inhibitors, more specifically, inhibitors of intestinal apical membrane Na/phosphate co-transport, are disclosed. The compounds have the following structure (I):

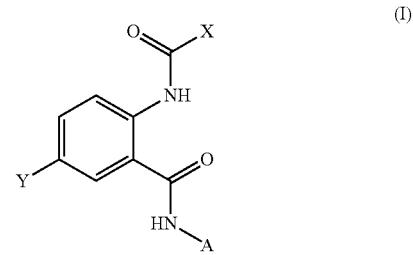

including stereoisomers, pharmaceutically acceptable salts and prodrugs thereof, wherein X, Y and A are as defined herein. Methods associated with preparation and use of such compounds, as well as pharmaceutical compositions comprising such compounds, are also disclosed.

35 Claims, No Drawings

(56) References Cited

U.S. PATENT DOCUMENTS

| | | | |
|---|---|---|---|
| 8,809,339 | B2 | 8/2014 | Lewis et al. |
| 8,815,908 | B2 | 8/2014 | Lewis et al. |
| 8,815,910 | B2 | 8/2014 | Lewis et al. |
| 2002/0133036 | A1 | 9/2002 | Peerce |
| 2003/0195193 | A1 | 10/2003 | Hirayama et al. |
| 2003/0216449 | A1 | 11/2003 | Weinstock et al. |
| 2004/0019113 | A1 | 1/2004 | Josefiak et al. |
| 2005/0261346 | A1 | 11/2005 | Zhu et al. |
| 2008/0026037 | A1 | 1/2008 | Christensen et al. |
| 2009/0227566 | A1 | 9/2009 | Argade et al. |
| 2013/0336918 | A1 | 12/2013 | Lewis et al. |
| 2013/0336919 | A1 | 12/2013 | Lewis et al. |
| 2013/0336920 | A1 | 12/2013 | Lewis et al. |
| 2013/0336921 | A1 | 12/2013 | Lewis et al. |
| 2014/0023611 | A1 | 1/2014 | Lewis et al. |

FOREIGN PATENT DOCUMENTS

| | | | |
|---|---|---|---|
| WO | 01/05398 | A1 | 1/2001 |
| WO | 01/21160 | A2 | 3/2001 |
| WO | 03/057225 | A2 | 7/2003 |
| WO | 2012/006473 | A1 | 1/2012 |
| WO | 2012/006474 | A2 | 1/2012 |
| WO | 2012/006475 | A1 | 1/2012 |
| WO | 2012/006477 | A1 | 1/2012 |
| WO | 2012/054110 | A2 | 4/2012 |
| WO | 2014/029983 | A1 | 2/2014 |
| WO | 2014/029984 | A1 | 2/2014 |

OTHER PUBLICATIONS

Ertl et al., "Fast Calculation of Molecular Polar Surface Area as a Sum of Fragment-Based Contributions and Its Application to the Prediction of Drug Transport Properties", J. Med. Chem. (2000) 43:3714-3717.
Eto et al., "Nicotinamide prevents the development of hyperphosphataemia by suppressing intestinal sodium-dependent phosphate transporter in rats with adenine-induced renal failure",Nephrol Dial Transplant (2005) 20:1378-1384.
Lipinski, Drug-like Properties and the Causes of Poor Solubility and Poor Permeability, J. Pharm. & Toxicol. Methods, (2000) 44:235-249.
Lipinski et al., Experimental and Computational Approaches to Estimate Solubility and Permeability in Drug Discovery and Development Settings, Adv. Drug Delivery Reviews, (2001) 46:3-26.
Stec, Markian M., et al., Bioorganic & Medical Chemistry Letters, "Substituted aryl pyrimidines as potent and soluble TRPV1 antagonists", (2008) 18:5118-5122.
STN/CAPLUS Accession No. 2012:1449104, citing Cooper, M., "An investigation of intramolecular nucleophilic substitution in indole," Dissertation, Department of Chemistry, University of Manchester (1978).
Zakeri-Milani et al., "The relation between molecular properties of drugs and their transport across the intestinal membrane", DARU vol. 14, No. 4, 2006.
International Search Report for PCT/US2011/043267 mailed Apr. 5, 2012, 3 pages.
Written Opinion of the International Searching Authority for PCT/US2011/043267 mailed Apr. 5, 2012, 5 pages.
International Preliminary Report on Patentability for PCT/US2011/043267 mailed Jan. 8, 2013, 6 pages.
Supplemental European Search Report in EU Application No. 11834773.1 mailed Nov. 28, 2013, 4 pages.
International Search Report for PCT/US2011/043261 mailed Nov. 21, 2011, 3 pages.
Written Opinion of the International Searching Authority for PCT/US2011/043261 mailed Nov. 21, 2011, 5 pages.
International Preliminary Report on Patentability for PCT/US2011/043261 mailed Jan. 8, 2013, 6 pages.
Supplementary European Search Report in EU Application No. 11804369.4 dated Nov. 15, 2013.
International Search Report for PCT/US2011/043262 mailed Nov. 18, 2011, 3 pages.
Written Opinion of the International Searching Authority for PCT/US2011/043262 mailed Nov. 18, 2011, 5 pages.
International Preliminary Report on Patentability for PCT/US2011/043262 dated Jun. 25, 2013, 6 pages.
International Search Report for PCT/US2011/043266 mailed Nov. 21, 2011, 3 pages.
Written Opinion of the International Searching Authority for PCT/US2011/043266 mailed Nov. 21, 2011, 4 pages.
International Preliminary Report on Patentability for PCT/US2011/043266 dated Jan. 8, 2013, 5 pages.
Supplementary European Search Report in EU Application No. 11804373.6 dated Dec. 5, 2013, 6 pages.
International Search Report for PCT/US2011/043263 mailed Nov. 21, 2011, 4 pages.
Written Opinion of the International Searching Authority for PCT/US2011/043263 mailed Nov. 21, 2011, 6 pages.
International Preliminary Report on Patentability for PCT/US2011/043263 dated Jan. 8, 2013, 7 pages.
Supplementary European Search Report in EU Application No. 11804371.0 dated Apr. 10, 2014, 8 pages.
Communication pursuant to Rules 70(2) and 70a(2) EPC in EU Application No. 11804371.0 dated Apr. 29, 2014, 1 page.
Office Action in U.S. Appl. No. 13/734,547 issued Sep. 30, 2013, 5 pages.
Notice of Allowance in U.S. Appl. No. 13/734,547 mailed Apr. 9, 2014, 6 pages.
2nd Notice of Allowance in U.S. Appl. No. 13/734,547, mailed Aug. 8, 2014, 6 pages.
Office Action in U.S. Appl. No. 13/734,562 issued Oct. 2, 2013, 6 pages.
Notice of Allowance in U.S. Appl. No. 13/734,562, dated Apr. 22, 2014, 7 pages.
Office Action in U.S. Appl. No. 13/734,551 issued Sep. 30, 2013.
Notice of Allowance in U.S. Appl. No. 13/734,551 dated Apr. 11, 2014.
Office Action in U.S. Appl. No. 13/734,701 issued Oct. 1, 2013.
Notice of Allowance in U.S. Appl. No. 13/734,701, dated Apr. 22, 2014.

COMPOUNDS AND METHODS FOR INHIBITING PHOSPHATE TRANSPORT

CROSS-REFERENCE TO RELATED APPLICATIONS

This application is a continuation of U.S. patent application Ser. No. 13/734,562, filed Jan. 4, 2013, now pending, which is a continuation of International PCT Patent Application No. PCT/US2011/043261, filed Jul. 7, 2011, which claims the benefit under 35 U.S.C. §119(e) of U.S. Provisional Patent Application No. 61/362,121 filed Jul. 7, 2010. The foregoing applications are incorporated herein by reference in their entireties.

BACKGROUND

1. Field

The present invention is directed to novel phosphate transport inhibitors, more specifically, inhibitors of intestinal apical membrane Na/phosphate co-transport, and methods for their preparation and use as therapeutic or prophylactic agents.

2. Description of the Related Art

Patients with inadequate renal function, hypoparathyroidism, or certain other medical conditions (such as hereditary hyperphosphatemia, Albright hereditary osteodystrophy, amyloidosis, etc.) often have hyperphosphatemia, or elevated serum phosphate levels (wherein the level, for example, is more than about 6 mg/dL). Hyperphosphatemia, especially if present over extended periods of time, leads to severe abnormalities in calcium and phosphorus metabolism, often manifested by secondary hyperparathyroidism, bone disease and ectopic calcification in the cardiovascular system, joints, lungs, eyes and other soft tissues. Higher serum phosphorus levels are strongly associated with the progression of renal failure, cardiovascular calcification and mortality in end-stage renal disease (ESRD) patients. High-normal serum phosphorus levels have been associated with cardiovascular events and mortality among individuals who have chronic kidney disease (CKD) and among those who have normal kidney function (see, e.g., Joy, M. S., P. C. Karagiannis and F. W. Peyerl, Outcomes of Secondary Hyperparathyroidism in Chronic Kidney Disease and the Direct Costs of Treatment, J. Manag. Care Pharm., 13(5):397-411 (2007)) The progression of kidney disease can be slowed by reducing phosphate retention. Thus, for renal failure patients who are hyperphosphatemic and for chronic kidney disease patients who have serum phosphate levels within the normal range or only slightly elevated, therapy to reduce phosphate retention is beneficial.

For patients who experience hyperphosphatemia, calcium salts have been widely used to bind intestinal phosphate and prevent its absorption. Different types of calcium salts, including calcium carbonate, acetate, citrate, alginate, and ketoacid salts have been utilized for phosphate binding. A problem with all of these therapeutics is the hypercalcemia, which often results from absorption of high amounts of ingested calcium. Hypercalcemia causes serious side effects such as cardiac arrhythmias, renal failure, and skin and vascular calcification. Frequent monitoring of serum calcium levels is required during therapy with calcium-based phosphate binders. Other calcium and aluminum-free phosphate binders, such as sevelamer, a crosslinked polyamine polymer, have drawbacks that include the amount and frequency of dosing required to be therapeutically active. The relatively modest phosphate binding capacity of those drugs in vivo obliges patients to escalate the dose (up to 7 grs per day or more). Such quantities have been shown to produce gastrointestinal discomfort, such as dyspepsia, abdominal pain and, in some extreme cases, bowel perforation.

An alternative approach to the prevention of phosphate absorption from the intestine in patients with elevated phosphate serum levels is through inhibition of the intestinal transport system which mediates phosphate uptake in the intestine. It is understood that phosphate absorption in the upper intestine is mediated at least in part by a carrier-mediated mechanism which couples the absorption of phosphate to that of sodium. Inhibition of intestinal phosphate transport will reduce body phosphorus overload. In patients with advanced kidney disease (e.g. stage 4 and 5), the body phosphorus overload manifests itself by serum phosphate concentration above normal levels, i.e. hyperphosphatemia. Hyperphosphatemia is directly related to mortality and morbidity. Inhibition of intestinal phosphate transport will reduce serum phosphate concentration and therefore improve outcome in those patients. In chronic kidney disease patients stage 2 and 3, the body phosphorus overload does not necessarily lead to hyperphosphatemia, i.e. patients remain normophosphatemic, but there is a need to reduce body phosphorus overload even at those early stages to avoid associated bone and vascular disorders, and ultimately improve mortality rate. Similarly, inhibition of intestinal phosphate transport would be particularly advantageous in patients that have a disease that is treatable by inhibiting the uptake of phosphate from the intestines. Inhibition of phosphate absorption from the glomerular filtrate within the kidneys would also be advantageous for treating chronic renal failure. Furthermore, inhibition of phosphate transport may slow the progression of renal failure and reduce risk of cardiovascular events.

While progress has been made in this field, there remains a need in the art for novel phosphate transport inhibitors. The present invention fulfills this need and provides further related advantages.

BRIEF SUMMARY

In brief, the present invention is directed to compounds having activity as phosphate transport inhibitors, more specifically, inhibitors of intestinal apical membrane Na/phosphate co-transport, including stereoisomers, pharmaceutically acceptable salts and prodrugs thereof, and the use of such compounds to inhibit sodium-mediated phosphate uptake and to thereby treat any of a variety of conditions or diseases in which modulation of sodium-mediated phosphate uptake provides a therapeutic benefit.

In one embodiment, compounds having the following structure (I) are provided:

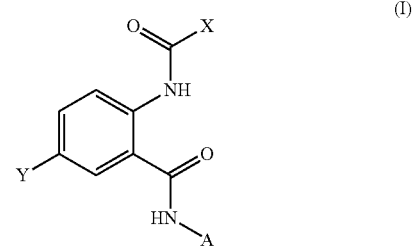

or a stereoisomer, prodrug or pharmaceutically acceptable salt thereof, wherein:
A is:

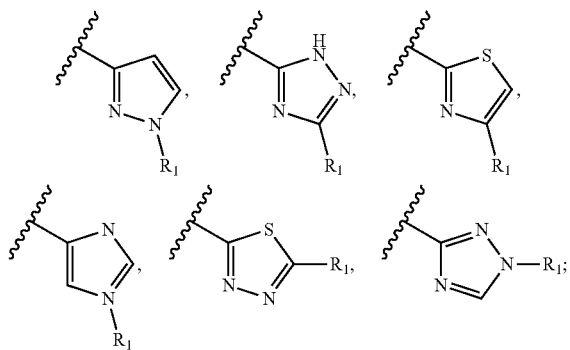

X is substituted aryl or substituted heteroaryl;

Y is halogen, optionally substituted alkylamino, optionally substituted alkoxy, optionally substituted thioalkyl, optionally substituted cycloalkyl, optionally substituted heterocyclyl, optionally substituted aryl, —O(optionally substituted cycloalkyl), —O(optionally substituted heterocyclyl) or —O(optionally substituted aryl); and $R_1$ is optionally substituted aryl or optionally substituted heteroaryl.

In another embodiment, a pharmaceutical composition is provided comprising a compound having structure (I), or a stereoisomer, pharmaceutically acceptable salt or prodrug thereof, and a pharmaceutically acceptable carrier, diluent or excipient. In further embodiments, the pharmaceutical composition further comprises one or more additional biologically active agents. In more specific embodiments, the additional biologically active agent is selected from vitamin $D_2$ (ergocalciferol), vitamin $D_3$ (cholecalciferol), active vitamin D (calcitriol) and active vitamin D analogs (e.g. doxercalciferol, paricalcitol). In other more specific embodiments, the additional biologically active agent is a phosphate binder, and the compound does not interfere with the phosphate binder. For example, in certain embodiments, the phosphate binder is selected from the group consisting of Renvela, Renagel, Fosrenol, calcium carbonate, calcium acetate (e.g. Phoslo), MCI-196, Zerenex™, Fermagate, APS1585, SBR-759 and PA-21. In other further embodiments, the compound is substantially active as an inhibitor of Na/phosphate co-transport and the Na/phosphate co-transport is mediated by NaPi2b.

In another embodiment, a method of inhibiting phosphate transport in a mammal is provided, comprising administering to the mammal an effective amount of a compound having structure (I), or a stereoisomer, pharmaceutically acceptable salt or prodrug thereof, or a pharmaceutical composition comprising such compound. In further embodiments, the method inhibits sodium-mediated phosphate uptake. In other further embodiments, the method is selected from the group consisting of: (a) a method for treating hyperphosphatemia; (b) a method for treating a renal disease; (c) a method for delaying time to dialysis; (d) a method for attenuating intima localized vascular calcification; (e) a method for reducing the hyperphosphatemic effect of active vitamin D; (f) a method for reducing FGF23 levels; (g) a method for attenuating hyperparathyroidism; (h) a method for improving endothelial dysfunction induced by postprandial serum phosphate; (i) a method for reducing urinary phosphorous; (j) a method for normalizing serum phosphorus levels; (k) a method for treating proteinura; and (l) a method for reducing serum PTH and phosphate concentrations or levels. In certain embodiments, the renal disease is chronic kidney disease or end stage renal disease.

In another embodiment, a method of treating hyperphosphatemia in a mammal in need thereof is provided, comprising administering to the mammal an effective amount of a compound having structure (I), or a stereoisomer, pharmaceutically acceptable salt or prodrug thereof, or a pharmaceutical composition comprising such compound.

These and other aspects of the invention will be apparent upon reference to the following detailed description.

DETAILED DESCRIPTION

In the following description, certain specific details are set forth in order to provide a thorough understanding of various embodiments of the invention. However, one skilled in the art will understand that the invention may be practiced without these details.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

"Amino" refers to the —$NH_2$ radical.
"Cyano" refers to the —CN radical.
"Hydroxy" or "hydroxyl" refers to the —OH radical.
"Imino" refers to the =NH substituent.
"Nitro" refers to the —$NO_2$ radical.
"Oxo" refers to the =O substituent.
"Thioxo" refers to the =S substituent.

"Alkyl" refers to a straight or branched hydrocarbon chain radical consisting solely of carbon and hydrogen atoms, which is saturated or unsaturated (i.e., contains one or more double and/or triple bonds), having from one to twelve carbon atoms ($C_{1-12}$ alkyl), preferably one to eight carbon atoms ($C_1$-$C_8$ alkyl) or one to six carbon atoms ($C_1$-$C_6$ alkyl), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, ethenyl, prop-1-enyl, but-1-enyl, pent-1-enyl, penta-1,4-dienyl, ethynyl, propynyl, butynyl, pentynyl, hexynyl, and the like. Unless stated otherwise specifically in the specification, an alkyl group may be optionally substituted.

"Alkylene" or "alkylene chain" refers to a straight or branched divalent hydrocarbon chain linking the rest of the molecule to a radical group, consisting solely of carbon and hydrogen, which is saturated or unsaturated (i.e., contains one or more double and/or triple bonds), and having from one to twelve carbon atoms, e.g., methylene, ethylene, propylene, n-butylene, ethenylene, propenylene, n-butenylene, propynylene, n-butynylene, and the like. The alkylene chain is attached to the rest of the molecule through a single or double bond and to the radical group through a single or double bond. The points of attachment of the alkylene chain to the rest of the molecule and to the radical group can be through one carbon or any two carbons within the chain. Unless stated otherwise specifically in the specification, an alkylene chain may be optionally substituted.

"Alkoxy" refers to a radical of the formula —OR$_a$ where R$_a$ is an alkyl radical as defined above containing one to twelve carbon atoms. Unless stated otherwise specifically in the specification, an alkoxy group may be optionally substituted.

"Alkylamino" refers to a radical of the formula —NHR$_a$ or —NR$_a$R$_a$ where each R$_a$ is, independently, an alkyl radical as defined above containing one to twelve carbon atoms. Unless stated otherwise specifically in the specification, an alkylamino group may be optionally substituted.

"Thioalkyl" refers to a radical of the formula —SR$_a$ where R$_a$ is an alkyl radical as defined above containing one to twelve carbon atoms. Unless stated otherwise specifically in the specification, a thioalkyl group may be optionally substituted.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may include fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene. Unless stated otherwise specifically in the specification, the term "aryl" or the prefix "ar-" (such as in "aralkyl") is meant to include aryl radicals that are optionally substituted.

"Aralkyl" refers to a radical of the formula —R$_b$—R$_c$ where R$_b$ is an alkylene chain as defined above and R$_c$ is one or more aryl radicals as defined above, for example, benzyl, diphenylmethyl and the like. Unless stated otherwise specifically in the specification, an aralkyl group may be optionally substituted.

"Cycloalkyl" or "carbocyclic ring" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, 7,7-dimethyl-bicyclo[2.2.1]heptanyl, and the like. Unless otherwise stated specifically in the specification, a cycloalkyl group may be optionally substituted.

"Cycloalkylalkyl" refers to a radical of the formula —R$_b$R$_d$ where R$_d$ is an alkylene chain as defined above and R$_g$ is a cycloalkyl radical as defined above. Unless stated otherwise specifically in the specification, a cycloalkylalkyl group may be optionally substituted.

"Fused" refers to any ring structure described herein which is fused to an existing ring structure in the compounds of the invention. When the fused ring is a heterocyclyl ring or a heteroaryl ring, any carbon atom on the existing ring structure which becomes part of the fused heterocyclyl ring or the fused heteroaryl ring may be replaced with a nitrogen atom.

"Halo" or "halogen" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1,2-difluoroethyl, 3-bromo-2-fluoropropyl, 1,2-dibromoethyl, and the like. Unless stated otherwise specifically in the specification, a haloalkyl group may be optionally substituted.

"Heterocyclyl" or "heterocyclic ring" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, Unless stated otherwise specifically in the specification, a heterocyclyl group may be optionally substituted.

"N-heterocyclyl" refers to a heterocyclyl radical as defined above containing at least one nitrogen and where the point of attachment of the heterocyclyl radical to the rest of the molecule is through a nitrogen atom in the heterocyclyl radical. Unless stated otherwise specifically in the specification, a N-heterocyclyl group may be optionally substituted.

"Heterocyclylalkyl" refers to a radical of the formula —R$_b$R$_e$ where R$_b$ is an alkylene chain as defined above and R$_e$ is a heterocyclyl radical as defined above, and if the heterocyclyl is a nitrogen-containing heterocyclyl, the heterocyclyl may be attached to the alkyl radical at the nitrogen atom. Unless stated otherwise specifically in the specification, a heterocyclylalkyl group may be optionally substituted.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzothiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl (i.e., thienyl). Unless stated otherwise specifically in the specification, a heteroaryl group may be optionally substituted.

"N-heteroaryl" refers to a heteroaryl radical as defined above containing at least one nitrogen and where the point of attachment of the heteroaryl radical to the rest of the molecule is through a nitrogen atom in the heteroaryl radical. Unless stated otherwise specifically in the specification, an N-heteroaryl group may be optionally substituted.

"Heteroarylalkyl" refers to a radical of the formula —$R_bR_f$— where $R_b$ is an alkylene chain as defined above and $R_f$ is a heteroaryl radical as defined above. Unless stated otherwise specifically in the specification, a heteroarylalkyl group may be optionally substituted.

The term "substituted" used herein means any of the above groups (i.e., alkyl, alkylene, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl) wherein at least one hydrogen atom is replaced by a bond to a non-hydrogen atoms such as, but not limited to: a halogen atom such as F, Cl, Br, and I; an oxygen atom in groups such as hydroxyl groups, alkoxy groups, and ester groups; a sulfur atom in groups such as thiol groups, thioalkyl groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as trialkylsilyl groups, dialkylarylsilyl groups, alkyldiarylsilyl groups, and triarylsilyl groups; and other heteroatoms in various other groups. "Substituted" also means any of the above groups in which one or more hydrogen atoms are replaced by a higher-order bond (e.g., a double- or triple-bond) to a heteroatom such as oxygen in oxo, carbonyl, carboxyl, and ester groups; and nitrogen in groups such as imines, oximes, hydrazones, and nitriles. For example, "substituted" includes any of the above groups in which one or more hydrogen atoms are replaced with —$NR_gR_h$, —$NR_gC(=O)R_h$, —$NR_gC(=O)NR_gR_h$, —$NR_gC(=O)OR_h$, —$NR_gSO_2R_h$, —$OC(=O)NR_gR_h$, —$OR_g$, —$SR_g$, —$SOR_g$, —$SO_2R_g$, —$OSO_2R_g$, —$SO_2OR_g$, =$NSO_2R_g$, and —$SO_2NR_gR_h$. "Substituted" also means any of the above groups in which one or more hydrogen atoms are replaced with —$C(=O)R_g$, —$C(=O)OR_g$, —$C(=O)NR_gR_h$, —$CH_2SO_2R_g$, —$CH_2SO_2NR_gR_h$, —$(CH_2CH_2O)_{2-10}R_g$. In the foregoing, $R_g$ and $R_h$ are the same or different and independently hydrogen, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl. "Substituted" further means any of the above groups in which one or more hydrogen atoms are replaced by a bond to an amino, cyano, hydroxyl, imino, nitro, oxo, thioxo, halo, alkyl, alkoxy, alkylamino, thioalkyl, aryl, aralkyl, cycloalkyl, cycloalkylalkyl, haloalkyl, heterocyclyl, N-heterocyclyl, heterocyclylalkyl, heteroaryl, N-heteroaryl and/or heteroarylalkyl group. The above non-hydrogen groups are generally referred to herein as "substituents". In addition, each of the foregoing substituents may also be optionally substituted with one or more of the above substituents.

"Prodrug" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammalian organism (see, Bundgard, H., Design of Prodrugs (1985), pp. 7-9, 21-24 (Elsevier, Amsterdam)). A discussion of prodrugs is provided in Higuchi, T., et al., A.C.S. Symposium Series, Vol. 14, and in Bioreversible Carriers in Drug Design, Ed. Edward B. Roche, American Pharmaceutical Association and Pergamon Press, 1987.

The term "prodrug" is also meant to include any covalently bonded carriers, which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol or amide derivatives of amine functional groups in the compounds of the invention and the like.

The invention disclosed herein is also meant to encompass the in vivo metabolic products of the disclosed compounds. Such products may result from, for example, the oxidation, reduction, hydrolysis, amidation, esterification, and the like of the administered compound, primarily due to enzymatic processes. Accordingly, the invention includes compounds produced by a process comprising administering a compound of this invention to a mammal for a period of time sufficient to yield a metabolic product thereof. Such products are typically identified by administering a radiolabelled compound of the invention in a detectable dose to an animal, such as rat, mouse, guinea pig, monkey, or to human, allowing sufficient time for metabolism to occur, and isolating its conversion products from the urine, blood or other biological samples.

"Stable compound" and "stable structure" are meant to indicate a compound that is sufficiently robust to survive isolation to a useful degree of purity from a reaction mixture, and formulation into an efficacious therapeutic agent.

"Mammal" includes humans and both domestic animals such as laboratory animals and household pets (e.g., cats, dogs, swine, cattle, sheep, goats, horses, rabbits), and non-domestic animals such as wildlife and the like.

"Optional" or "optionally" means that the subsequently described event or circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

Often crystallizations produce a solvate of the compound of the invention. As used herein, the term "solvate" refers to an aggregate that comprises one or more molecules of a compound of the invention with one or more molecules of solvent. The solvent may be water, in which case the solvate may be a hydrate. Alternatively, the solvent may be an organic solvent. Thus, the compounds of the present invention may exist as a hydrate, including a monohydrate, dihydrate, hemihydrate, sesquihydrate, trihydrate, tetrahydrate and the like, as well as the corresponding solvated forms. The compound of the invention may be true solvates, while in other cases, the compound of the invention may merely retain adventitious water or be a mixture of water plus some adventitious solvent.

A "pharmaceutical composition" refers to a formulation of a compound of the invention and a medium generally accepted in the art for the delivery of the biologically active compound to mammals, e.g., humans. Such a medium includes all pharmaceutically acceptable carriers, diluents or excipients therefor.

"Effective amount" or "therapeutically effective amount" refers to that amount of a compound of the invention which, when administered to a mammal, preferably a human, is sufficient to inhibit phosphate transport, inhibit sodium-mediated phosphate uptake, reduce serum PTH, calcium, calcitriol, and phosphate concentrations or levels, treat renal disease or treat hyperphosphatemia in the mammal, preferably a human. The amount of a compound of the invention which constitutes a "therapeutically effective amount" will vary depending on the compound, the condition and its severity, the manner of administration, and the age of the mammal to be treated, but can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes:

(i) preventing the disease or condition from occurring in a mammal, in particular, when such mammal is predisposed to the condition but has not yet been diagnosed as having it;

(ii) inhibiting the disease or condition, i.e., arresting its development;

(iii) relieving the disease or condition, i.e., causing regression of the disease or condition; or (iv) relieving the symptoms resulting from the disease or condition, i.e., relieving pain without addressing the underlying disease or condition. As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as their racemic and optically pure forms. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centres of geometric asymmetry, and unless specified otherwise, it is intended that the compounds include both E and Z geometric isomers. Likewise, all tautomeric forms are also intended to be included.

A "stereoisomer" refers to a compound made up of the same atoms bonded by the same bonds but having different three-dimensional structures, which are not interchangeable. The present invention contemplates various stereoisomers and mixtures thereof and includes "enantiomers", which refers to two stereoisomers whose molecules are nonsuperimposeable mirror images of one another.

A "tautomer" refers to a proton shift from one atom of a molecule to another atom of the same molecule. The present invention includes tautomers of any said compounds.

As noted above, in one embodiment of the present invention, compounds having activity as phosphate transport inhibitors, more specifically, inhibitors of intestinal apical membrane Na/phosphate co-transport, are provided, the compounds having the following structure (I):

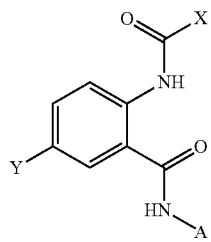

(I)

or a stereoisomer, prodrug or pharmaceutically acceptable salt thereof,
wherein:
A is:

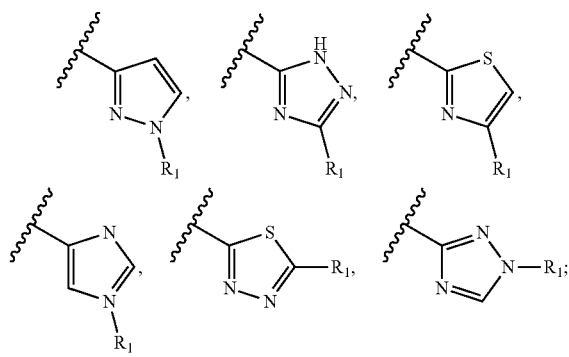

X is substituted aryl or substituted heteroaryl;
Y is halogen, optionally substituted alkylamino, optionally substituted alkoxy, optionally substituted thioalkyl, optionally substituted cycloalkyl, optionally substituted heterocyclyl, optionally substituted aryl, —O(optionally substituted cycloalkyl), —O(optionally substituted heterocyclyl) or —O(optionally substituted aryl); and
$R_1$ is optionally substituted aryl or optionally substituted heteroaryl.

In further embodiments, Y is halogen, such as chloro.
In other further embodiments, Y is alkylamino, such as diethylamino
In other further embodiments, Y is alkoxy.
In other further embodiments, Y is heterocyclyl, such as 1-piperidinyl and the compound has the structure:

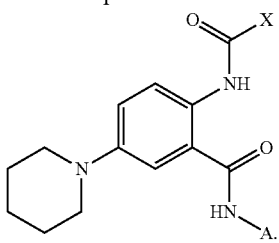

In other further embodiments, Y is —O(cycloalkyl).
In other further embodiments, X is —$ZR_2$. where Z is aryl or heteroaryl and $R_2$ represents a non-hydrogen substituent as defined above, or as more specifically defined below.

In more specific embodiments, Z is aryl, such as phenyl and the compound has the structure:

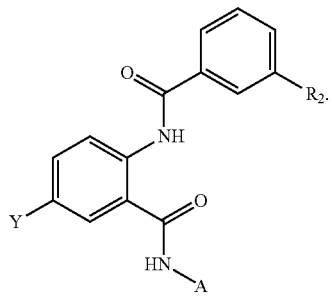

In other more specific embodiments, Z is heteroaryl, such as pyridinyl and the compound has the structure:

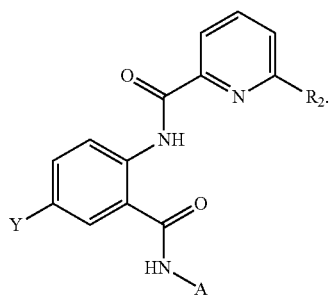

In more specific embodiments of the foregoing, $R_2$ is:
(a) —$CH_2S(O)_{0-2}$(optionally substituted $C_{1-6}$alkyl)C(=O)$NR_6R_3$,
(b) —$CH_2S(O)_{0-2}$(optionally substituted $C_{1-6}$alkyl)$NR_6R_3$,
(c) —$CH_2S(O)_{0-2}$(optionally substituted $C_{1-6}$alkyl)C(=O)$OR_4$,
(d) —$CH_2S(O)_{0-2}$(optionally substituted $C_{1-6}$alkyl)$OR_4$,
(e) —$CH_2S(O)_{0-2}$(optionally substituted $C_{1-6}$alkyl)$R_5$,
(f) —$CH_2S(O)_{0-2}R_5$,
(g) —$CH_2S(O)_{0-2}NR_6R_3$,
(h) —$CH_2S(O)_{0-2}(CH_2CH_2O)_xR_4$,
(i) —$CH_2NR_6(CH_2CH_2O)_xR_4$,
(j) —C(=O)$NR_6$(optionally substituted $C_{1-6}$alkyl)C(=O)$NR_6R_3$,
(k) —C(=O)$NR_6$(optionally substituted $C_{1-6}$alkyl)$NR_6R_3$,
(l) —C(=O)$NR_6$(optionally substituted $C_{1-6}$alkyl)C(=O)$OR_4$,
(m) —C(=O)$NR_6$(optionally substituted $C_{1-6}$alkyl)$OR_4$,
(n) —C(=O)$NR_6$(optionally substituted $C_{1-6}$alkyl)$R_5$, or
(o) —C(=O)$NR_6(CH_2CH_2O)_xR_4$;
wherein,
$R_3$ is hydrogen, hydroxyl, alkoxy, optionally substituted $C_{1-6}$alkyl, optionally substituted aryl, optionally substituted heterocyclyl or optionally substituted heteroaryl;
$R_4$ is hydrogen, optionally substituted $C_{1-6}$alkyl, optionally substituted aryl, optionally substituted heterocyclyl or optionally substituted heteroaryl;
$R_5$ is optionally substituted aryl, optionally substituted heterocyclyl or optionally substituted heteroaryl;

$R_6$ is hydrogen or optionally substituted $C_{1-6}$alkyl; and x is an integer from 2 to 10.

In other further embodiments, A is:

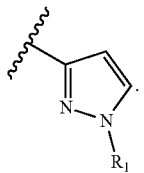

In other further embodiments, A is:

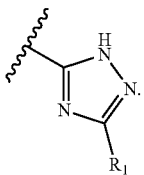

In other further embodiments, A is:

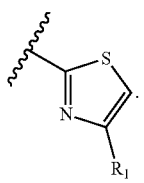

In other further embodiments, A is:

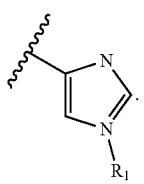

In other further embodiments, A is:

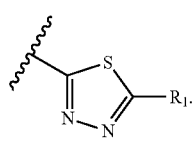

In other further embodiments, A is:

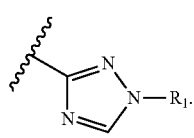

In other further embodiments, $R_1$ is optionally substituted aryl. In more specific embodiments, $R_1$ is phenyl. In other more specific embodiments, $R_1$ is substituted phenyl, such as trifluoromethylphenyl.

It is understood that any embodiment of the compounds of structure (I), as set forth above, and any specific substituent set forth herein for a X, Y, A, $R_1$, $R_2$, $R_3$, $R_4$, $R_5$ or $R_6$ group in the compounds of structure (I), as set forth above, may be independently combined with other embodiments and/or substituents of compounds of structure (I) to form embodiments of the inventions not specifically set forth above. In addition, in the event that a list of substitutents is listed for any particular substituent in a particular embodiment and/or claim, it is understood that each individual substituent may be deleted from the particular embodiment and/or claim and that the remaining list of substituents will be considered to be within the scope of the invention.

In accordance with the present disclosure, it has been discovered that phosphate absorption from the intestine in patients with elevated phosphate serum levels may be limited, and preferably substantially prevented, through inhibition of the intestinal transport system which mediates phosphate uptake in the intestine. This inhibition may be achieved by the administration of certain compounds, and/or pharmaceutical compositions comprising them, which may advantageously be designed such that little, or substantially none, of the compound is absorbed into the blood stream (that is, it is designed to be non-systemic or substantially non-systemic). Such compounds are described as generally abiding by "Ardelyx Rules." In this regard, the compounds have features that give rise to little or substantially no systemic availability. In other words, the compounds are not absorbed into the bloodstream at meaningful levels and therefore have no activity there, but instead have their activity localized substantially within the GI tract.

Therefore, in certain illustrative embodiments as further described herein, the compounds of the invention generally require a combination of structural and/or functional features relating or contributing to their activity in the GI tract and/or their substantial non-systemic bioavailability. Such features may include, for example, one or more of (i) specific tPSA and/or MW values (e.g., at least about 190 Å$^2$ and/or at least about 736 Daltons, respectively), (ii) specific levels of fecal recovery of the compound and/or its metabolites after administration (e.g., greater than 50% at 72 hours); (iii) specific numbers of NH and/or OH and/or potentially hydrogen bond donor moieties (e.g., greater than about five); (iv) specific numbers of rotatable bonds (e.g., greater than about five); (iv) specific permeability features (e.g., $P_{app}$ less than about $100 \times 10^{-6}$ cm/s); and/or any of a number of other features and characteristics as described herein.

The compounds of the present invention offer numerous advantages in the treatment of GI tract and other disorders. For example, the compounds are active on the phosphate transporter apically located in the intestine and essentially do not reach other phosphate transporters expressed in other tissues and organs. For instance the NaPi2b transporter is primarily expressed in the apical membrane of intestinal enterocytes, but is also found in salivary glands, mammary glands, lung, kidney, pancreas, ovary, prostate, testis and liver (Feild et al., 1999, Biochem Biophys Res Commun, v. 258, no. 3, p. 578-582; Bai et al., 2000, Am J Physiol Cell Physiol, v. 279, no. 4, p. C1135-C1143; Virkki et al., 2007, Am J Physiol Renal Physiol, v. 293, no. 3, p. F643-F654). Genome wide single-nucleotide polymorphism analysis in patients with pulmonary alveolar microlithiasis (PAM) has revealed a link between a mutated NaPi2b gene and disorder in which microliths are formed in the lung alveolar space. Homozygous inactivating mutations of pulmonary NaPi2b have also been implicated in the pathophysiology of PAM (Huqun et al., 2007, Am J Respir Crit Care Med, v. 175, no. 3, p. 263-268). Consistent with this human study, calcification nodules were evident in NaPi2b conditional knockout mice but not in wild type animals after NaPi2b deletion. In contrast, analysis of kidney and ileum samples revealed no pathologic abnormalities associated with Npt2b deletion (Sabbagh et al., 2009, J Am Soc. Nephrol., 20: 2348-2358).

The essentially non-systemic NaPi2b inhibitors of the present invention do not interfere with the pulmonary function of NaPi2b and, therefore, potential pulmonary toxicity is minimized. In addition, certain patient populations to whom the compounds of the invention may be administered are expected to have limited kidney clearance rate secondary to a declining kidney function. Thus, systemic compounds with some kidney clearance contribution in their excretion pathway can accumulate in the plasma, potentially leading to undesired side-effects in those patients with chronic kidney disease (Sica, 2008, J Clin Hypertens. (Greenwich.), v. 10, no. 7, p. 541-548). The compounds of the invention do not give rise to these same concerns because of their limited systemic availability.

As further detailed below, phosphate absorption in the upper intestine is mediated, at least in part, by a carrier-mediated mechanism which couples the absorption of phosphate to that of sodium. Accordingly, inhibition of intestinal phosphate transport will reduce body phosphorus overload. In patients with advanced kidney disease (e.g. stage 4 and 5), the body phosphorus overload manifests itself by serum phosphate concentration above normal levels, i.e. hyperphosphatemia. Hyperphosphatemia is directly related to mortality and morbidity. Inhibition of intestinal phosphate transport will reduce serum phosphate concentration and therefore improve outcome in those patients. In stage 2 and 3 chronic kidney disease patients, the body phosphorus overload does not necessarily lead to hyperphosphatemia, i.e. patients remain normophosphatemic, but there is a need to reduce body phosphorus overload even at those early stages to avoid associated bone and vascular disorders, and ultimately improve mortality rate. Similarly, inhibition of intestinal phosphate transport will be particularly advantageous in patients that have a disease that is treatable by inhibiting the uptake of phosphate from the intestines Inhibition of phosphate absorption from the glomerular filtrate within the kidneys would also be advantageous for treating chronic renal failure. Furthermore, inhibition of phosphate transport may slow the progression of renal failure and reduce risk of cardiovascular events.

Without being held to any particular theory, it is generally believed that, in vertebrates, phosphate (Pi) transporters use the inwardly directed electrochemical gradient of Na+ ions, established by the Na/K ATPase transporter, to drive Pi influx. These transporters fall in three distinct and unrelated Pi transporters proteins named type I, II and III. NaPi type I transporters comprise NaPi-I, mainly expressed in the proximal and distal renal tubules. NaPi type II transporters comprise NaPi2a, NaPi2b, and NaPi2c. NaPi2a is localized in the apical membrane of proximal renal tubule, but is also detected in rat brain, osteoclasts and osteoblast-like cells. NaPi2b is expressed in the apical membrane of enterocytes, but also found in lung, colon, testis and liver (see, e.g., Virkki, L. V., et al., Phosphate Transporters: A Tale of Two Solute Carrier Families, Am. J. Physiol. Renal. Physiol., 293(3):F643-54 (2007)). Type III NaPi transporters comprise PiT-1 and PiT-2, which are now emerging as important players in bone Pi metabolism and vascular calcification.

NaPi2a is believed to play a key role in phosphorus homeostasis by controlling the reabsorption of Pi in the renal proximal tubule. This is exemplified in NaPi2a KO mice, which develop hyperphosphaturia and hypophosphatemia. NaPi2b is believed responsible for transepithelial absorption in the small intestine and is regulated by dietary Pi and vitamin D (Calcitriol (1,25-Dihydroxycholecalciferol)). NaPi2c is expressed in renal tubule and other tissues (see, e.g., Virkki, L. V., et al., Id.).

The basic transport mechanism of NaPi2a and NaPi2b is the same (see, e.g., Murer, H., et al., Proximal Tubular Phosphate Reabsorption: Molecular Mechanisms, Physiol. Rev., 80(4):1373-409 (2000)); both are electrogenic with a stoichiometry of about 3:1 $Na^+{:}HPO_4^{2-}$, meaning that 3 $Na^+$ are co-transported with one phosphate anion. The additional Na cations translocated are excreted on the basolateral membrane via the K/Na ATPase active transporters to preserve cell polarization. Renal Pi transporter NaPi2a activity is increased in the kidney in response to low dietary Pi (see, e.g., Murer, et al., Id.). This results from an increase in transporter expression on the apical membrane of the kidney tubule. Histochemical analysis suggests a "recruitment" phenomenon. It is to be noted that, in contrast, the type I Na-Pi transporter does not respond to change in dietary P. The change in NaPi2a expression is paralleled by alteration in parathyroid hormone PTH plasma concentration and vice-versa (e.g., injection of PTH in rats leads within minutes to a reduction in brush border membrane transporter content). Acid-base change can also alter expression of NaPi2a. Chronic metabolic acidosis in rats significantly decreases NaPi2a protein and mRNA content. The same is observed in CKD rats induced by $\frac{5}{6}^{th}$ nephrectomy. The regulation of apical NaPi2a transporters involves complex membrane retrieval and re-insertion mechanisms. Control in transport activity can also be controlled by changes in intra-tubular and intracellular pH, in transmembrane potential difference and posttranslational modification.

Substantially Impermeable or Substantially Systemically Non-bioavailable Phosphate Transport Inhibitor Compounds A. Physical and Performance Properties In accordance with the present disclosure, the compounds described herein are designed to be substantially active or localized in the gastrointestinal lumen of a human or animal subject. The term "gastrointestinal lumen" is used interchangeably herein with the term "lumen," to refer to the space or cavity within a gastrointestinal tract (GI tract, which can also be referred to as the gut), delimited by the apical membrane of GI epithelial cells of the subject. In some embodiments, the compounds are not absorbed through the layer of epithelial cells of the GI tract (also known as the GI epithelium). "Gastrointestinal mucosa" refers to the layer(s) of cells separating the gastrointestinal lumen from the rest of the body and includes gastric and intestinal mucosa, such as the mucosa of the small intestine. A "gastrointestinal epithelial cell" or a "gut epithelial cell" as used herein refers to any epithelial cell on the surface of the gastrointestinal mucosa that faces the lumen of the gastrointestinal tract, including, for example, an epithelial cell of the stomach, an intestinal epithelial cell, a colonic epithelial cell, and the like.

"Substantially systemically non-bioavailable" and/or "substantially impermeable" as used herein (as well as variations thereof) generally refer to situations in which a statistically significant amount, and in some embodiments essentially all of the compound of the present disclosure, remains in the gastrointestinal lumen. For example, in accordance with one or more embodiments of the present disclosure, preferably at least about 70%, about 80%, about 90%, about 95%, about 98%, about 99%, or even about 99.5%, of the compound remains in the gastrointestinal lumen. In such cases, localization to the gastrointestinal lumen refers to reducing net movement across a gastrointestinal layer of epithelial cells, for example, by way of both transcellular and paracellular transport, as well as by active and/or passive transport. The compound in such embodiments is hindered from net permeation of a layer of gastrointestinal epithelial cells in transcellular transport, for example, through an apical membrane of an epithelial cell of the small intestine. The compound in these embodiments is also hindered from net permeation through the "tight junctions" in paracellular transport between gastrointestinal epithelial cells lining the lumen.

In this regard it is to be noted that, in one particular embodiment, the compound is essentially not absorbed at all by the GI tract or gastrointestinal lumen. As used herein, the terms "substantially impermeable" or "substantially systemically non-bioavailable" refers to embodiments wherein no detectable amount of absorption or permeation or systemic exposure of the compound is detected, using means generally known in the art.

In this regard it is to be further noted, however, that in alternative embodiments "substantially impermeable" or "substantially systemically non-bioavailable" provides or allows for some limited absorption in the GI tract, and more particularly the gut epithelium, to occur (e.g., some detectable amount of absorption, such as for example at least about 0.1%, 0.5%, 1% or more and less than about 30%, 20%, 10%, 5%, etc., the range of absorption being for example between about 1% and 30%, or 5% and 20%, etc.); stated another way, "substantially impermeable" or "substantially systemically non-bioavailable" refers to compounds that exhibit some detectable permeability to an epithelial layer of cells in the GI tract of less than about 20% of the administered compound (e.g., less than about 15%, about 10%, or even about 5%, and for example greater than about 0.5%, or 1%), but then are cleared by the liver (i.e., hepatic extraction) and/or the kidney (i.e., renal excretion).

In this regard it is to be further noted, that in certain embodiments, due to the substantial impermeability and/or substantial systemic non-bioavailability of the compounds of the present invention, greater than about 50%, 60%, 70%, 80% or 90% of a compound of the invention is recoverable from the feces over, for example, a 24, 48 or 72 hour period following administration to a patient in need thereof. In this respect, it is understood that a recovered compound can include the sum of the parent compound and its metabolites derived from the parent compound, e.g., by means of hydrolysis, conjugation, reduction, oxidation, N-alkylation, glucuronidation, acetylation, methylation, sulfation, phosphorylation, or any other modification that adds atoms to or removes atoms from the parent compound, wherein the metabolites are generated via the action of any enzyme or exposure to any physiological environment including, pH, temperature, pressure, or interactions with foodstuffs as they exist in the digestive milieu. Measurement of fecal recovery of compound and metabolites can be carried out using standard methodology. For example, compound can be administered orally at a suitable dose (e.g., 10 mg/kg) and feces are then collected at predetermined times after dosing (e.g., 24 hours, 48 hours, 72 hours). Parent compound and metabolites can be extracted with organic solvent and analyzed quantitatively using mass spectrometry. A mass balance analysis of the parent compound and metabolites (including, parent=M, metabolite 1 [M+16], and metabolite 2 [M+32]) can be used to determine the percent recovery in the feces.

In certain preferred embodiments, the phosphate transport inhibitors of the present invention are not competitive inhibitors with respect to phosphate of Na/phosphate co-transport. In certain other preferred embodiments, the phosphate transport inhibitors of the invention are non-competitive inhibitors. Non-competitive inhibitors maintain their degree of inhibition irrespective of the local phosphate concentration. This feature is an important aspect in providing an efficient blockade of intestinal transport in postprandial state, where the local concentration of dietary phosphate can attain concentration as high as 10 mM. It is believed that competitive inhibitors are too sensitive to local phosphate concentration and unable to block phosphate uptake following a high phosphorus meal. Various methods are available for determining whether a phosphate transport inhibitor is non-competitive or competitive. For example, a phosphate uptake assay can be performed and the $IC_{50}$ values for a compound at different phosphate concentrations can be determined (e.g., "Enzyme kinetics", I. Segel, 1975, John-Wiley & Sons, p. 123). $IC_{50}$ values for non-competitive inhibitors will remain the same or similar with respect to the phosphate concentration, whereas $IC_{50}$ values for competitive inhibitors will increase (i.e. lose potency) as phosphate concentration increases.

(i) Permeability

In this regard it is to be noted that, in various embodiments, the ability of the compound to be substantially systemically non-bioavailable is based on the compound charge, size, and/or other physicochemical parameters (e.g., polar surface area, number of hydrogen bond donors and/or acceptors therein, number of freely rotatable bonds, etc.). More specifically, it is to be noted that the absorption character of a compound can be selected by applying principles of pharmacokinetics, for example, by applying Lipinski's rule, also known as "the rule of five." Although not a rule, but rather a set of guidelines, Lipinski shows that small molecule drugs with (i) a molecular weight, (ii) a number of hydrogen bond donors, (iii) a number of hydrogen bond acceptors, and/or (iv) a water/octanol partition coefficient (Moriguchi Log P), greater than a certain threshold value, generally do not show significant systemic concentration (i.e., are generally not absorbed to any significant degree). (See, e.g., Lipinski et al., *Advanced Drug Delivery Reviews*, 46, 2001 3-26, incorporated herein by reference.) Accordingly, substantially systemically non-bioavailable compounds (e.g., substantially systemically non-bioavailable phosphate transport inhibitor compounds) can be designed to have molecular structures exceeding one or more of Lipinski's threshold values. (See also Lipinski et al., *Experimental and Computational Approaches to Estimate Solubility and Permeability in Drug Discovery and Development Settings*, Adv. Drug Delivery Reviews, 46:3-26 (2001); and Lipinski, *Drug-like Properties and the Causes of Poor Solubility and Poor Permeability*, J. Pharm. & Toxicol. Methods, 44:235-249 (2000), incorporated herein by reference.)

In some embodiments, for example, a substantially impermeable or substantially systemically non-bioavailable phosphate transport inhibitor compound of the present disclosure can be constructed to feature one or more of the following characteristics: (i) a MW greater than about 500 Da, about 1000 Da, about 2500 Da, about 5000 Da, about 10,000 Da or more (in the non-salt form of the compound); (ii) a total number of NH and/or OH and/or other potential hydrogen bond donors greater than about 5, about 10, about 15 or more; (iii) a total number of O atoms and/or N atoms and/or other potential hydrogen bond acceptors greater than about 5, about 10, about 15 or more; (iv) a Moriguchi partition coefficient greater than about $10^5$ (i.e., Log P greater than about 5, about 6, about 7, etc.), or alternatively less than about 10 (i.e., a Log P of less than 1, or even 0); and/or (v) a total number of rotatable bonds greater than about 5, about 10 or about 15, or more.

In addition to the parameters noted above, the molecular polar surface area (i.e., "PSA"), which may be characterized as the surface belonging to polar atoms, is a descriptor that has also been shown to correlate well with passive transport through membranes and, therefore, allows prediction of transport properties of drugs. It has been successfully applied for the prediction of intestinal absorption and Caco2 cell monolayer penetration. (For Caco2 cell monolayer penetration test details, see for example the description of the Caco2 Model provided in Example 31 of U.S. Pat. No. 6,737,423, the entire contents of which are incorporated herein by reference, and the text of Example 31 in particular, which may be applied for example to the evaluation or testing of the compounds of the present disclosure.) PSA is expressed in $Å^2$ (squared angstroms) and is computed from a three-dimensional molecular representation. A fast calculation method is also available (see, e.g., Ertl et al., *Journal of Medicinal Chemistry*, 2000, 43, 3714-3717, the entire contents of which are incorporated herein by reference for all relevant and consistent purposes) using a desktop computer and commercially available chemical graphic tools packages, such as ChemDraw. The term "topological PSA" (tPSA) has been coined for this fast-calculation method. tPSA is well correlated with human absorption data with common drugs (see, e.g., Table 1, below):

TABLE 1

| name | % FA[a] | TPSA[b] |
|---|---|---|
| metoprolol | 102 | 50.7 |
| nordiazepam | 99 | 41.5 |
| diazepam | 97 | 32.7 |
| oxprenolol | 97 | 50.7 |
| phenazone | 97 | 26.9 |
| oxazepam | 97 | 61.7 |
| alprenolol | 96 | 41.9 |
| practolol | 95 | 70.6 |
| pindolol | 92 | 57.3 |
| ciprofloxacin | 69 | 74.6 |
| metolazone | 64 | 92.5 |
| tranexamic acid | 55 | 63.3 |
| atenolol | 54 | 84.6 |
| sulpiride | 36 | 101.7 |
| mannitol | 26 | 121.4 |
| foscarnet | 17 | 94.8 |
| sulfasalazine | 12 | 141.3 |
| olsalazine | 2.3 | 139.8 |
| lactulose | 0.6 | 197.4 |
| raffinose | 0.3 | 268.7 |

(from Ertl et al., *J. Med. Chem.*, 2000, 43:3714-3717). Accordingly, in some embodiments, the compounds of the present disclosure may be constructed to exhibit a tPSA value greater than about 100 $Å^2$, about 120 $Å^2$, about 130 $Å^2$, or about 140 $Å^2$, and in some instances about 150 $Å^2$, about 160 $Å^2$, about 170 $Å^2$, about 180 $Å^2$, about 190 $Å^2$, about 200 $Å^2$, about 225 $Å^2$, about 250 $Å^2$, about 270 $Å^2$, about 300 $Å^2$, about 350 $Å^2$, about 400 $Å^2$, about 450 $Å^2$, about 500 $Å^2$, about 750 $Å^2$, or even about 1000 $Å^2$, such that the compounds are substantially impermeable or substantially systemically non-bioavailable (as defined elsewhere herein).

Because there are exceptions to Lipinski's "rule," or the tPSA model, the permeability properties of the compounds of the present disclosure may be screened experimentally. The permeability coefficient can be determined by methods known to those of skill in the art, including for example by Caco-2 cell permeability assay and/or using an artificial membrane as a model of a gastrointestinal epithelial cell. A synthetic membrane impregnated with, for example, lecithin and/or dodecane to mimic the net permeability characteristics of a gastrointestinal mucosa may be utilized as a model of a gastrointestinal mucosa. The membrane can be used to separate a compartment containing the compound of the present disclosure from a compartment where the rate of permeation will be monitored. Also, parallel artificial membrane permeability assays (PAMPA) can be performed. Such in vitro measurements can reasonably indicate actual permeability in vivo. (See, for example, Wohnsland et al., *J. Med. Chem.*, 2001, 44:923-930; Schmidt et al., Millipore Corp. Application Note, 2002, n○ AN1725EN00, and n○ AN1728EN00, incorporated herein by reference.)

Accordingly, in some embodiments, the compounds utilized in the methods of the present disclosure may have a permeability coefficient, $P_{app}$, of less than about $100 \times 10^{-6}$ cm/s, or less than about $10 \times 10^{-6}$ cm/s, or less than about $1 \times 10^{-6}$ cm/s, or less than about $0.1 \times 10^{-6}$ cm/s, when measured using means known in the art (such as for example the permeability experiment described in Wohnsland et al., *J. Med. Chem.*, 2001, 44. 923-930, the contents of which is incorporated herein by reference).

As previously noted, in accordance with the present disclosure, phosphate transport inhibitors may be modified to hinder their net absorption through a layer of gut epithelial cells, rendering them substantially systemically non-bioavailable. In some particular embodiments, the compounds of the present disclosure comprise a phosphate transport inhibitor linked, coupled or otherwise attached to a non-absorbable moiety, which may be an oligomer moiety, a polymer moiety, a hydrophobic moiety, a hydrophilic moiety, and/or a charged moiety, which renders the overall compound substantially impermeable or substantially systemically non-bioavailable. In some preferred embodiments, the phosphate transport inhibitor is coupled to a multimer or polymer portion or moiety, such that the resulting molecule is substantially impermeable or substantially systemically non-bioavailable. The multimer or polymer portion or moiety may be of a molecular weight greater than about 500 Daltons (Da), about 1000 Da, about 2500 Da, about 5000 Da, about 10,000 Da or more, and in particular may have a molecular weight in the range of about 1000 Daltons (Da) to about 500,000 Da, preferably in the range of about 5000 to about 200,000 Da, and more preferably may have a molecular weight that is sufficiently high to essentially preclude any net absorption through a layer of gut epithelial cells of the compound. In these or other particular embodiments, the phosphate transport inhibitor is modified to substantially hinder its net absorption through a layer of gut epithelial cells.

(ii) Persistent Inhibitory Effect

In other embodiments, the substantially impermeable or substantially systemically non-bioavailable compounds utilized in the treatment methods of the present disclosure may additionally exhibit a persistent inhibitor effect. This effect manifests itself when the inhibitory action of a compound at a certain concentration in equilibrium with epithelial cells (e.g., at or above its inhibitory concentration, IC) does not revert to baseline (i.e., phosphate transport without inhibitor) after the compound is depleted by simple washing of the luminal content.

This effect can be interpreted as a result of the tight binding of the compounds to the phosphate transport protein at the intestinal apical side of the gut epithelial cell. The binding can be considered as quasi-irreversible to the extent that, after the compound has been contacted with the gut epithelial cell and subsequently washed off said gut epithelial cell, the flux of phosphate transport is still significantly lower than in the control without the compound. This persistent inhibitory effect has the clear advantage of maintaining drug activity within the GI tract even though the residence time of the active in the upper GI tract is short, and when no enterobiliary recycling process is effective to replenish the compound concentration near its site of action.

Such a persistent inhibitory effect has an obvious advantage in terms of patient compliance, but also in limiting drug exposure within the GI tract.

The persistence effect can be determined using in vitro methods; in one instance, cell lines expressing phosphate transporters are split in different vials and treated with a phosphate transport inhibiting compound and phosphate solution to measure the rate of phosphate uptake. The cells in one set of vials are washed for different periods of time to remove the inhibitor, and phosphate uptake measurement is repeated after the washing. Compounds that maintain their inhibitory effect after multiple/lengthy washing steps (compared to the inhibitory effect measured in the vials where washing does not occur) are persistent inhibitors. Persistence effect can also be characterized ex vivo by using the everted sac technique, whereby transport of phosphate is monitored using an excised segment of GI perfused with a solution containing the inhibitor and shortly after flushing the bathing solution with a buffer solution free from inhibitor. A persistence effect can also be characterized in vivo by observing the time needed for phosphate balance to return to normal when the inhibitor treatment is discontinued. The limit of the method resides in the fact that apical cells (and therefore apical phosphate transporters) are sloughed off after a period of 3 to 4 days, the typical turnover time of gut epithelial cells. A persistence effect can be achieved by increasing the residence time of the active compound at the apical surface of the gut epithelial cells; this can be obtained by designing phosphate transport inhibitors with several phosphate transport inhibiting moieties built-in the small molecule or oligomer (wherein "several" as used herein typically means at least about 2, about 4, about 6 or more). Examples of such structures in the context of analogs of the antibiotic vancomycin are given in Griffin, et al., *J. Am. Chem. Soc.*, 2003, 125, 6517-6531. Alternatively the compound comprises groups that contribute to increase the affinity towards the gut epithelial cell so as to increase the time of contact with the gut epithelial cell surface. Such groups are referred to as being "mucoadhesive." More specifically, the Core or L moiety can be substituted by such mucoadhesive groups, such as polyacrylates, partially deacetylated chitosan or polyalkylene glycol. (See also Patil, S. B. et al., *Curr. Drug. Deliv.*, 2008, Oct. 5(4), pp. 312-8.)

(iii) GI Enzyme Resistance

Because the compounds utilized in the treatment methods of the present disclosure are preferably substantially systemically non-bioavailable, and/or preferably exhibit a persistent inhibitory effect, it is also desirable that, during their prolonged residence time in the gut, these compounds resist the hydrolytic conditions prevailing in the upper GI tract. In such embodiments, compounds of the present disclosure are resistant to phase 1 and phase 2 metabolism. For example, administered compounds are preferably resistant to the activity of P450 enzymes, glucurosyl transferases, sulfotransferases, glutathione S-transferases, and the like, in the intestinal mucosa, as well as gastric (e.g., gastric lipase, and pepsine), pancreatic (e.g., trypsin, triglyceride pancreatic lipase, phospholipase A2, endonucleases, nucleotidases, and alpha-amylase), and brush-border enzymes (e.g., alkaline phosphatase, glycosidases, and proteases) generally known in the art.

The compounds that are utilized in methods of the present disclosure are also preferably resistant to metabolism by the bacterial flora of the gut; that is, the compounds are not substrates for enzymes produced by bacterial flora. In addition, the compounds administered in accordance with the methods of the present disclosure may be substantially inactive towards the gastrointestinal flora, and do not disrupt bacterial growth or survival. As a result, in various embodiments herein, the minimal inhibitory concentration (or "MIC") against GI flora is desirably greater than about 15 µg/ml, about 30 µg/ml, about 60 µg/ml, about 120 µg/ml, or even about 240 µg/ml, the MIC in various embodiments being for example between about 16 and about 32 µg/ml, or between about 64 and about 128 µg/ml, or greater than about 256 µg/ml.

To one skilled in the art of medicinal chemistry, metabolic stability can be achieved in a number of ways. Functionality susceptible to P450-mediated oxidation can be protected by, for example, blocking the point of metabolism with a halogen or other functional group. Alternatively, electron withdrawing groups can be added to a conjugated system to generally provide protection to oxidation by reducing the electrophilicity of the compound. Proteolytic stability can be achieved by avoiding secondary amide bonds, or by incorporating changes in stereochemistry or other modifications that prevent the drug from otherwise being recognized as a substrate by the metabolizing enzyme.

(iv) $C_{max}$ and $IC_{50}$

It is also to be noted that, in various embodiments of the present disclosure, one or more of the compounds detailed herein, when administered either alone or in combination with one or more additional pharmaceutically active compounds or agents to a patient in need thereof has a $C_{max}$ that is less than the $IC_{50}$ for NaPi2b, more specifically, less than about 10× (10 times) the $IC_{50}$, and, more specifically still, less than about 100× (100 times) the $IC_{50}$.

Additionally, or alternatively, it is also to be noted that, in various embodiments of the present disclosure, one or more of the compounds detailed herein, when administered either alone or in combination with one or more additional pharmaceutically active compounds or agents to a patient in need thereof, may have a $C_{max}$ of less than about 10 ng/ml, about 7.5 ng/ml, about 5 ng/ml, about 2.5 ng/ml, about 1 ng/ml, or about 0.5 ng/ml, the $C_{max}$ being for example within the range of about 1 ng/ml to about 10 ng/ml, or about 2.5 ng/ml to about 7.5 ng/ml.

Additionally, or alternatively, it is also to be noted that, in various embodiments of the present disclosure, one or more of the compounds detailed herein, when administered either alone or in combination with one or more additional pharmaceutically active compounds or agents to a patient in need thereof, may have a $IC_{50}$ of less than about 10 µM, about 7.5 µM, about 5 µM, about 2.5 µM, about 1 µM, or about 0.5 µM, the $IC_{50}$ being for example within the range of about 0.5 µM to about 10 µM, or about 0.5 µM to about 7.5 µM, or about 0.5 µM to about 5 µM, or about 0.5 µM to about 2.5 µM.

Additionally, or alternatively, it is also to be noted that, in various embodiments of the present disclosure, one or more of compounds detailed herein, when administered to a patient in need thereof, may have a ratio of $IC_{50}:C_{max}$, wherein $IC_{50}$ and $C_{max}$ are expressed in terms of the same units, of at least about 10, about 50, about 100, about 250, about 500, about 750, or about 1000.

Additionally, or alternatively, it is also to be noted that, in various embodiments of the present disclosure, wherein one or more of the compounds as detailed herein is orally administered to a patent in need thereof, within the therapeutic range or concentration, the maximum compound concentration detected in the serum, defined as $C_{max}$, is lower than the NaPi2b inhibitory concentration $IC_{50}$ of said compound. As previously noted, as used herein, $IC_{50}$ is defined as the quantitative measure indicating the concentration of the compound required to inhibit 50% of the NaPi2b transport activity in a cell based assay.

Pharmaceutical Compositions and Methods of Treatment

For the purposes of administration, the compounds of the present invention may be administered to a patient or subject as a raw chemical or may be formulated as pharmaceutical compositions. Pharmaceutical compositions of the present invention generally comprise a compound of the invention and a pharmaceutically acceptable carrier, diluent or excipient. The compound is present in the composition in an amount which is effective to treat a particular disease or condition of interest, as described herein, and preferably with acceptable toxicity to the patient. The activity of compounds can be determined by one skilled in the art, for example, as described in the Example below. Appropriate concentrations and dosages can be readily determined by one skilled in the art.

A compound or composition of the invention may be used in a method for treating essentially any disease or other condition in a patient which would benefit from phosphate uptake inhibition in the gastrointestinal tract.

For example, by way of explanation, but not limitation, kidney damage reduces the production and activity of renal 1-alpha hydroxylase, leading to lower 1,25-dihydroxy vitamin D. Decreased vitamin D levels limit gastrointestinal calcium absorption, leading to a decline in serum calcium levels. The combination of lower 1,25-dihydroxy vitamin D and lower serum calcium levels synergistically stimulate parathyroid tissue to produce and secrete PTH. A loss of nephrons also impairs Pi excretion, but serum P levels are actively defended by the actions of PTH and FGF-23, and by higher serum P levels, which considerably enhance urinary $PO_4$ excretion. However, tubular actions of PTH and FGF-23 cannot maintain serum P levels in the face of continual nephron loss. Once renal insufficiency progresses to the loss of about 40-50% of renal function, the decrease in the amount of functioning renal tissue does not allow excretion of the full amount of ingested phosphate required to maintain homeostasis. As a result, hyperphosphatemia develops. In addition, a rise in serum P levels impedes renal 1-alpha hydroxylase activity, further suppressing activated vitamin D levels, and further stimulating PTH, leading to secondary hyperparathyroidism (sHPTH).

Phosphorus imbalance, however, does not necessarily equate with hyperphosphatemia. In fact, the vast majority of CKD patients not yet on dialysis are normophosphatemic but their phosphorus balance is positive with the excess phosphorus being disposed in the vasculature in the form of ectopic calcification, e.g. intima localized vascular calcification. Clinically, patients with CKD have elevated levels of FGF-23 that are significantly associated with deteriorating renal function and with decreased calcitriol levels, and it has been hypothesized that the synthesis of FGF-23 is induced by the presence of excess P in the body consecutive to renal failure.

Furthermore, an unrecognized effect on cardiovascular disease is post-prandial phosphatemia, i.e. serum P excursion secondary to meal intake. Further still, studies have investigated the acute effect of phosphorus loading on endothelial function in vitro and in vivo. Exposing bovine arotic endothelial cells to a phosphorus load increased production of reactive oxygen species and decreased nitric oxide, a known vasodilator agent. In the acute P loading study in healthy volunteers described above, it was found that the flow mediated dilation correlated inversely with postprandial serum P (Shuto et al., 2009b, J. Am. Soc. Nephrol., v. 20, no. 7, p. 1504-1512).

Accordingly, in certain more specific embodiments, a compounds or composition of the invention can be used in a method selected from the group consisting of: (a) a method for treating hyperphosphatemia; (b) a method for treating a renal disease (e.g., chronic kidney disease or end stage renal disease); (c) a method for delaying time to dialysis; (d) a method for attenuating intima localized vascular calcification; (e) a method for reducing the hyperphosphatemic effect of active vitamin D; (f) a method for reducing FGF23 levels; (g) a method for attenuating hyperparathyroidism; (h) a method for improving endothelial dysfunction induced by postprandial serum phosphate; (i) a method for reducing urinary phosphorous; (j) a method for normalizing serum phosphorus levels; (k) a method for treating proteinura; and (l) a method for reducing serum PTH, calcium, calcitriol and/or phosphate concentrations or levels.

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, buccal, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington: The Science and Practice of Pharmacy,* 20th Edition (Philadelphia College of Pharmacy and Science, 2000). The composition to be administered will, in any event, contain a therapeutically effective amount of a compound of the invention, or a pharmaceutically acceptable salt thereof, for treatment of a disease or condition of interest in accordance with the teachings of this invention.

A pharmaceutical composition of the invention may be in the form of a solid or liquid. In one aspect, the carriers) are particulate, so that the compositions are, for example, in tablet or powder form. The carrier(s) may be liquid, with the compositions being, for example, an oral syrup, injectable liquid or an aerosol, which is useful in, for example, inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition may be in the form of a liquid, for example, an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device.

The pharmaceutical composition of the invention may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy.

In certain embodiments, a typical dosage of the substantially impermeable or substantially systemically non-bioavailable, compound may be between about 0.2 mg per day and about 2 g per day, or between about 1 mg and about 1 g per day, or between about 5 mg and about 500 mg, or between about 10 mg and about 250 mg per day, which is administered to a subject in need of treatment.

The frequency of administration of the compounds and compositions described herein may vary from once-a-day (QD) to twice-a-day (BID) or thrice-a-day (TID), etc., the precise frequency of administration varying with, for example, the patient's condition, the dosage, etc.

Compounds of the invention, or pharmaceutically acceptable derivatives thereof, may also be administered simultaneously with, prior to, or after administration of one or more other therapeutic agents. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and the other active agent can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

For example, in certain embodiments, the additional biologically active agent included in a pharmaceutical composition (or method) of the invention is selected, for example, from vitamin $D_2$ (ergocalciferol), vitamin $D_3$ (cholecalciferol), active vitamin D (calcitriol) and active vitamin D analogs (e.g. doxercalciferol, paricalcitol).

In other specific embodiments, the additional biologically active agent included in a pharmaceutical composition (or method) of the invention is a phosphate binder, such as Renvela, Renagel, Fosrenol, calcium carbonate, calcium acetate (e.g. Phoslo), MCI-196, Zerenex™, Fermagate, APS1585, SBR-759, PA-21, and the like.

The compounds of the invention have been found to act synergistically with phosphate binders by providing a higher efficacy than the sum of the efficacy of a NaPi2b inhibitor and that of a phosphate binder administered alone. Without wishing to be bound by theory, it is believed that the synergy results from the distinct mechanisms of action of a phosphate transport inhibitor and a phosphate binder. More specifically, a phosphate transport inhibitor blocks the epithelial inward transport of phosphate ions whereas phosphate binders sequester free phosphate ions in the lumen of the intestine.

The efficacy of a phosphate binder, as measured by its vivo binding capacity (mole of phosphate ions bound per gram of binder) is essentially dictated by: i) the density of binding sites (i e amine groups in Renvela/Sevelamer, a polymeric amine material; or multivalent cations such calcium or lanthanum in Phoslo (Calcium acetate) or Fosrenol (lanthanum carbonate)); and ii) the affinity of said binding sites for phosphate ions. Notably only a fraction of the binding sites is available for phosphate binding in vivo as other anions, such as bile acids and fatty acids compete for the binding sites and therefore lowers efficacy. Bound phosphate ions are in equilibrium with free phosphate in the intestinal lumen and are themselves subject to intense pumping from phosphate transport proteins lining up the epithelia. Experiments have shown that the efficacy of phosphate intestinal uptake is remarkably high, exceeding 95% of the phosphate presented to the epithelia. It is believed that the active transport of phosphate contributes to lower the luminal free phosphate concentration and therefore to drive the binding equilibrium of a phosphate binder to lower binding capacity. It is also believed that by reducing the phosphate intestinal transport using a phosphate transport inhibitor, one restores a higher in vivo binding capacity of phosphate sequestering agents. The synergistic effect is thought to be even more pronounced when the contribution of active phosphate transport is increased as a result of, e.g. vitamin D treatment, an agent promoting NaPi2b expression.

It is understood that in the present description, combinations of substituents and/or variables of the depicted formulae are permissible only if such contributions result in stable compounds.

It will also be appreciated by those skilled in the art that in the process described herein the functional groups of intermediate compounds may need to be protected by suitable protecting groups. Such functional groups include hydroxy, amino, mercapto and carboxylic acid. Suitable protecting groups for hydroxy include trialkylsilyl or diarylalkylsilyl (for example, t-butyldimethylsilyl, t-butyldiphenylsilyl or trimethylsilyl), tetrahydropyranyl, benzyl, and the like. Suitable protecting groups for amino, amidino and guanidino include t-butoxycarbonyl, benzyloxycarbonyl, and the like. Suitable protecting groups for mercapto include —C(O)—R" (where R" is alkyl, aryl or arylalkyl), p-methoxybenzyl, trityl and the like. Suitable protecting groups for carboxylic acid include alkyl, aryl or arylalkyl esters. Protecting groups may be added or removed in accordance with standard techniques, which are known to one skilled in the art and as described herein. The use of protecting groups is described in detail in Green, T. W. and P. G. M. Wutz, *Protective Groups in Organic Synthesis* (1999), 3rd Ed., Wiley. As one of skill in the art would appreciate, the protecting group may also be a polymer resin such as a Wang resin, Rink resin or a 2-chlorotrityl-chloride resin.

It will also be appreciated by those skilled in the art, although such protected derivatives of compounds of this invention may not possess pharmacological activity as such, they may be administered to a mammal and thereafter metabolized in the body to form compounds of the invention which are pharmacologically active. Such derivatives may therefore be described as "prodrugs". All prodrugs of compounds of this invention are included within the scope of the invention.

Furthermore, all compounds of the invention which exist in free base or acid form can be converted to their pharmaceutically acceptable salts by treatment with the appropriate inorganic or organic base or acid by methods known to one skilled in the art. Salts of the compounds of the invention can be converted to their free base or acid form by standard techniques.

The following Examples illustrate various methods of making compounds of this invention, i.e., compounds of structure (I). or a stereoisomer, prodrug or pharmaceutically acceptable salt thereof. It is understood that one skilled in the art may be able to make these compounds by similar methods or by combining other methods known to one skilled in the art. It is also understood that one skilled in the art would be able to make, in a similar manner as described below, other compounds of structure (I) not specifically illustrated below by using the appropriate starting components and modifying the parameters of the synthesis as needed. In general, starting components may be obtained from sources such as Sigma Aldrich, Lancaster Synthesis, Inc., Maybridge, Matrix Scientific, TCI, and Fluorochem USA, etc. or synthesized according to sources known to those skilled in the art (see, e.g., Advanced Organic Chemistry: Reactions, Mechanisms, and Structure, 5th edition (Wiley, December 2000)) or prepared as described in this invention.

The following examples are provided for purposes of illustration, not limitation.

EXAMPLES

Example 1

N1-Methyl-N1-(2-morpholinoethyl)-N3-(4-(piperidin-1-yl)-2-((3-(3-(trifluoromethyl)phenyl)-1H-1,2,4-triazol-5-yl)carbamoyl)phenyl)isophthalamide Scheme 1. 1. oxalyl chloride, DMF; 2. Boc₂O; 3. LAH; 4. intermediate 1a, Et₃N; 5. LiOH•H₂O; 6. oxalyl chloride, DMF; 7. SOCl₂, MeOH; 8. MeONa, MeOH, aminoguanidine carbonate; 9. NaH, THF, 5-chloro-2-nitrobenzoyl chloride; 10. piperidine, DMF; 11. Pd/C, MeOH; 12. pyridine, DCM, intermediate 1f.

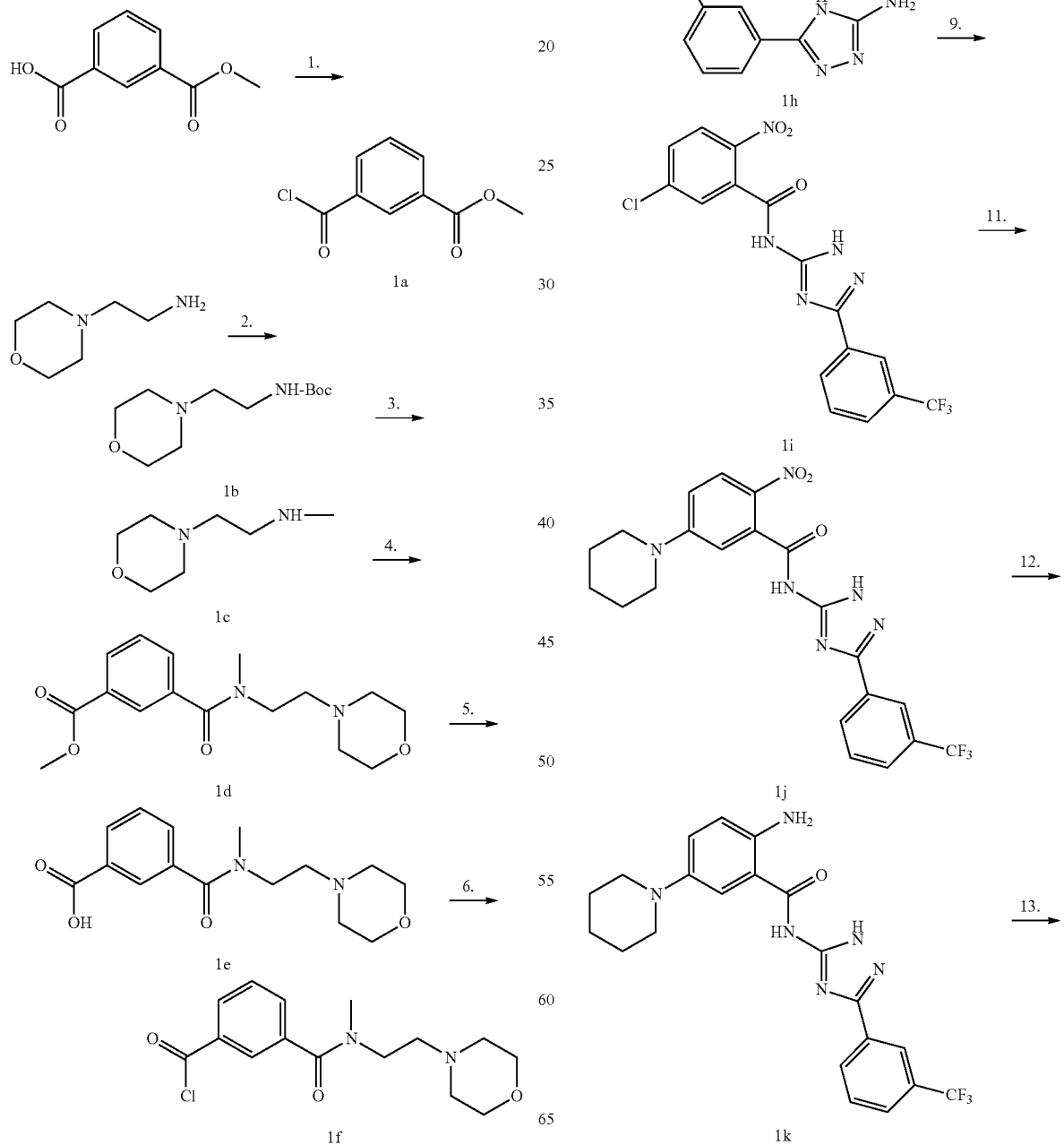

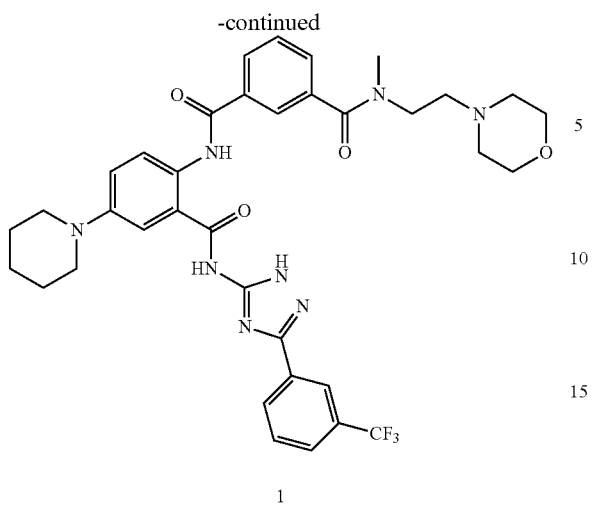

1

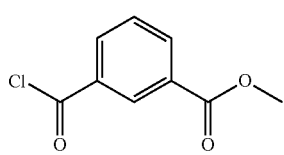

Intermediate 1a methyl 3-(chlorocarbonyl)benzoate

To 3-(methoxycarbonyl)benzoic acid (6.2 g, 34.44 mmol, 1.00 equiv) in dichloromethane (50 mL) was added oxalyl dichloride (8.74 g, 69.37 mmol, 2.00 equiv) and N,N-dimethylformamide (cat.) and the resulting solution was stirred for 1 h at 40° C. in an oil bath. The mixture was concentrated under vacuum to yield 6.6 g (87%) of methyl 3-chlorocarbonyl) benzoate as brown oil.

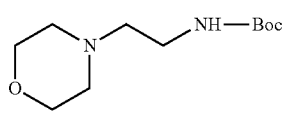 [SMILES: CC(C)(C)OC(=O)NCCN1CCOCC1]

Intermediate 1b tert-butyl(2-morpholinoethyl)carbamate

To a solution of 2-morpholinoethanamine (10 g, 76.92 mmol, 1.00 equiv) in dichloromethane (50 mL) was added triethylamine (5.83 g, 57.72 mmol, 0.50 equiv) followed by the addition of di-tert-butyl dicarbonate (18.44 g, 84.59 mmol, 1.10 equiv) at 0-5° C. and the resulting solution was stirred overnight at 25° C. The reaction was diluted with 200 mL of dichloromethane and washed with 1×30 mL of 10% sodium bicarbonate and 1×30 mL of brine. The organic layer was dried over sodium sulfate and concentrated under vacuum to afford 16 g (81%) of tert-butyl 2-morpholinoethylcarbamate as an off-white solid.

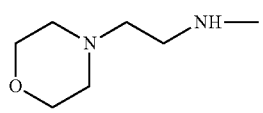

Intermediate 1c

N-methyl-2-morpholinoethanamine

To a solution of LiAlH$_4$ (7.72 g, 208.65 mmol, 3.00 equiv) in tetrahydrofuran (60 mL) at 0-5° C. was added dropwise a solution of tert-butyl 2-morpholinoethylcarbamate (16 g, 62.61 mmol, 1.00 equiv, 90%) in tetrahydrofuran (40 mL). The resulting solution was then stirred for 2 h at 70° C. in an oil bath. The reaction was then quenched by the addition of 7.7 mL of water, 7.7 mL of 15% sodium hydroxide, and 23.1 mL of water. The solids were filtered out. The mixture was dried over sodium sulfate and concentrated under vacuum. The residue was applied onto a silica gel column and eluted with dichloromethane:methanol (0.5% triethylamine) (20:1) to afford 4.2 g (42%) of N-methyl-2-morpholinoethanamine as a brown oil.

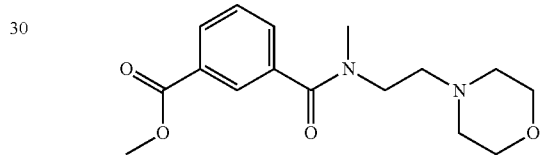

Intermediate 1d methyl 3-(methyl(2-morpholinoethyl)carbamoyl)benzoate

To a solution of N-methyl-2-morpholinoethanamine (2.1 g, 13.12 mmol, 1.00 equiv, 90%) in dichloromethane (20 mL) at 0-5° C. was added triethylamine (1.47 g, 14.55 mmol, 1.00 equiv) followed by dropwise addition of a solution of methyl 3-(chlorocarbonyl)benzoate (3.3 g, 15.00 mmol, 1.20 equiv, 90%) in dichloromethane (10 mL). The resulting solution was then stirred for 3 h at room temperature. The mixture was diluted with 100 mL of dichloromethane, washed with 1×30 mL of 10% sodium bicarbonate and 1×30 mL of brine, dried over sodium sulfate and then concentrated under vacuum. The residue was applied onto a silica gel column with dichloromethane:methanol (20:1) to afford 4.4 g (99%) of methyl 3-(methyl(2-morpholinoethyl)carbamoyl)benzoate as a brown solid.

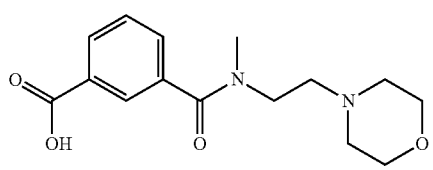 [SMILES: CN(CCN1CCOCC1)C(=O)c1cccc(C(=O)O)c1]

Intermediate 1e

3-(methyl(2-morpholinoethyl)carbamoyl)benzoic acid

To a solution of methyl 3-(methyl(2-morpholinoethyl)carbamoyl)benzoate (4.4 g, 13.66 mmol, 1.00 equiv, 95%) in tetrahydrofuran/water (15/10 mL) was added lithium hydroxide hydrate (1.77 g, 43.17 mmol, 3.00 equiv) and the resulting solution was stirred for 1 h at 25° C. The resulting mixture was concentrated under vacuum, diluted with 10 mL of water and then adjusted to pH 2-3 with hydrochloric acid. The resulting mixture was washed with 2×30 mL of ethyl acetate. The aqueous layers were concentrated under vacuum. The residue was applied onto a silica gel column and eluted with ethyl acetate:methanol (4:1) to give 2.7 g (65%) of 3-(methyl(2-morpholinoethyl)carbamoyl)benzoic acid as a white solid. $^1$H-NMR (300 MHz, CD$_3$OD, ppm): δ 8.17 (m, 2H), 7.78 (m, 1H), 7.61 (m, 1H), 3.98 (m, 6H), 3.56 (m, 5H), 3.47 (m, 1H), 3.10 (s, 3H). MS (ES, m/z): 293 [M+H]$^+$.

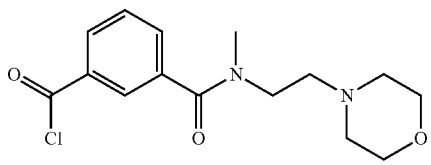 [SMILES: CN(CCN1CCOCC1)C(=O)c1cccc(C(=O)Cl)c1]

Intermediate 1f

3-(methyl(2-morpholinoethyl)carbamoyl)benzoyl chloride

To 3-(methyl(2-morpholinoethyl)carbamoyl)benzoic acid (1.37 g, 4.69 mmol, 1.00 equiv) in dichloromethane (17 mL) was added 2 drops of N,N-dimethylformamide followed by the addition of oxalyl dichloride (3.63 g, 28.14 mmol, 6.00 equiv). The resulting solution was stirred for 1 h at 50° C. in an oil bath then concentrated under vacuum to afford 1.41 g (87%) of 3-(methyl(2-morpholinoethyl)carbamoyl)benzoyl chloride as a gray-yellow solid.

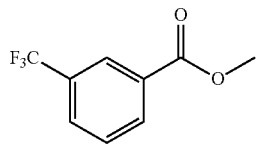

Intermediate 1g methyl 3-(trifluoromethyl)benzoate

To a solution of 3-(trifluoromethyl)benzoic acid (5 g, 26.30 mmol, 1.00 equiv) in methanol (25 mL) was added dropwise thionyl chloride (9.39 g, 78.93 mmol, 3.00 equiv) and the resulting solution was stirred for 2 h at 75° C. in an oil bath. The mixture was concentrated under vacuum, diluted with 100 mL of ethyl acetate and then washed with 2×30 mL of sodium carbonate and 2×30 mL of brine. The organic layer was dried over anhydrous sodium sulfate and concentrated under vacuum to yield 4.6 g (86%) of methyl 3-(trifluoromethyl)benzoate as yellow oil

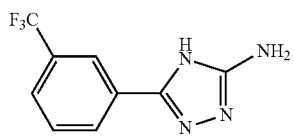 [SMILES: Nc1nnc(-c2cccc(C(F)(F)F)c2)[nH]1]

Intermediate 1h

5-(3-(trifluoromethyl)phenyl)-4H-1,2,4-triazol-3-amine

To a solution of sodium methanolate (1.05 g, 19.44 mmol, 4.00 equiv) in methanol (40 mL) at 0° C. was added aminoguanidine bicarbonate (2.66 g, 19.54 mmol, 4.00 equiv) in several batches. To this was added dropwise a solution of methyl 3-(trifluoromethyl)benzoate (1 g, 4.90 mmol, 1.00 equiv) in methanol (10 mL) with stirring at 0° C. The resulting solution was then stirred overnight at 75° C. in an oil bath. The reaction was then quenched with 10 mL of water/ice, the solution adjusted to pH 3-4 with hydrochloric acid (1 mol/L), and the solids were collected by filtration To afford 150 mg (13%) of 5-(3-(trifluoromethyl)phenyl)-4H-1,2,4-triazol-3-amine as a yellow solid.

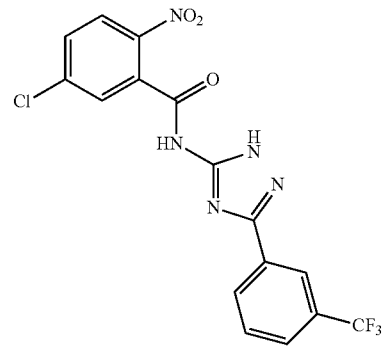

Intermediate 1i

5-chloro-2-nitro-N-(5-(3-(trifluoromethyl)phenyl)-2H-1,2,4-triazol-3-yl)-benzamide To a solution of 5-(3-(trifluoromethyl)phenyl)-2H-1,2,4-triazol-3-amine (100 mg, 0.44 mmol, 1.00 equiv) in tetrahydrofuran (1 mL) was added sodium hydride (35 mg, 0.88 mmol, 2.00 equiv, 60%) followed by the dropwise addition of a solution of 5-chloro-2-nitrobenzoyl chloride (96.49 mg, 0.44 mmol, 1.00 equiv) in tetrahydrofuran (1 mL) and the resulting solution was stirred for 2 h at room temperature. The mixture was diluted with 50 mL of ethyl acetate, washed with 2×20 mL of brine, dried over anhydrous sodium sulfate and concentrated under vacuum to afford 120 mg (67%) of a yellow solid.

35

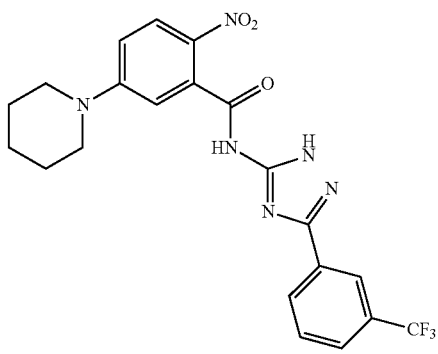

Intermediate 1j 2-nitro-5-(piperidin-1-yl)-N-(5-(3-(trifluoromethyl)phenyl)-2H-1,2,4-triazol-3-yl)benzamide To a solution of 5-chloro-2-nitro-N-(5-(3-(trifluoromethyl)phenyl)-2H-1,2,4-triazol-3-yl)benzamide (120 mg, 0.29 mmol, 1.00 equiv) in N,N-dimethylformamide (1 mL) was added piperidine (1 mL) and the resulting solution was stirred for 2 h at 100° C. in an oil bath. The mixture was diluted with 50 mL of ethyl acetate, washed with 2×20 mL of brine, dried over anhydrous sodium sulfate, and concentrated under vacuum to afford 130 mg (97%) of product as yellow oil.

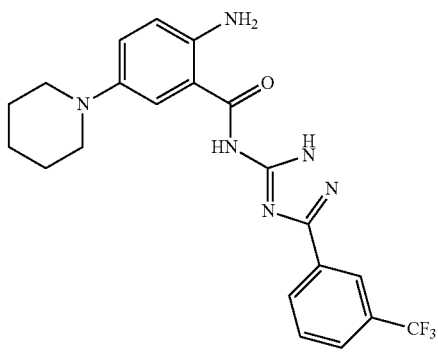

Intermediate 1k 2-amino-5-(piperidin-1-yl)-N-(5-(3-(trifluoromethyl)phenyl)-2H-1,2,4-triazol-3-yl)benzamide To a solution of 2-nitro-5-(piperidin-1-yl)-N-(5-(3-(trifluoromethyl)phenyl)-2H-1,2,4-triazol-3-yl)benzamide (130 mg, 0.28 mmol, 1.00 equiv) in methanol (3 mL) was added Pd/C (130 mg, 10%) and the suspension stirred under an atmosphere of hydrogen for 2 h at room temperature. The solids were filtered out and the resulting mixture was concentrated under vacuum to yield 50 mg (41%) of product as a yellow solid.

36

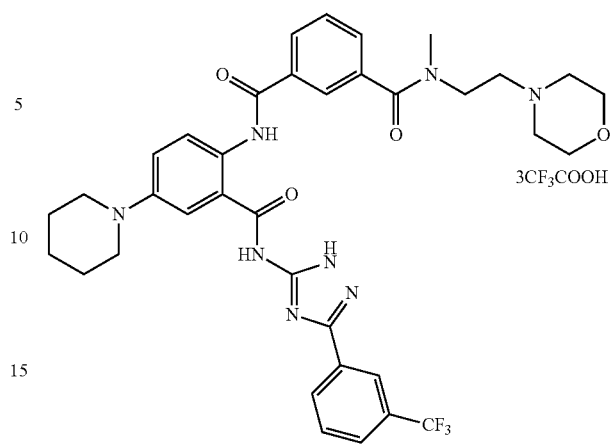

Example 1

N1-methyl-N1-(2-morpholinoethyl)-N3-(4-(piperidin-1-yl)-2-(5-(3-(trifluoromethyl)phenyl)-2H-1,2,4-triazol-3-ylcarbamoyl)phenyl)isophthalamide To a solution of 2-amino-5-(piperidin-1-yl)-N-(5-(3-(trifluoromethyl)phenyl)-2H-1,2,4-triazol-3-yl)benzamide (50 mg, 0.12 mmol, 1.00 equiv) in dichloromethane (3 mL) was added pyridine (73 mg, 0.92 mmol, 8.00 equiv) followed by the dropwise addition of a solution of 3-(methyl(2-morpholinoethyl)carbamoyl)benzoyl chloride (54 mg, 0.17 mmol, 1.50 equiv) in dichloromethane (2 mL) and the resulting solution was stirred for 30 min at room temperature. The mixture was diluted with 50 mL of ethyl acetate, washed with 2×20 mL of NH$_4$Cl and 2×20 mL of brine, dried over anhydrous sodium sulfate and then concentrated under vacuum. The crude product (50 mg) was purified by reverse phase HPLC eluting with a water/CH$_3$CN gradient containing 0.05% TFA. The product was obtained as 12 mg (10%) of a yellow solid. $^1$H-NMR (300 MHz, CD$_3$OD, ppm): δ 8.34(m, 3H), 8.17(t, J=7.8 Hz, 2H), 7.73(m, 5H), 7.42 (m, 1H), 3.98(s, 2H), 3.55(m, 3H), 3.40(m, 5H), 3.29(m, 1H), 3.09(m, 3H), 1.86(d, J=4.8 Hz, 4H), 1.71(t, J=5.1 Hz, 2H). MS (ES, m/z): 705 [M+H]$^+$.

Example 2

N1-Methyl-N1-(2-morpholinoethyl)-N3-(4-(piperidin-1-yl)-2-((1-(3-(trifluoromethyl)phenyl)-1H-1,2,4-triazol-3-yl)carbamoyl)phenyl)isophthalamide Scheme 2: 1. 3-(trifluoromethyl)phenyboronic acid, Cu(OAc)$_2$, pyridine; 2. H$_2$, Pd/C; 3. 2-nitro-5-chlorobenzoyl chloride, pyridine; 4. piperidine, DMF, K$_2$CO$_3$; 5. H$_2$, 6. Pd/C; pyridine, intermediate 1f.

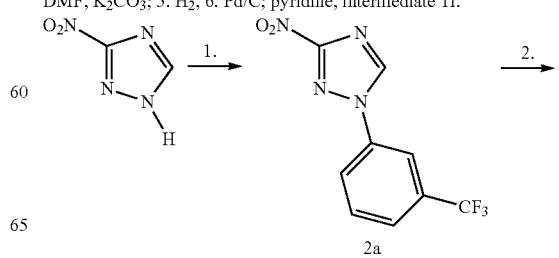

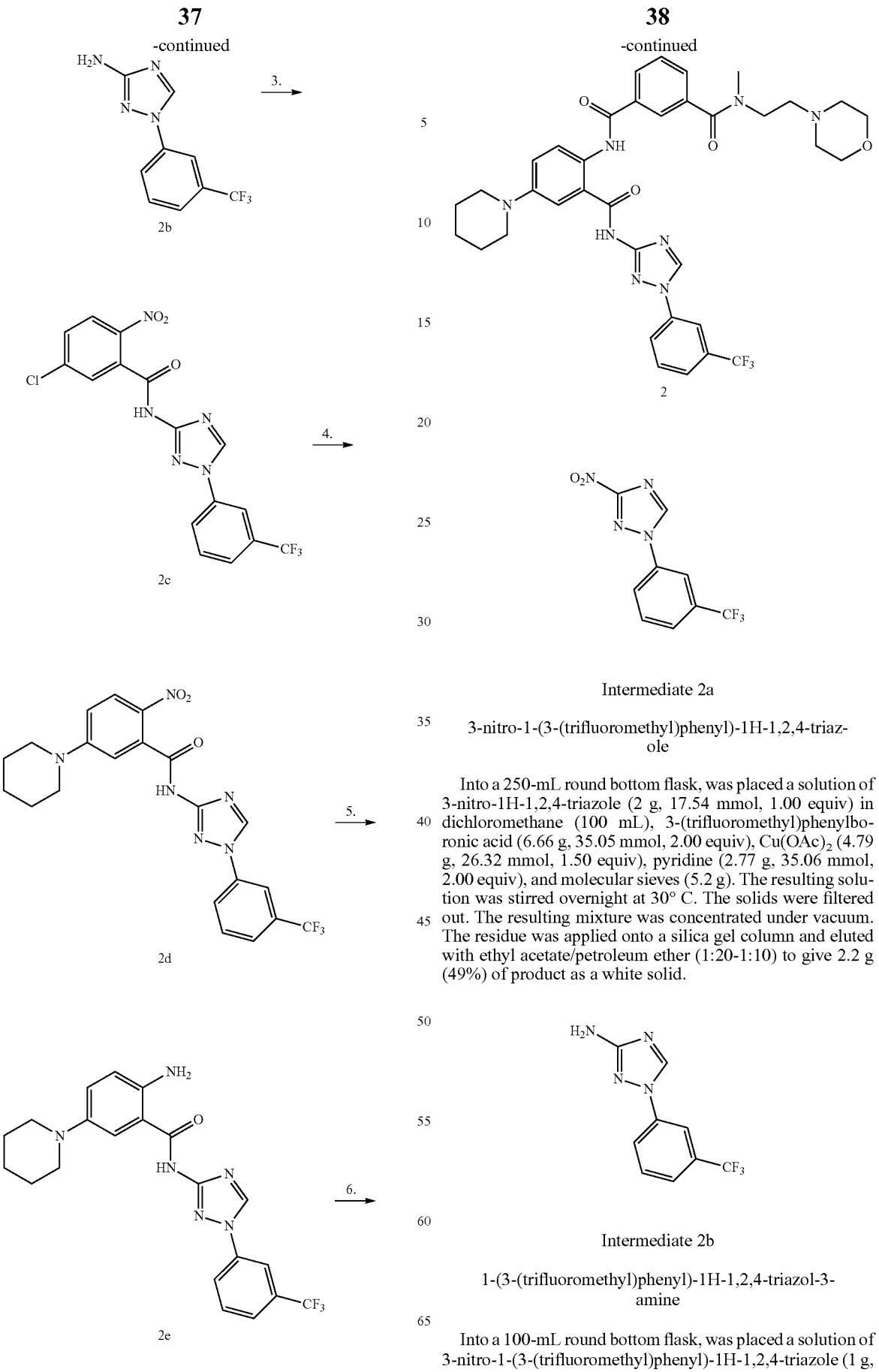

Intermediate 2a 3-nitro-1-(3-(trifluoromethyl)phenyl)-1H-1,2,4-triazole

Into a 250-mL round bottom flask, was placed a solution of 3-nitro-1H-1,2,4-triazole (2 g, 17.54 mmol, 1.00 equiv) in dichloromethane (100 mL), 3-(trifluoromethyl)phenylboronic acid (6.66 g, 35.05 mmol, 2.00 equiv), Cu(OAc)₂ (4.79 g, 26.32 mmol, 1.50 equiv), pyridine (2.77 g, 35.06 mmol, 2.00 equiv), and molecular sieves (5.2 g). The resulting solution was stirred overnight at 30° C. The solids were filtered out. The resulting mixture was concentrated under vacuum. The residue was applied onto a silica gel column and eluted with ethyl acetate/petroleum ether (1:20-1:10) to give 2.2 g (49%) of product as a white solid.

Intermediate 2b 1-(3-(trifluoromethyl)phenyl)-1H-1,2,4-triazol-3-amine

Into a 100-mL round bottom flask, was placed a solution of 3-nitro-1-(3-(trifluoromethyl)phenyl)-1H-1,2,4-triazole (1 g, 3.88 mmol, 1.00 equiv) in methanol (20 mL). The mixture was treated with Pd/C (1 g) and stirred under an atmosphere of hydrogen for 3 h at 25° C. in an oil bath. The solids were filtered out. The resulting mixture was concentrated under vacuum to yield 900 mg of crude product as a white solid.

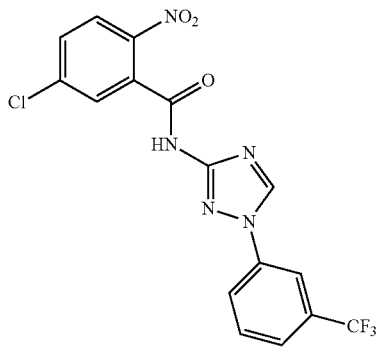 [SMILES: O=C(Nc1ncn(-c2cccc(C(F)(F)F)c2)n1)c1cc(Cl)ccc1[N+](=O)[O-]]

Intermediate 2c 5-chloro-2-nitro-N-(1-(3-trifluoromethyl)phenyl)-1H-1,2,4-triazol-3-yl)benzamideas Into a 100-mL round bottom flask, was placed a solution of 1-(3-(trifluoromethyl)phenyl)-1H-1,2,4-triazol-3-amine (1 g, 4.39 mmol, 1.00 equiv) in dichloromethane (20 mL), and pyridine (1.15 g, 14.56 mmol, 3.00 equiv). This was followed by dropwise addition of a solution of 5-chloro-2-nitrobenzoyl chloride (1.04 g, 4.75 mmol, 1.10 equiv) in dichloromethane (5 mL) with stirring at 0-5° C. The resulting solution was stirred for 2 h at 0-5° C. The resulting solution was diluted with 50 mL of dichloromethane. The resulting mixture was washed with 2×50 mL of aqueous hydrochloric acid, dried over anhydrous sodium sulfate, and concentrated under vacuum. This resulted in 2 g of crude product as a white-yellow solid.

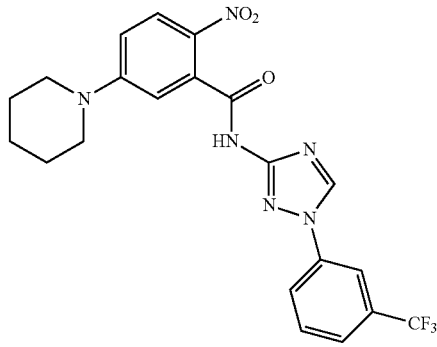 [SMILES: O=C(Nc1ncn(-c2cccc(C(F)(F)F)c2)n1)c1cc(N2CCCCC2)ccc1[N+](=O)[O-]]

Intermediate 2d 2-nitro-5-(piperidin-1-yl)-N-(1-(3-(trifluoromethyl)phenyl)-1H-1,2,4-triazol-3-yl)benzamide Into a 100-mL round bottom flask, was placed a solution of 5-chloro-2-nitro-N-(1-(3-(trifluoromethyl)phenyl)-1H-1,2,4-triazol-3-yl)benzamide (500 mg, 1.21 mmol, 1.00 equiv) in N,N-dimethylformamide (10 mL), and piperidine (500 mg, 5.88 mmol, 4.84 equiv). The resulting solution was stirred overnight at 90° C. The resulting mixture was concentrated under vacuum. The residue was dissolved in 30 mL of ethyl acetate. The resulting mixture was washed with 2×50 mL of brine, dried over anhydrous sodium sulfate, and concentrated under vacuum. This resulted in 500 mg (90%) of product as white oil.

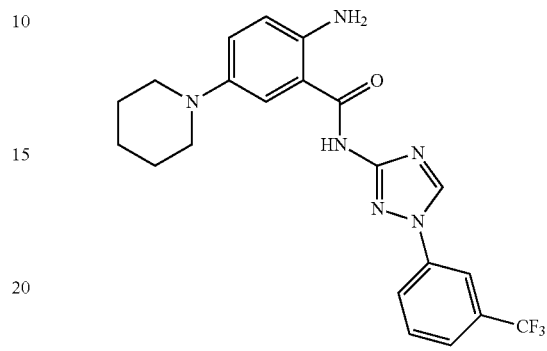

Intermediate 2e 2-amino-5-(piperidin-1-yl)-N-(1-(3-(trifluoromethyl)phenyl)-1H-1,2,4-triazol-3-yl)benzamide Into a 100-mL round bottom flask, was placed a solution of 2-nitro-5-(piperidin-1-yl)-N-(1-(3-(trifluoromethyl)phenyl)-1H-1,2,4-triazol-3-yl)benzamide (500 mg, 1.09 mmol, 1.00 equiv) in methanol (20 mL). The solution was treated with Pd/C (500 mg) and stirred under an atmosphere of hydrogen for 2 h at room temperature. The solids were filtered out. The resulting mixture was concentrated under vacuum to yield 450 mg (96%) of product as a brown solid.

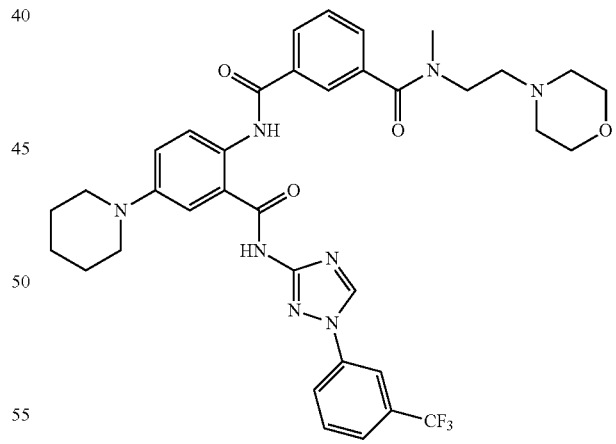

Example 2

N1-methyl-N1-(2-morpholinoethyl)-N3-(4-(piperidin-1-yl)-2-((1-(3-(trifluoromethyl)phenyl)-1H-1,2,4-triazol-3-yl)carbamoyl)phenyl)isophthalamide Into a 100-mL round bottom flask, was placed a solution of 2-amino-5-(piperidin-1-yl)-N-(1-(3-(trifluoromethyl)phenyl)-1H-1,2,4-triazol-3-yl)benzamide (150 mg, 0.35 mmol, 1.00 equiv) in dichloromethane (20 mL), and pyridine (83 mg, 1.05 mmol, 3.01 equiv). This was followed by dropwise addition of a solution of 3-(methyl(2-morpholinoethyl)carbamoyl)benzoyl chloride (130 mg, 0.42 mmol, 1.20 equiv) in dichloromethane (10 mL) with stirring at 0-5° C. The resulting solution was stirred for 3 h at room temperature. The resulting solution was diluted with 30 mL of dichloromethane. The resulting mixture was washed with 1×20 mL of NH$_4$Cl and 2×20 mL of brine, dried over anhydrous sodium sulfate, and concentrated under vacuum. The crude product (200 mg) was purified by reverse phase HPLC eluting with a water/CH$_3$CN gradient containing 0.05% TFA. The product was obtained as 36.7 mg (15%) of a yellow solid. $^1$H-NMR (400 MHz, DMSO, ppm): δ 11.43-11.33(m, 2H), 9.70(s, 1H), 9.43(s, 1H), 8.77(s, 1H), 8.26-8.18 (m, 3H), 8.06-7.93 (m, 2H), 7.86-7.79(m, 2H), 7.68-7.62(m, 2H), 7.52 (s, 1H), 7.30-7.28(d, J=6.9 Hz, 1H), 4.59-4.57(m, 1H), 4.18-3.83(m, 27H), 3.44(s, 3H), 3.27-3.26 (m, 5H), 3.18 (s, 3H), 2.96(s, 4H), 1.69(s, 4H), 1.59-1.52(m, 3H). MS (ES, m/z): 705 [M+H]$^+$.

Example 3

N1-Methyl-N1-(2-morpholinoethyl)-N3-(4-(piperidin-1-yl)-2-((4-(3-(trifluoromethyl)phenyl)thiazol-2-yl)carbamoyl)phenyl)isophthalamide Scheme 3. 1. Br$_2$, ether; 2. MeOH, thiourea; 3. DIPEA, DCM, 5-chloro-2-nitrobenzoyl chloride; 4. K$_2$CO$_3$, MeOH; 5. DMF, piperidine; 6. H$_2$, Pd/C, MeOH; 7. DCM, pyridine intermediate 1f.

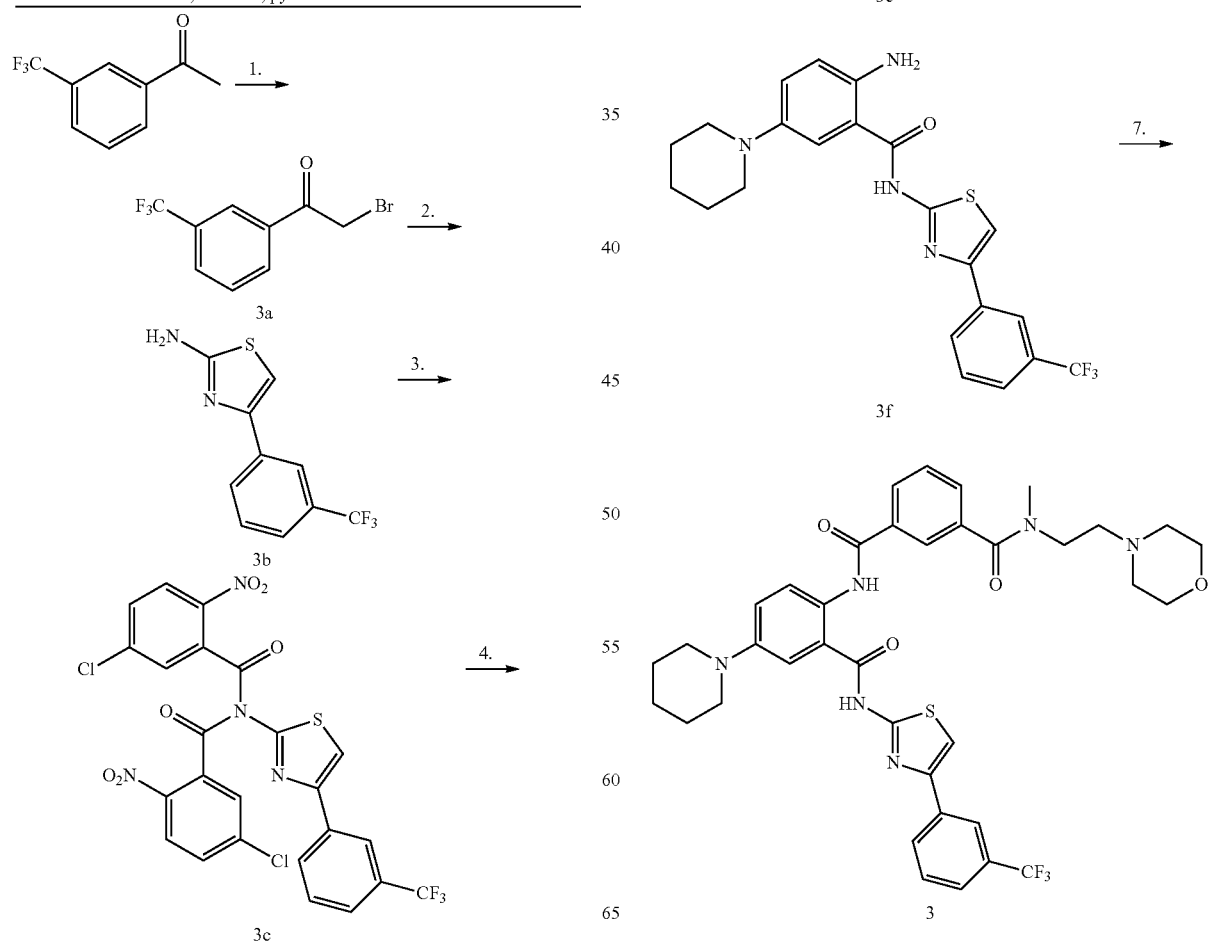

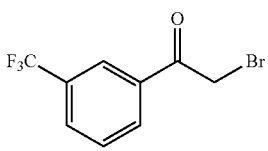 [SMILES: O=C(CBr)c1cccc(C(F)(F)F)c1]

Intermediate 3a 2-bromo-1-(3-(trifluoromethyl)phenyl)ethanone

Into a 250-mL round bottom flask, was placed a solution of 1-(3-(trifluoromethyl)phenyl)ethanone (5 g, 26.57 mmol, 1.00 equiv) in ether (80 mL). To this was added dropwise a solution of Br$_2$ (4.26 g, 26.66 mmol, 1.00 equiv) in ether (20 mL) with stirring over 1 hr and the resulting solution was stirred an additional 1 h at room temperature. The mixture was washed with 2×30 mL of NaHSO$_3$ and 1×30 mL of brine, then dried over anhydrous sodium sulfate and concentrated under vacuum to give 5.2 g (crude) of 2-bromo-1-(3-(trifluoromethyl)phenyl)ethanone as yellow oil.

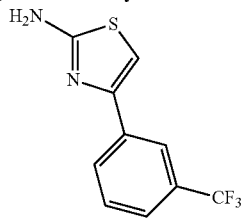

Intermediate 3b 5-(3-(trifluoromethyl)phenyl)thiazol-2-amine

Into a 100-mL round bottom flask, was placed a solution of 2-bromo-1-(3-(trifluoromethyl)phenyl)ethanone (2.5 g, 9.40 mmol, 1.00 equiv) in methanol (50 mL), and thiourea (710 mg, 9.33 mmol, 1.00 equiv). The resulting solution was stirred overnight at 75° C. in an oil bath. The reaction mixture was cooled with a water/ice bath. The solids were collected by filtration. The residue was dissolved in 200 mL of ethyl acetate. The resulting mixture was washed with 1×50 mL of sodium hydroxide (1 N) and 2×50 mL of brine, dried over anhydrous sodium sulfate, and concentrated under vacuum. This resulted in 2.2 g (96%) of 5-(3-(trifluoromethyl)phenyl) thiazol-2-amine as a white solid.

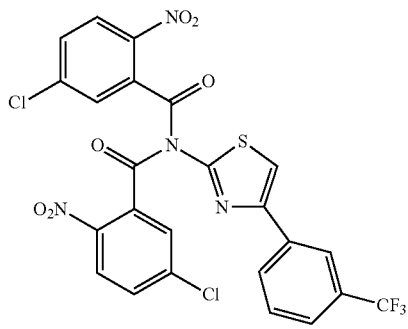 [SMILES: O=C(c1cc(Cl)ccc1[N+](=O)[O-])N(C(=O)c1cc(Cl)ccc1[N+](=O)[O-])c1nc(-c2cccc(C(F)(F)F)c2)cs1]

Intermediate 3c 5-chloro-N-(5-chloro-2-nitrobenzoyl)-2-nitro-N-(4-(3-(trifluoromethyl)-phenyl)thiazol-2-yl)benzamide Into a 100-mL round bottom flask, was placed a solution of 5-(3-(trifluoromethyl)phenyl)thiazol-2-amine (2 g, 8.19 mmol, 1.00 equiv) in dichloromethane (20 mL), and diisopropylethylamine (4.22 g, 32.65 mmol, 4.00 equiv). This was followed by dropwise addition of a solution of 5-chloro-2-nitrobenzoyl chloride (3.967 g, 18.03 mmol, 2.20 equiv) in dichloromethane (10 mL) with stirring. The resulting solution was stirred for 4 h at room temperature. The resulting solution was diluted with 50 mL of ethyl acetate. The resulting mixture was washed with 2×20 mL of brine, dried over anhydrous sodium sulfate, and concentrated under vacuum. This resulted in 4.5 g (90%) of product as a yellow oil.

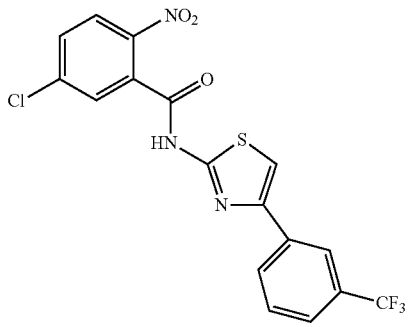 [SMILES: O=C(Nc1nc(-c2cccc(C(F)(F)F)c2)cs1)c1cc(Cl)ccc1[N+](=O)[O-]]

Intermediate 3d 5-chloro-2-nitro-N-(5-(3-(trifluoromethyl)phenyl) thiazol-2-yl)benzamide Into a 100-mL round bottom flask, was placed a solution of 5-chloro-N-(5-chloro-2-nitrobenzoyl)-2-nitro-N-(4-(3-(trifluoromethyl)phenyl)thiazol-2-yl)benzamide (4.5 g, 7.36 mmol, 1.00 equiv) in methanol (50 mL), and potassium carbonate (3.05 g, 22.07 mmol, 3.00 equiv). The resulting solution was stirred for 4 h at 40° C. in an oil bath. The resulting solution was diluted with 200 mL of ethyl acetate. The resulting mixture was washed with 2×50 mL of brine, dried over anhydrous sodium sulfate, and concentrated under vacuum. This resulted in 2.6 g (83%) of product as a yellow solid.

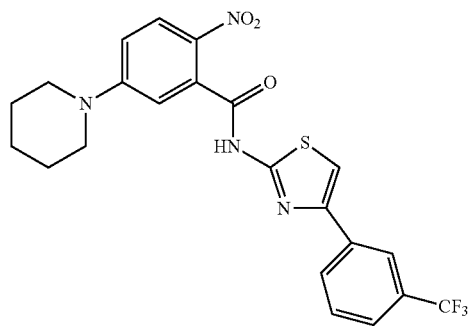 [SMILES: Nc1ccc(N2CCCCC2)cc1C(=O)Nc1nc(-c2cccc(C(F)(F)F)c2)cs1]

Intermediate 3e

2-nitro-5-(piperidin-1-yl)-N-(5-(3-(trifluoromethyl) phenyl)thiazol-2-yl)-benzamide To a solution of 5-chloro-2-nitro-N-(5-(3-(trifluoromethyl)phenyl)thiazol-2-yl)benzamide (2.6 g, 6.08 mmol, 1.00 equiv) in N,N-dimethylformamide (20 mL) was added and piperidine (20 mL) and the resulting solution was stirred for 3 h at 100° C. in an oil bath. The mixture was diluted with 200 mL of ethyl acetate, washed with 2×50 mL of brine, dried over anhydrous sodium sulfate and then concentrated under vacuum to give 2.2 g (76%) of product as a yellow solid.

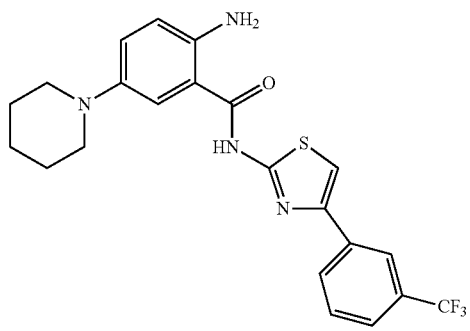

Intermediate 3f

2-amino-5-(piperidin-1-yl)-N-(5-(3-(trifluoromethyl) phenyl)thiazol-2-yl)-benzamide Into a 100-mL round bottom flask, was placed a solution of 2-nitro-5-(piperidin-1-yl)-N-(5-(3-(trifluoromethyl)phenyl)thiazol-2-yl)benzamide (2.2 g, 4.62 mmol, 1.00 equiv) in methanol (30 mL). The solution was treated with Pd/C (2 g, 10%), and stirred under an atmosphere of hydrogen for 2 h at room temperature. The solids were filtered out. The resulting mixture was concentrated under vacuum. The residue was applied onto a silica gel column and eluted with petroleum ether/ethyl acetate (7:1). This resulted in 1.2 g (58%) of product as a yellow solid.

Example 3

N1-methyl-N1-(2-morpholinoethyl)-N3-(4-(piperidin-1-yl)-2-((4-(3-(trifluoromethyl)phenyl)thiazol-2-yl)carbamoyl)phenyl)isophthalamide Into a 50-mL round bottom flask, was placed a solution of 2-amino-5-(piperidin-1-yl)-N-(4-(3-(trifluoromethyl)phenyl)thiazol-2-yl)benzamide (287 mg, 0.64 mmol, 1.00 equiv) in dichloromethane (3 mL), and pyridine (406 mg, 5.13 mmol, 8.00 equiv). This was followed by dropwise addition of a solution of 3-(methyl(2-morpholinoethyl)carbamoyl) benzoyl chloride (300 mg, 0.97 mmol, 1.50 equiv) in dichloromethane (2 mL) with stirring. The resulting solution was stirred for 1 h at room temperature, then diluted with 50 mL of ethyl acetate. The resulting mixture was washed with 1×20 mL of hydrogen chloride (1 N) and 2×20 mL of brine. The mixture was dried over anhydrous sodium sulfate and concentrated under vacuum. The crude product (300 mg) was purified by reverse phase HPLC eluting with a water/$CH_3CN$ gradient containing 0.05% TFA. The product was obtained as 120 mg (20%) of as a yellow solid. $^1$H-NMR (300 MHz, DMSO, ppm): δ 12.89(s, 1H), 10.93(s, 1H), 9.79(s, 1H), 8.26 (m, 2H), 8.00(m, 4H), 7.69(m, 4H), 7.53(s, 1H), 7.27(d, J=8.7 Hz, 1H), 4.01(s, 2H), 3.85(s, 2H), 3.63(s, 4H), 3.44(s, 2H), 3.17(m, 6H), 2.99(s, 3H), 1.70(m, 6H). MS (ES, m/z): 721 [M+H]$^+$.

Example 4

3-((3-((4-Chloro-2-((1-(3,4-dimethylphenyl)-1H-pyrazol-3-yl)carbamoyl)phenyl)carbamoyl)benzyl) thio)propanoic acid Scheme 4. 1. KSAc, MeOH: 2. $K_2CO_3$; 3. tert-butyl acrylate, DBU; 4. oxalyl chloride, DMF; 5. 3,4-dimethylbromobenzene, CuI, L-proline, $K_2CO_3$; 6. $H_2$, Pd/C; 7. 2-nitro-5-chlorobenzoyl chloride, pyridine; 8. Zn, AcOH; 9. intermediate 4d, pyridine; DCM; 10. DCM, TFA.

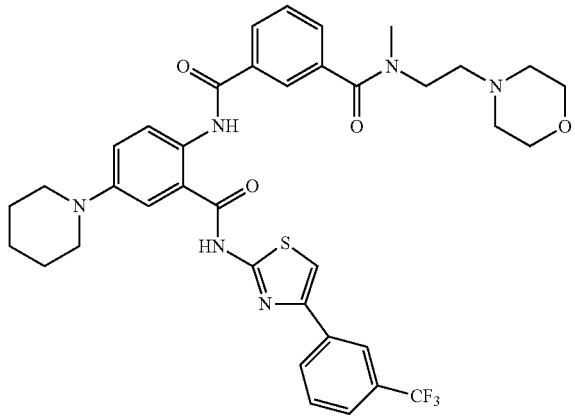 [SMILES: CN(CCN1CCOCC1)C(=O)c1cccc(C(=O)Nc2ccc(N3CCCCC3)cc2C(=O)Nc2nc(-c3cccc(C(F)(F)F)c3)cs2)c1]

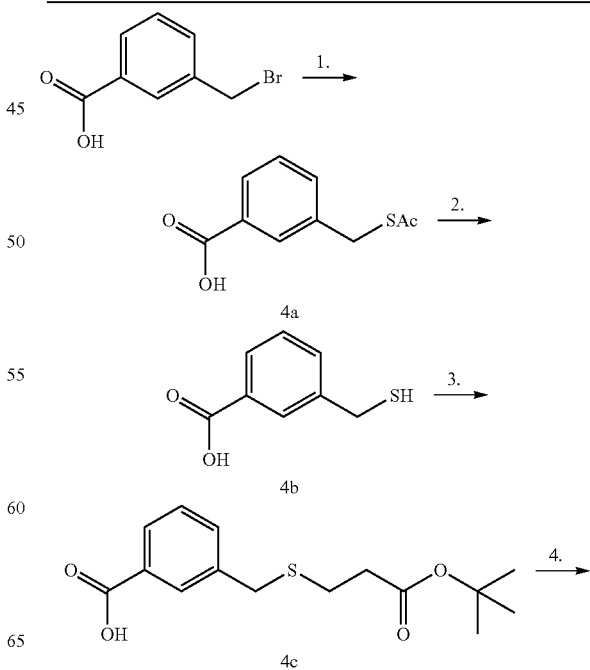

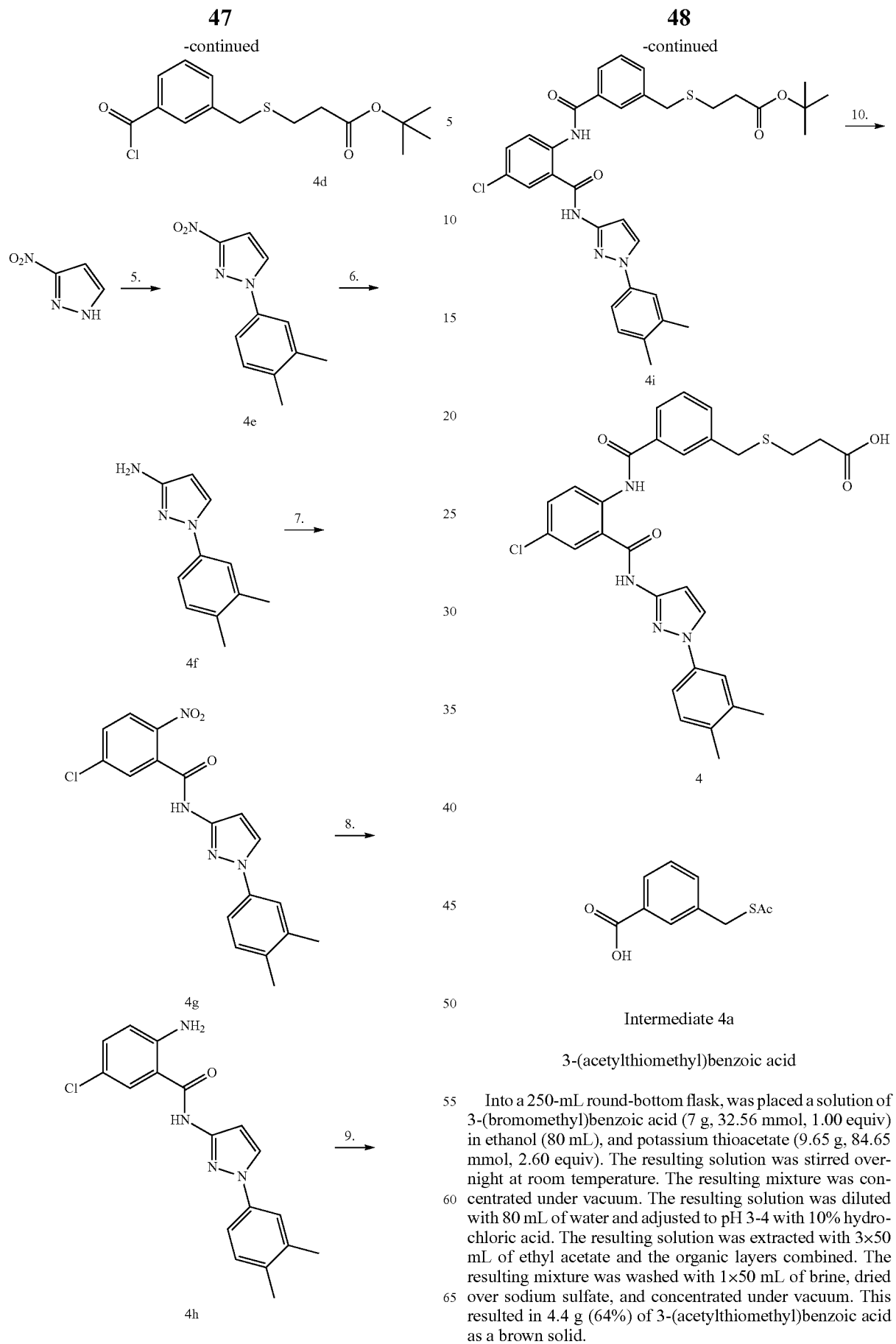

Intermediate 4a 3-(acetylthiomethyl)benzoic acid

Into a 250-mL round-bottom flask, was placed a solution of 3-(bromomethyl)benzoic acid (7 g, 32.56 mmol, 1.00 equiv) in ethanol (80 mL), and potassium thioacetate (9.65 g, 84.65 mmol, 2.60 equiv). The resulting solution was stirred overnight at room temperature. The resulting mixture was concentrated under vacuum. The resulting solution was diluted with 80 mL of water and adjusted to pH 3-4 with 10% hydrochloric acid. The resulting solution was extracted with 3×50 mL of ethyl acetate and the organic layers combined. The resulting mixture was washed with 1×50 mL of brine, dried over sodium sulfate, and concentrated under vacuum. This resulted in 4.4 g (64%) of 3-(acetylthiomethyl)benzoic acid as a brown solid.

Intermediate 4b

3-(mercaptomethyl)benzoic acid

Into a 500-mL round-bottom flask, was placed a solution of 3-(acetylthiomethyl)benzoic acid (16.4 g, 78.10 mmol, 1.00 equiv) in methanol (150 mL), and a solution of potassium carbonate (26.9 g, 194.93 mmol, 2.50 equiv) in water (70 mL). The resulting solution was stirred for 4 h at 60° C. The resulting mixture was concentrated under vacuum. The resulting solution was diluted with 200 mL of water and adjusted to pH 3 with 10% hydrochloric acid. The resulting solution was extracted with 3× (100/20 mL) of ethyl acetate/tetrahydrofuran and the organic layers combined. The resulting mixture was washed with 1×100 mL of brine, dried over sodium sulfate, and concentrated under vacuum. This resulted in 12 g (91%) of 3-(mercaptomethyl)benzoic acid as a brown solid.

Intermediate 4c

3-((3-tert-butoxy-3-oxopropylthio)methyl)benzoic acid

Into a 500-mL round bottom flask, was placed a solution of 3-(mercaptomethyl)benzoic acid (12 g, 71.43 mmol, 1.00 equiv) in acetonitrile (200 mL), tert-butyl acrylate (60 mL), and DBU (21.7 g, 142.76 mmol, 2.00 equiv). The resulting solution was stirred overnight at 80° C. in an oil bath. The resulting mixture was concentrated under vacuum. The resulting solution was diluted with 200 mL of water and adjusted to pH 2-3 with 10% hydrochloric acid. The resulting solution was extracted with 3×200 mL of ethyl acetate and the organic layers combined. The mixture was dried over anhydrous sodium sulfate and concentrated under vacuum. The residue was applied onto a silica gel column and eluted with petroleum ether/ethyl acetate (50:1) to give 10.5 g (47%) of 3-((3-tert-butoxy-3-oxopropylthio)methyl)benzoic acid as red oil. $^1$H-NMR (300 MHz, CDCl$_3$, ppm): δ 8.08 (s, 1H), 8.04 (d, J=7.8 Hz, 1H), 7.62 (d, J=7.8 Hz, 1H), 7.46 (t, 1H), 3.81 (s, 2H), 2.68 (t, 2H), 2.50 (t, 2H), 1.48 (s, 9H). MS (ES, m/z): 295 [M−H]$^-$.

Intermediate 4d tert-butyl 3-((3-(chlorocarbonyl)benzyl)thio)propanoate

Into a 100-mL round bottom flask, was placed a solution of 3-((3-tert-butoxy-3-oxopropylthio)methyl)benzoic acid 1.1c (3.00 g, 10.14 mmol, 1.00 equiv) in dichloromethane (50 mL). This was followed by dropwise addition of oxalyl dichloride (4.50 g, 35.43 mmol, 3.00 equiv) with stirring at 0° C. To this was added N,N-dimethylformamide (1 drop). The resulting solution was stirred for 1.5 h at room temperature. The resulting mixture was concentrated under vacuum to yield 3.18 g (99%) of tert-butyl 3-(3-(chlorocarbonyl)benzylthio)propanoate as red oil.

Intermediate 4e

1-(3,4-dimethylphenyl)-3-nitro-1H-pyrazole

Into a 250-mL round bottom flask purged and maintained with an inert atmosphere of nitrogen, was placed a solution of 3-nitro-1H-pyrazole (6 g, 53.10 mmol, 1.00 equiv) in DMSO (80 mL), 4-bromo-1,2-dimethylbenzene (11.8 g, 64.13 mmol, 1.21 equiv), CuI (1.6 g, 8.42 mmol, 0.16 equiv), L-proline (1 g, 8.70 mmol, 0.16 equiv), and potassium carbonate (14.6 g, 105.80 mmol, 1.99 equiv). The resulting solution was stirred overnight at 85° C. in an oil bath. The reaction progress was monitored by LCMS. The resulting solution was diluted with 300 mL of water. The resulting solution was extracted with 4×100 mL of ethyl acetate and the organic layers combined. The resulting mixture was washed with 3×100 mL of water and 1×100 mL of brine. The mixture was dried over anhydrous sodium sulfate. The solids were filtered out. The resulting mixture was concentrated under vacuum. The residue was applied onto a silica gel column and eluted with ethyl acetate/petroleum ether (1:10) to give 1 g (9%) of 1-(3,4-dimethylphenyl)-3-nitro-1H-pyrazole as a yellow solid.

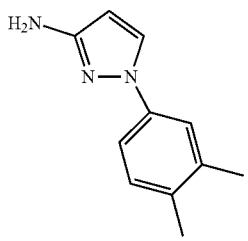 [SMILES: Cc1ccc(-n2ccc([N+](=O)[O-])n2)cc1C]

Intermediate 4f 1-(3,4-dimethylphenyl)-1H-pyrazol-3-amine

Into a 100-mL round bottom flask, was placed a solution of 1-(3,4-dimethylphenyl)-3-nitro-1H-pyrazole (900 mg, 4.15 mmol, 1.00 equiv) in methanol/ethyl acetate (20/10 mL). The solution was treated with Pd/C (500 mg) and stirred under an atmosphere of hydrogen overnight at room temperature. The reaction progress was monitored by LCMS. The solids were filtered out. The resulting mixture was concentrated under vacuum to yield 750 mg (97%) of 1-(3,4-dimethylphenyl)-1H-pyrazol-3-amine as a yellow solid.

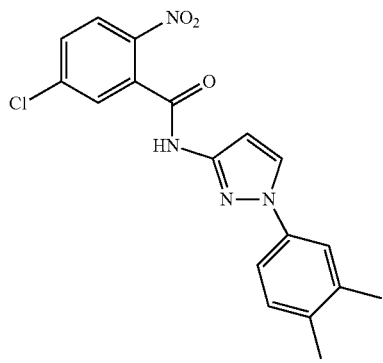

Intermediate 4g 5-chloro-N-(1-(3,4-dimethylphenyl)-1H-pyrazol-3-yl)-2-nitrobenzamide Into a 100-mL round bottom flask, was placed a solution of 1-(3,4-dimethylphenyl)-1H-pyrazol-3-amine (408 mg, 2.18 mmol, 1.00 equiv) in dichloromethane (10 mL), pyridine (518 mg, 6.56 mmol, 3.00 equiv), and 5-chloro-2-nitrobenzoyl chloride (575 mg, 2.61 mmol, 1.00 equiv). The resulting solution was stirred for 2 h at room temperature. The resulting mixture was concentrated under vacuum. The solution was adjusted to pH 7 with hydrochloric acid (1 mol/L). The resulting solution was extracted with 3×50 mL of ethyl acetate and the organic layers combined dried over anhydrous sodium sulfate, and concentrated under vacuum. This resulted in 600 mg (59%) of 5-chloro-N-(1-(3,4-dimethylphenyl)-1H-pyrazol-3-yl)-2-nitrobenzamide as a yellow solid.

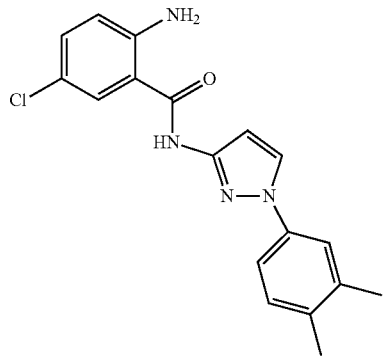 [SMILES: Cc1ccc(-n2ccc(NC(=O)c3cc(Cl)ccc3[N+](=O)[O-])n2)cc1C]

Intermediate 4h 2-amino-5-chloro-N-(1-(3,4-dimethylphenyl)-1H-pyrazol-3-yl)-benzamide Into a 100-mL round bottom flask, was placed a solution of 5-chloro-N-(1-(3,4-dimethylphenyl)-1H-pyrazol-3-yl)-2-nitrobenzamide (300 mg, 0.81 mmol, 1.00 equiv) in acetic acid (10 mL), and zinc (527 mg, 8.11 mmol, 9.96 equiv). The resulting solution was stirred for 1 h at 70° C. The resulting mixture was concentrated under vacuum. The solution was adjusted to pH 8 with ammonia (2 mol/L). The resulting solution was extracted with 4×50 mL of ethyl acetate and the organic layers combined, dried over anhydrous sodium sulfate, and concentrated under vacuum. The product was obtained as 200 mg (73%) of a solid.

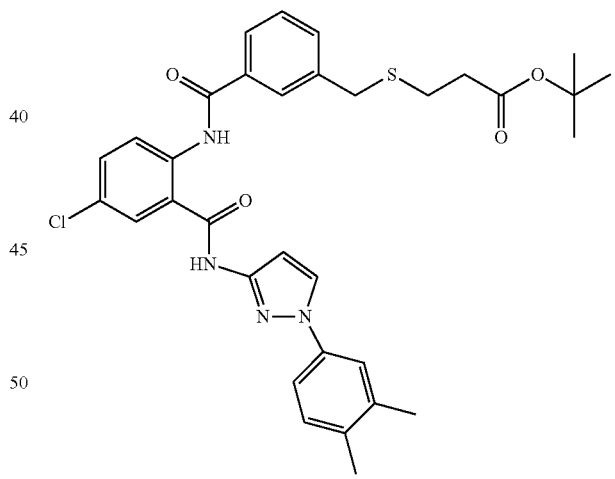

Intermediate 4i tert-butyl 3-(3-(4-chloro-2-(1-(3,4-dimethylphenyl)-1H-pyrazol-3-yl-carbamoyl)phenylcarbamoyl)benzylthio)propanoate Into a 50-mL round bottom flask, was placed a solution of tert-butyl 3-(3-(chlorocarbonyl)benzylthio)propanoate (185 mg, 0.59 mmol, 1.00 equiv) in dichloromethane (10 mL), and pyridine (140 mg, 1.77 mmol, 3.00 equiv). This was followed by dropwise addition of a solution of 2-amino-5-chloro-N-(1-(3,4-dimethylphenyl)-1H-pyrazol-3-yl)benzamide (200 mg, 0.59 mmol, 1.00 equiv) in dichloromethane (2 mL) with stirring. The resulting solution was stirred for 1 h at room temperature. The resulting mixture was concentrated under vacuum. The residue was applied onto a silica gel column and eluted with petroleum ether/ethyl acetate (10:1) to yield 150 mg (33%) of product as a yellow solid.

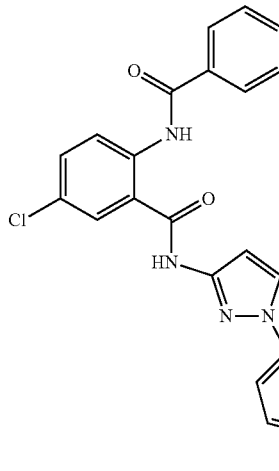

Example 4

3-(3-(4-chloro-2-(1-(3,4-dimethylphenyl)-1H-pyrazol-3-ylcarbamoyl)-phenylcarbamoyl)benzylthio) propanoic acid Into a 50-mL round bottom flask, was placed a solution of tert-butyl 3-(3-(4-chloro-2-(1-(3,4-dimethylphenyl)-1H-pyrazol-3-ylcarbamoyl)phenylcarbamoyl)benzylthio)propanoate (150 mg, 0.24 mmol, 1.00 equiv) in dichloromethane (4 mL), and 2,2,2-trifluoroacetic acid (2 mL). The resulting solution was stirred for 2 h at room temperature. The resulting mixture was concentrated under vacuum. The crude product (100 mg) was purified by reverse phase HPLC eluting with a water/CH$_3$CN gradient containing 0.05% TFA. The product was obtained as 36.3 mg (27%) of a white solid. $^1$H-NMR (300 MHz, DMSO, ppm): δ 11.82(s, 1H), 11.48(s, 1H), 8.52 (d, J=8.70 Hz, 1H), 8.41(s, 1H), 8.11(s, 1H), 7.92(s, 1H), 7.79(m, 1H), 7.67(m, 1H), 7.57(m, 4H), 7.26(m, 1H), 6.92(d, J=1.8 Hz, 1H), 3.86(s, 2H), 2.60(m, 2H), 2.29(m, 6H). MS (ES, m/z): 563 [M+H]$^+$.

Example 5

3-((3-((2-((1-(3,4-Dimethylphenyl)-1H-pyrazol-3-yl)carbamoyl)-4-(piperidin-1-yl)phenyl)carbamoyl)benzyl)thio)propanoic acid Scheme 5. 1. K$_2$CO$_3$, DMF, piperidine; 2. Zn, HOAc; 3. EDC·HCl, DCM, DMAP, intermediate 4C; 4. DCM, TFA.

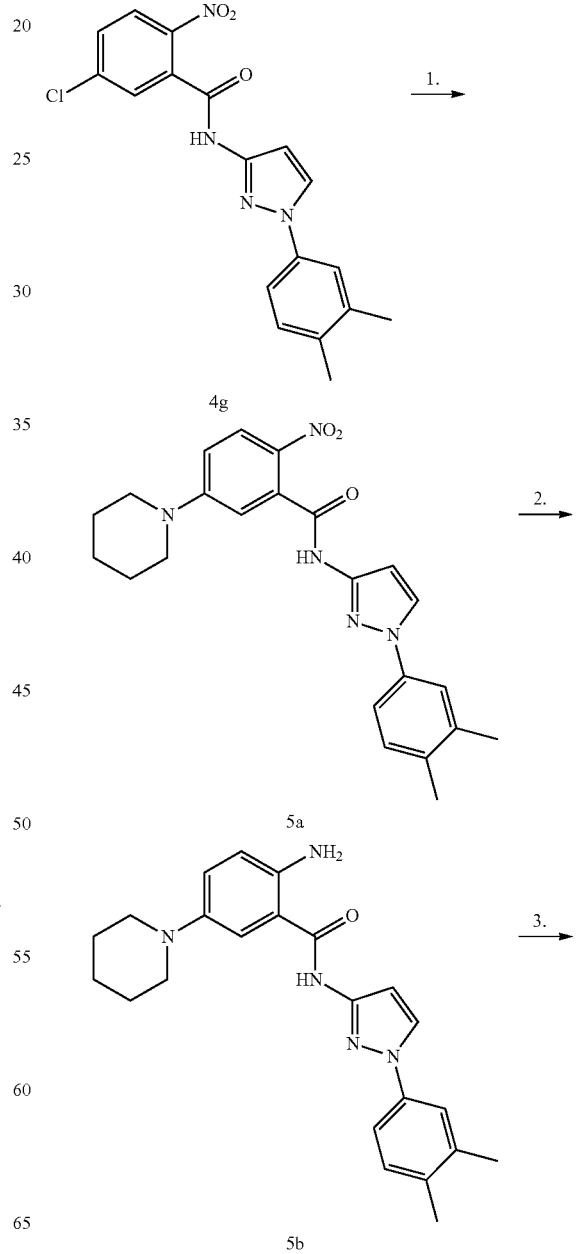

-continued

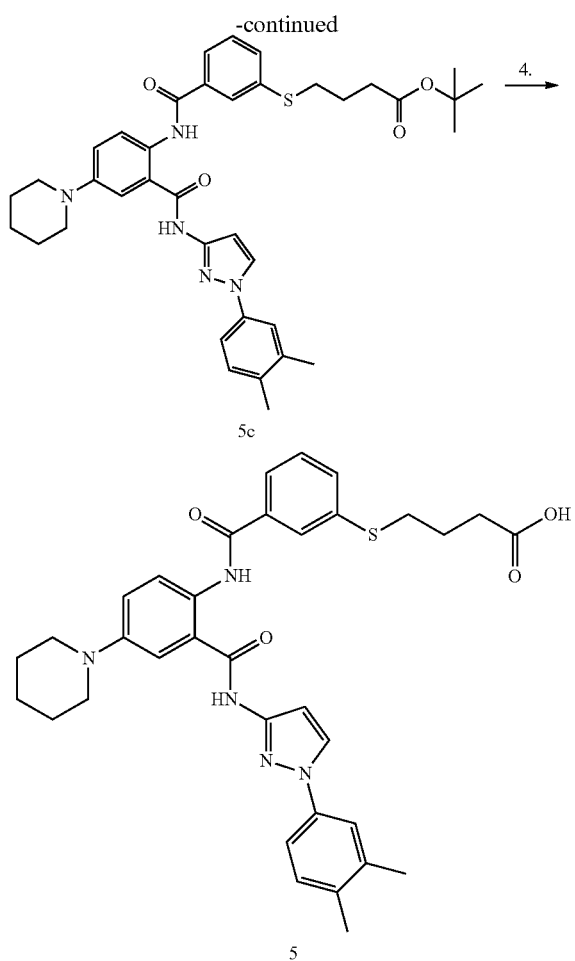

5c

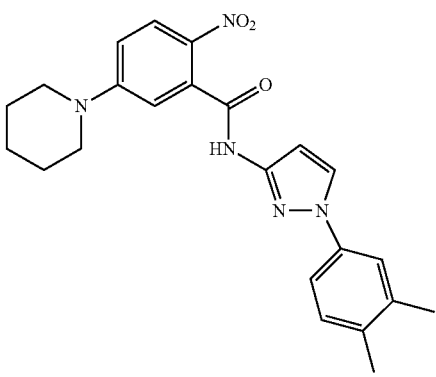 [SMILES: Cc1ccc(-n2ccc(NC(=O)c3cc(N4CCCCC4)ccc3N)n2)cc1C]

Intermediate 5a

N-(1-(3,4-dimethylphenyl)-1H-pyrazol-3-yl)-2-nitro-5-(piperidin-1-yl)-benzamide

Into a 50-mL round bottom flask, was placed a solution of 5-chloro-N-(1-(3,4-dimethylphenyl)-1H-pyrazol-3-yl)-2-nitrobenzamide 4g (300 mg, 0.81 mmol, 1.00 equiv) in N,N-dimethylformamide (10 mL), potassium carbonate (330 mg, 2.39 mmol, 3.00 equiv), and piperidine (200 mg, 2.35 mmol, 3.00 equiv). The resulting solution was stirred for 4 h at 110° C. The resulting mixture was concentrated under vacuum. The residue was dissolved in 50 mL of ethyl acetate. The resulting mixture was washed with 2×30 mL of brine, dried over sodium sulfate, and concentrated under vacuum. This resulted in 300 mg (88%) of product as a yellow solid.

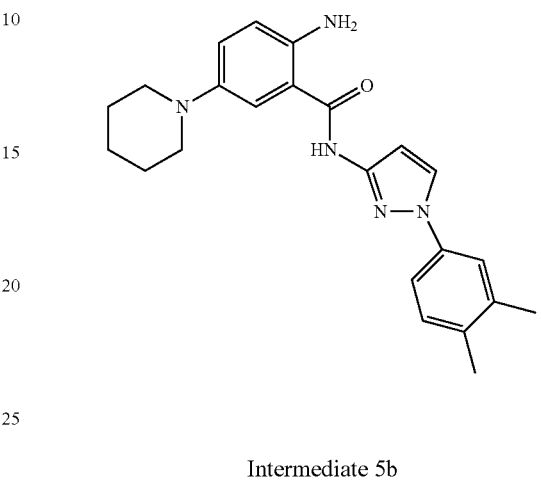

Intermediate 5b 2-amino-N-(1-(3,4-dimethylphenyl)-1H-pyrazol-3-yl)-5-(piperidin-1-yl)-benzamide Into a 50-mL round bottom flask, was placed a solution of N-(1-(3,4-dimethylphenyl)-1H-pyrazol-3-yl)-2-nitro-5-(piperidin-1-yl)benzamide (400 mg, 0.95 mmol, 1.00 equiv) in acetic acid (8 mL), and zinc (600 mg, 9.23 mmol, 9.96 equiv). The resulting solution was stirred for 1 h at 70° C. The solids were filtered out. The resulting mixture was concentrated under vacuum. The solution was adjusted to pH 8 with ammonia (2 mol/L). The resulting solution was extracted with 2×50 mL of ethyl acetate and the organic layers combined, dried over anhydrous sodium sulfate, and concentrated under vacuum. This resulted in 300 mg (81%) of 2-amino-N-(1-(3,4-dimethylphenyl)-1H-pyrazol-3-yl)-5-(piperidin-1-yl)benzamide as a green solid.

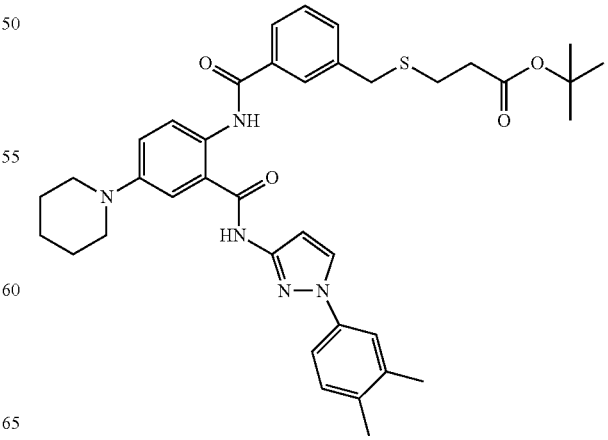

Intermediate 5c tert-butyl 3-(3-(2-(1-(3,4-dimethylphenyl)-1H-pyrazol-3-ylcarbamoyl)-4-(piperidin-1-yl)phenylcarbamoyl)benzylthio)propanoate Into a 100-mL round bottom flask, was placed a solution of 3-((3-tert-butoxy-3-oxopropylthio)methyl)benzoic acid (167 mg, 0.56 mmol, 1.10 equiv) in dichloromethane (10 mL), EDC.HCl (148 mg, 0.77 mmol, 1.50 equiv), 4-dimethylaminopyridine (95 mg, 0.77 mmol, 1.50 equiv), and 2-amino-N-(1-(3,4-dimethylphenyl)-1H-pyrazol-3-yl)-5-(piperidin-1-yl)benzamide (200 mg, 0.51 mmol, 1.00 equiv). The resulting solution was stirred for 4 h at room temperature. The resulting mixture was concentrated under vacuum. The residue was applied onto a silica gel column and eluted with petroleum ether/ethyl acetate (10:1) to yield 150 mg (44%) of product as a green solid.

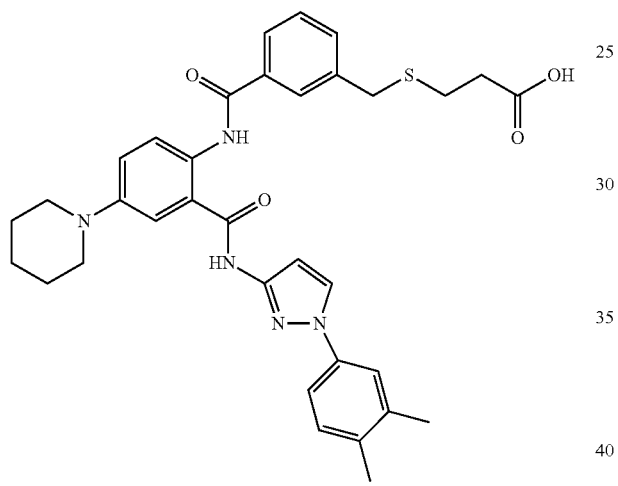

Example 5

3-(3-(2-(1-(3,4-dimethylphenyl)-1H-pyrazol-3-ylcarbamoyl)-4-(piperidin-1-yl)phenylcarbamoyl)benzylthio)propanoic acid Into a 50-mL round bottom flask, was placed a solution of tert-butyl 3-(3-(2-(1-(3,4-dimethylphenyl)-1H-pyrazol-3-ylcarbamoyl)-4-(piperidin-1-yl)phenylcarbamoyl)benzylthio)propanoate (150 mg, 0.22 mmol, 1.00 equiv) in dichloromethane (4 mL), and trifluoroacetic acid (2 mL). The resulting solution was stirred for 2 h at room temperature. The resulting mixture was concentrated under vacuum. The crude product (100 mg) was purified by reverse phase HPLC eluting with a water/$CH_3CN$ gradient containing 0.05% TFA. The product was obtained as 85.3 mg (62%) of a white solid. $^1$H-NMR (300 MHz, DMSO, ppm): δ 11.70(s, 1H), 11.44(s, 1H), 8.41(m, 2H), 7.91(s, 1H), 7.78(m, 1H), 7.68(m, 1H), 7.62(m, 1H), 7.58(m, 3H), 7.40(m, 1H), 7.23(m, 1H), 6.92(s, 1H), 3.86(s, 2H), 3.36(m, 4H), 2.62(m, 2H), 2.29(m, 6H), 1.60(m, 6H). MS (ES, m/z): 612 [M+H]$^+$.

Example 6

3-((3-((4-Chloro-2-((1-(3-(trifluoromethyl)phenyl)-1H-pyrazol-3-yl)carbamoyl)phenyl)carbamoyl)benzyl)thio)propanoic acid Scheme 6. 1. 3-(trifluoromethyl)iodobenzene, $K_2CO_3$, CuI, L-proline; 2. $H_2$, Pd/C; 3. 2-nitro-5-chlorobenzoyl chloride, pyridine, DCM; 4. Zn, HOAc; 5. DCM, intermediate 4d, pyridine; 6. DCM, TFA.

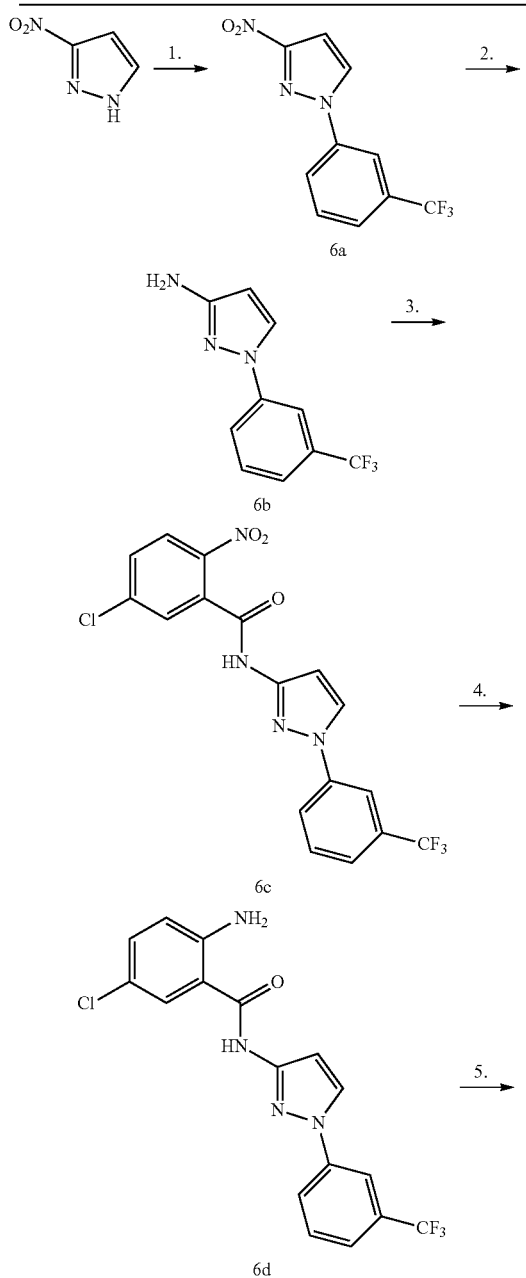

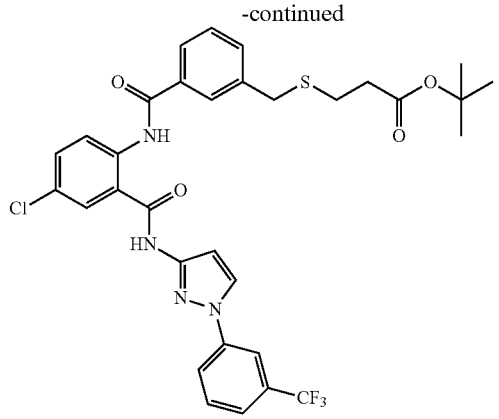

6e

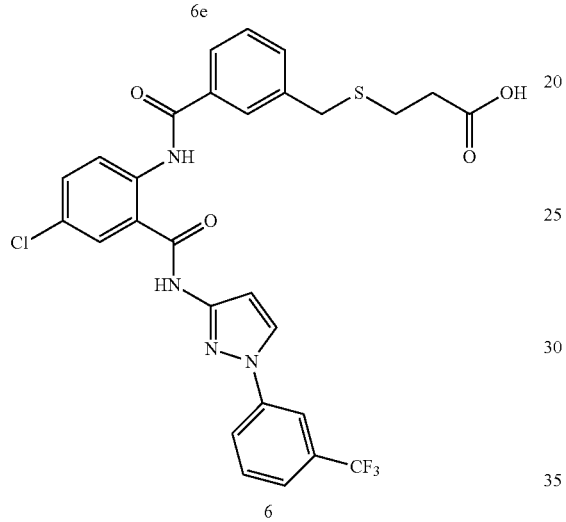

Intermediate 6a 3-nitro-1-(3-(trifluoromethyl)phenyl)-1H-pyrazole

Into a 250-mL round-bottom flask, was placed a solution of 3-nitro-1H-pyrazole (10 g, 88.50 mmol, 1.00 equiv) in DMSO (100 mL), 1-iodo-3-(trifluoromethyl)benzene (29 g, 106.62 mmol, 1.20 equiv), potassium carbonate (24 g, 173.91 mmol, 1.97 equiv), copper(I) iodide (2.6 g, 13.68 mmol, 0.15 equiv), and L-proline (2.5 g, 21.74 mmol, 0.25 equiv). The resulting solution was stirred overnight at 85° C. in an oil bath. The reaction progress was monitored by LCMS. The resulting solution was diluted with 500 mL of water, extracted with 7×200 mL of ethyl acetate and the organic layers combined. The resulting mixture was washed with 3×200 mL of water and 2×200 mL of brine. The mixture was dried over sodium sulfate. The solids were filtered out. The resulting mixture was concentrated under vacuum. The residue was applied onto a silica gel column and eluted with petroleum ether/ethyl acetate (10:1-5:1) to give 14 g (62%) of 3-nitro-1-(3-(trifluoromethyl)phenyl)-1H-pyrazole as a light yellow solid.

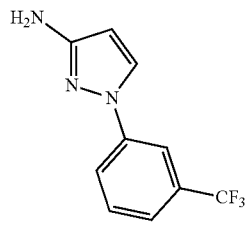 [SMILES: Nc1ccn(-c2cccc(C(F)(F)F)c2)n1]

Intermediate 6b 1-(3-(trifluoromethyl)phenyl)-1H-pyrazol-3-amine

Into a 100-mL round-bottom flask, was placed a solution of 3-nitro-1-(3-(trifluoromethyl)phenyl)-1H-pyrazole (7 g, 27.24 mmol, 1.00 equiv) in methanol (30 mL). The mixture was treated with Pd/C (3 g) and stirred under a hydrogen atmosphere overnight at room temperature. The solids were filtered out. The resulting mixture was concentrated under vacuum to yield 6 g (97%) of 1-(3-(trifluoromethyl)phenyl)-1H-pyrazol-3-amine as a white solid.

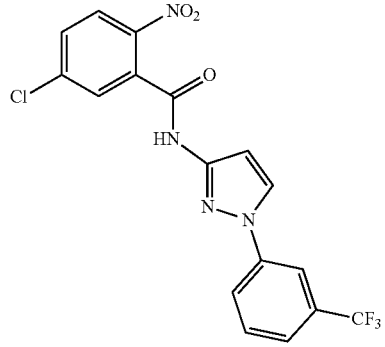 [SMILES: Nc1ccc(Cl)cc1C(=O)Nc1ccn(-c2cccc(C(F)(F)F)c2)n1]

Intermediate 6c 5-chloro-2-nitro-N-(1-(3-(trifluoromethyl)phenyl)-1H-pyrazol-3-yl)-benzamide Into a 100-mL round bottom flask, was placed a solution of 1-(3-(trifluoromethyl)phenyl)-1H-pyrazol-3-amine (520 mg, 2.29 mmol, 1.00 equiv) in dichloromethane (5 mL), pyridine (540 mg, 6.84 mmol, 3.00 equiv), and 5-chloro-2-nitrobenzoyl chloride (500 mg, 2.27 mmol, 1.00 equiv). The resulting solution was stirred for 1 h at room temperature. The resulting mixture was washed with 2×50 mL of water, dried over anhydrous sodium sulfate, and concentrated under vacuum. The residue was applied onto a silica gel column and eluted with petroleum ether/ethyl acetate (10:1). This resulted in 800 mg (85%) of product as a yellow solid.

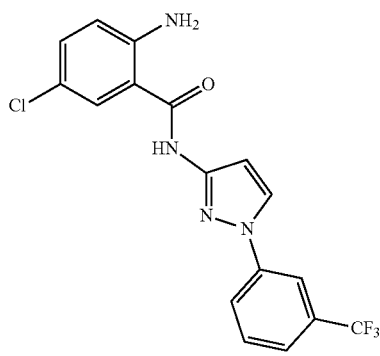

Intermediate 6d 2-amino-5-chloro-N-(1-(3-(trifluoromethyl)phenyl)-1H-pyrazol-3-yl)-benzamide Into a 100-mL round bottom flask, was placed a solution of 5-chloro-2-nitro-N-(1-(3-(trifluoromethyl)phenyl)-1H-pyrazol-3-yl)benzamide (400 mg, 0.98 mmol, 1.00 equiv) in acetic acid (5 mL), and Zn (640 mg, 9.85 mmol, 10.00 equiv). The resulting solution was stirred for 1 h at 70° C. The solids were filtered out. The resulting mixture was concentrated under vacuum. The solution was adjusted to pH 8 with ammonia (2 mol/L). The resulting solution was extracted with 2×50 mL of ethyl acetate and the organic layers combined, dried over anhydrous sodium sulfate, and concentrated under vacuum. This resulted in 300 mg (81%) of product as a yellow solid.

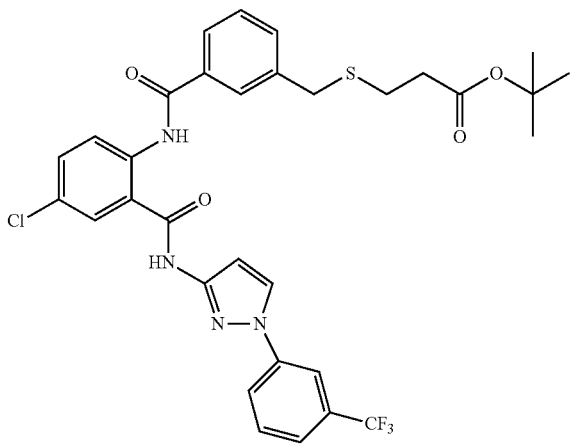 [SMILES: CC(C)(C)OC(=O)CCSCc1cccc(C(=O)Nc2ccc(Cl)cc2C(=O)Nc2ccn(-c3cccc(C(F)(F)F)c3)n2)c1]

Intermediate 6e tert-butyl 3-(3-(4-chloro-2-(1-(3-(trifluoromethyl)phenyl)-1H-pyrazol-3-ylcarbamoyl)phenylcarbamoyl)benzylthio)propanoate Into a 50-mL round bottom flask, was placed a solution of 2-amino-5-chloro-N-(1-(3-(trifluoromethyl)phenyl)-1H-pyrazol-3-yl)benzamide (191 mg, 0.50 mmol, 1.00 equiv) in dichloromethane (5 mL), pyridine (120 mg, 1.50 mmol, 3.00 equiv), and tert-butyl 3-(3-(chlorocarbonyl)benzylthio)propanoate (158 mg, 0.50 mmol, 1.00 equiv). The resulting solution was stirred for 1 h at room temperature. The resulting mixture was washed with 2×50 mL of water. The mixture was dried over sodium sulfate and concentrated under vacuum. The residue was applied onto a silica gel column and eluted with petroleum ether/ethyl acetate (20:1) to give 100 mg (30%) of product as yellow oil.

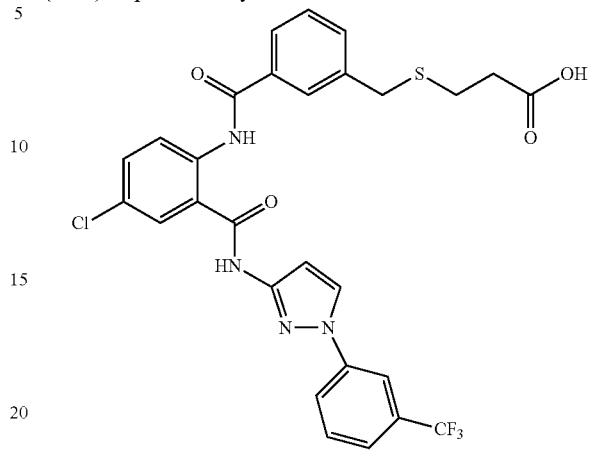

Example 6

3-(3-(4-chloro-2-(1-(3-(trifluoromethyl)phenyl)-1H-pyrazol-3-ylcarbamoyl)-phenylcarbamoyl)benzylthio)propanoic acid Into a 50-mL round bottom flask, was placed a solution of tert-butyl 3-(3-(4-chloro-2-(1-(3-(trifluoromethyl)phenyl)-1H-pyrazol-3-ylcarbamoyl)phenylcarbamoyl)benzylthio)propanoate (150 mg, 0.23 mmol, 1.00 equiv) in dichloromethane (4 mL), trifluoroacetic acid (2 mL). The resulting solution was stirred for 2 h at room temperature. The resulting mixture was concentrated under vacuum. The crude product (100 mg) was purified by reverse phase HPLC eluting with a water/CH$_3$CN gradient containing 0.05% TFA. The product was obtained as 48.9 mg (36%) of a white solid. $^1$H-NMR (300 MHz, DMSO, ppm): δ 12.21(s, 1H), 11.73(s, 1H), 11.56 (s, 1H), 8.68(m, 1H), 8.49(m, 1H), 8.10(m, 3H), 7.92(s, 1H), 7.73(m, 7H), 7.01(d, J=3 Hz, 1H), 3.86(s, 2H), 2.59(m, 2H). MS (ES, m/z): 625 [M+Na]$^+$.

Example 7

3-((3-((4-(Piperidin-1-yl)-2-((1-(3-(trifluoromethyl)phenyl)-1H-pyrazol-3-yl)carbamoyl)phenyl)carbamoyl)benzyl)thio)propanoic acid

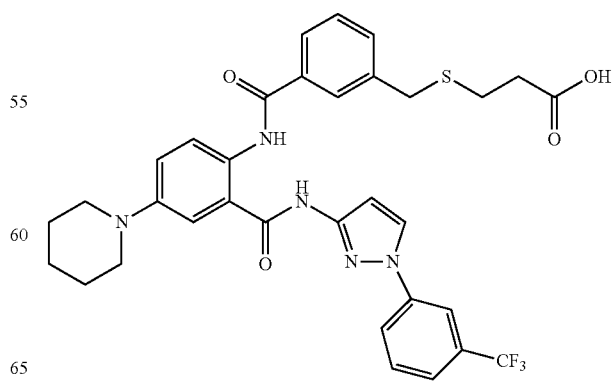

This compound was prepared from 5-chloro-2-nitro-N-(1-(3-(trifluoromethyl)phenyl)-1H-pyrazol-3-yl)benzamide 6c using the procedure described for the preparation of 3-(3-(2-(1-(3,4-dimethylphenyl)-1H-pyrazol-3-ylcarbamoyl)-4-(piperidin-1-yl)phenylcarbamoyl)-benzylthio)propanoic acid 5 from 5-chloro-N-(1-(3,4-dimethylphenyl)-1H-pyrazol-3-yl)-2-nitrobenzamide 4g. $^1$H-NMR (300 MHz, CD$_3$OD, ppm): δ 8.715(d, J=6.9 Hz, 1H), 8.390-8.397(m, 1H), 8.180 (s, 1H), 8.057-8.077(m, 1H), 8.020(s, 2H), 7.894-7.914(m, 1H), 7.679-7.719(m, 2H), 7.591-7.642(m, 2H), 7.520-7.558 (m, 1H), 7.147-7.154(m, 1H), 3.889(s, 2H), 3.614-3.640(m, 4H), 2.690-2.725(m, 2H), 2.563-2.598(m, 2H), 2.002-2.055 (m, 4H), 1.804-1.818(m, 2H). MS (ES, m/z): 652 [M+H]$^+$.

Example 9

2-Methyl-1-(6-((4-(piperidin-1-yl)-2-((1-(3-(trifluoromethyl)phenyl)-1H-pyrazol-3-yl)carbamoyl)phenyl)carbamoyl)pyridin-2-yl)-5,8,11-trioxa-2-azatetradecan-14-oic acid

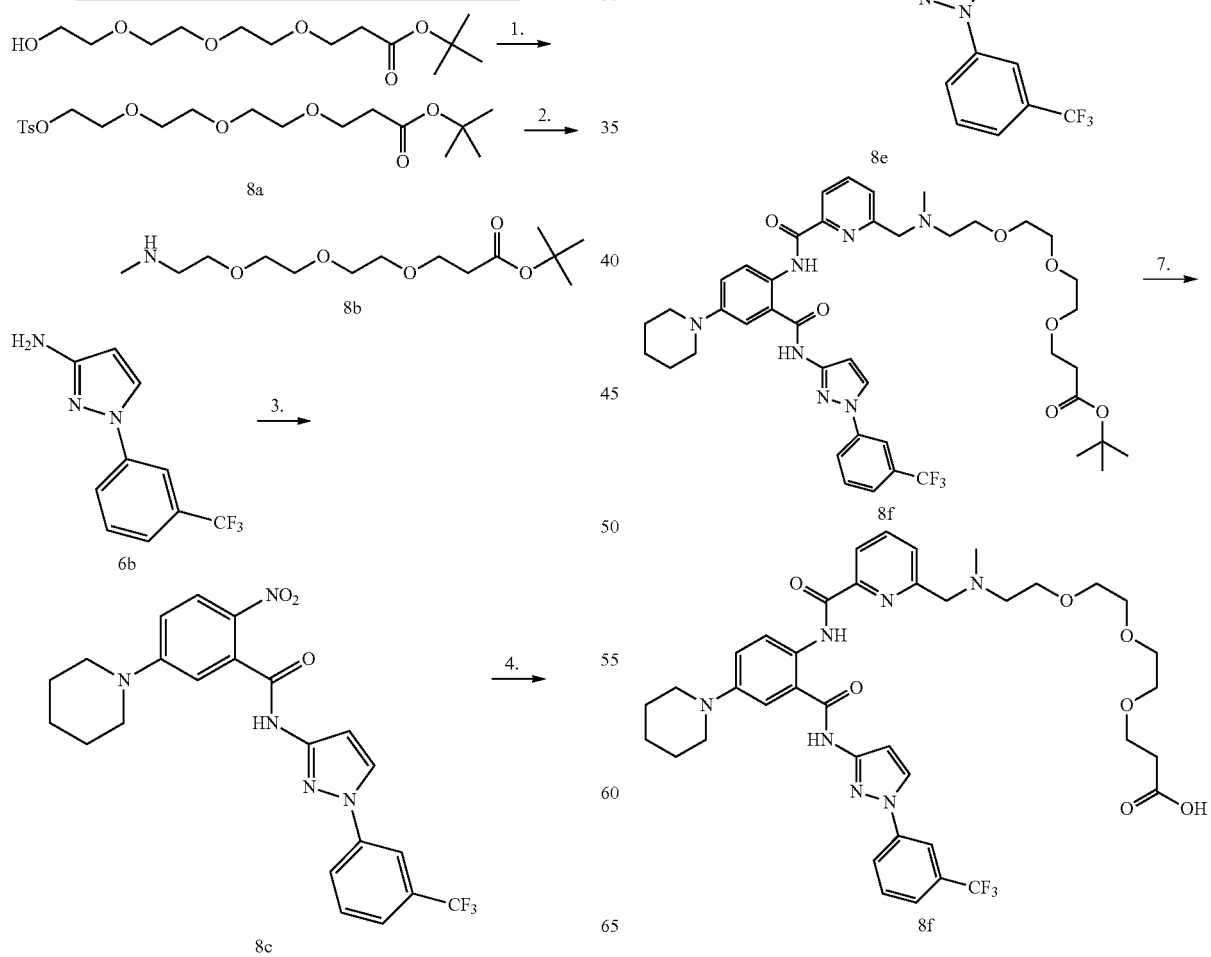

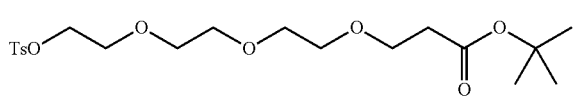 [SMILES: Cc1ccc(S(=O)(=O)OCCOCCOCCOCCC(=O)OC(C)(C)C)cc1]

Intermediate 8a tert-butyl 3-(2-(2-(2-(tosyloxy)ethoxy)ethoxy)ethoxy)propanoate

Into a 250-mL round-bottom flask, was placed a solution of tert-butyl 3-(2-(2-(2-hydroxyethoxyl)ethoxy)ethoxy)propanoate (10 g, 35.97 mmol, 1.00 equiv) in pyridine (40 mL). This was followed by the addition of toluenesulfonyl chloride (6.8 g, 35.79 mmol, 1.00 equiv), in portions at 0° C. The resulting solution was stirred for 4 h at 0° C. The resulting mixture was concentrated under vacuum. The residue was dissolved in 30 mL of dichloromethane. The resulting mixture was washed with 3×20 mL of 3% hydrochloric acid (aq) and 20 mL of brine. The mixture was dried over sodium sulfate and concentrated under vacuum to give 14 g (90%) of tert-butyl 3-(2-(2-(2-(tosyloxy)ethoxy)ethoxy)ethoxy)propanoate as yellow oil.

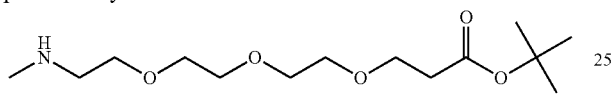

Intermediate 8b tert-butyl 3-(2-(2-(2-(methylamino)ethoxy)ethoxy)ethoxy)propanoate Into a 250-mL sealed bottle, was placed a solution of tert-butyl 3-(2-(2-(2-(tosyloxy)ethoxy)ethoxy)ethoxy)propanoate (14 g, 32.41 mmol, 1.00 equiv) in tetrahydrofuran (5 mL), and CH$_3$NH$_2$ (66.9 g, 712.16 mmol, 21.98 equiv, 33% in ethanol). The resulting solution was stirred overnight at 50° C. The resulting mixture was concentrated under vacuum. The residue was dissolved in 150 mL of dichloromethane. The resulting mixture was washed with 2×150 mL of water and 1×150 mL of brine, dried over sodium sulfate, and concentrated under vacuum. This resulted in 8.2 g (87%) of product as a yellow oil.

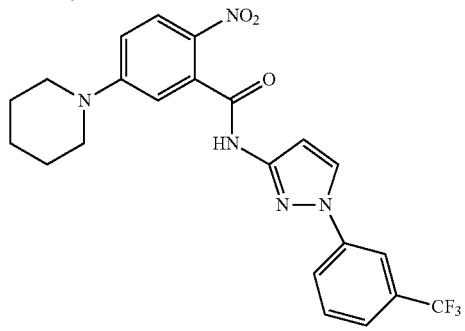 [SMILES: Nc1ccc(N2CCCCC2)cc1C(=O)Nc1ccn(-c2cccc(C(F)(F)F)c2)n1]

Intermediate 8c 2-nitro-5-(piperidin-1-yl)-N-(1-(3-(trifluoromethyl)phenyl)-1H-pyrazol-3-yl)benzamide Into a 250-mL round bottom flask, was placed a solution of 2-nitro-5-(piperidin-1-yl)benzoic acid (5 g, 20.00 mmol, 1.19 equiv) in N,N-dimethylformamide (50 mL), 1-(3-(trifluoromethyl)phenyl)-1H-pyrazol-3-amine (3.8 g, 16.74 mmol, 1.00 equiv), HATU (9.5 g, 25.00 mmol, 1.49 equiv), and N,N-diisopropylethylamine (3.3 g, 25.58 mmol, 1.53 equiv). The resulting solution was stirred overnight at 50° C. in an oil bath. The reaction progress was monitored by LCMS. The resulting solution was diluted with 200 mL of water, extracted with 4×50 mL of ethyl acetate, and the organic layers combined. The resulting mixture was washed with 2×50 mL of water and 2×50 mL of brine. The mixture was dried over sodium sulfate. The solids were filtered out. The resulting mixture was concentrated under vacuum. The residue was applied onto a silica gel column and eluted with petroleum ether/ethyl acetate (5:1) to yield 2.8 g (36%) of product as a yellow solid.

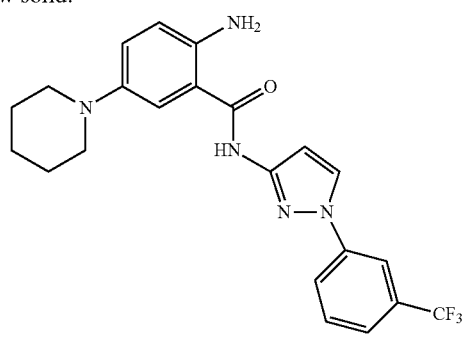

Intermediate 8d 2-amino-5-(piperidin-1-yl)-N-(1-(3-(trifluoromethyl)phenyl)-1H-pyrazol-3-yl)benzamide Into a 50-mL round-bottom flask, was placed a solution of 2-nitro-5-(piperidin-1-yl)-N-(1-(3-(trifluoromethyl)phenyl)-1H-pyrazol-3-yl)benzamide (900 mg, 1.96 mmol, 1.00 equiv) in methanol (15 mL) and ethyl acetate (15 mL). The mixture was treated with Pd/C (500 mg) stirred under a hydrogen atmosphere for 1 h at room temperature in an oil bath. The reaction progress was monitored by LCMS. The solids were filtered out. The resulting mixture was concentrated under vacuum to give 600 mg (71%) of product as a brown solid.

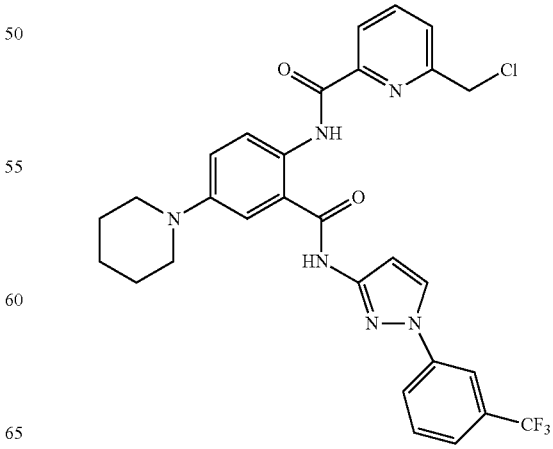

Intermediate 8e 6-(chloromethyl)-N-(4-(piperidin-1-yl)-2-((1-(3-(trifluoromethyl)phenyl)-1H-pyrazol-3-yl)carbamoyl)phenyl)picolinamide Into a 50-mL round bottom flask, was placed a solution of 2-amino-5-(piperidin-1-yl)-N-(1-(3-(trifluoromethyl)phenyl)-1H-pyrazol-3-yl)benzamide (100 mg, 0.23 mmol, 1.00 equiv) in dichloromethane (3 mL), 6-(chloromethyl)picolinic acid (50 mg, 0.29 mmol, 1.25 equiv), EDC.HCl (67 mg, 0.35 mmol, 1.50 equiv), and 4-dimethylaminopyridine (43 mg, 0.35 mmol, 1.51 equiv). The resulting solution was stirred overnight at 25° C. in an oil bath. The mixture was concentrated under vacuum to give 170 mg (75%) of product as a

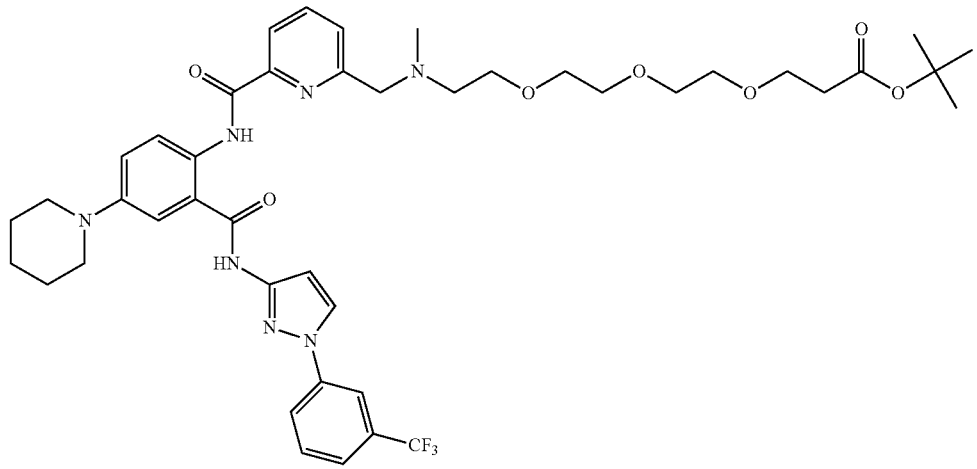 [SMILES: CN(CCOCCOCCOCCC(=O)OC(C)(C)C)Cc1cccc(C(=O)Nc2ccc(N3CCCCC3)cc2C(=O)Nc2ccn(-c3cccc(C(F)(F)F)c3)n2)n1]

Intermediate 8f tert-butyl 3-(2-(2-(2-(((6-((4-(piperidin-1-yl)-2-((1-(3-(trifluoromethyl)-phenyl)-1H-pyrazol-3-yl)carbamoyl)phenyl)carbamoyl)pyridin-2-yl)methyl)(methyl)-amino)ethoxy)ethoxy)ethoxy)propanoate Into a 50-mL round bottom flask, was placed a solution of 6-(chloromethyl)-N-(4-(piperidin-1-yl)-2-((1-(3-(trifluoromethyl)phenyl)-1H-pyrazol-3-yl)carbamoyl)phenyl)picolinamide (170 mg, 0.29 mmol, 1.00 equiv) in N,N-dimethylformamide (5 mL), tert-butyl 3-(2-(2-(2-(methylamino)ethoxy)ethoxy)ethoxy)-propanoate (255 mg, 0.88 mmol, 3.00 equiv), potassium iodide (24.2 mg, 0.15 mmol, 0.50 equiv), and potassium carbonate (79.5 mg, 0.58 mmol, 1.97 equiv). The resulting solution was stirred for 2.5 h at 70° C. in an oil bath. The reaction progress was monitored by LCMS. The resulting solution was diluted with 50 mL of water. The resulting solution was extracted with 3×50 mL of ethyl acetate and the organic layers combined. The resulting mixture was washed with 3×50 mL of brine, dried over anhydrous sodium sulfate, and concentrated under vacuum. This resulted in

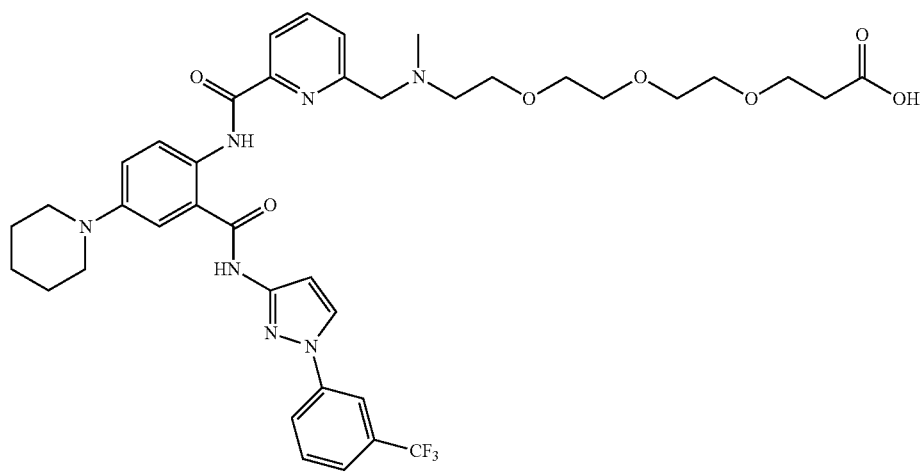 [SMILES: CN(CCOCCOCCOCCC(=O)O)Cc1cccc(C(=O)Nc2ccc(N3CCCCC3)cc2C(=O)Nc2ccn(-c3cccc(C(F)(F)F)c3)n2)n1]

Example 8

2-methyl-1-(6-((4-(piperidin-1-yl)-2-((1-(3-(trifluoromethyl)phenyl)-1H-pyrazol-3-yl)carbamoyl)phenyl)carbamoyl)pyridin-2-yl)-5,8,11-trioxa-2-azatetradecan-14-oic acid Into a 50-mL round bottom flask, was placed a solution of tert-butyl 3-(2-(2-(2-(((6-((4-(piperidin-1-yl)-2-((1-(3-(trifluoromethyl)phenyl)-1H-pyrazol-3-yl)carbamoyl)-phenyl)carbamoyl)pyridin-2-yl)methyl)(methyl)amino)ethoxy)ethoxy)ethoxy)propanoate (210 mg, 0.25 mmol, 1.00 equiv) in dichloromethane (4 mL), and trifluoroacetic acid (2 mL). The resulting solution was stirred for 2 h at room temperature. The reaction progress was monitored by LCMS. The resulting mixture was concentrated under vacuum. The crude product was purified by reverse phase HPLC eluting with a water/$CH_3CN$ gradient containing 0.05% TFA. The product was obtained as 32.9 mg (13%) of a brown solid. $^1$H-NMR (300 MHz, $CD_3OD$, ppm): δ 8.81-8.78(d, J=9.3 Hz, 1H), 8.48-8.47(d, J=2.7 Hz, 1H), 8.33-8.31(d, J=7.5 Hz, 1H), 8.21-8.16 (d, J=7.5 Hz, 2H), 7.87-7.86(d, J=2.4 Hz, 1H), 7.79-7.72(m, 2H), 7.64-7.62(d, J=6.9 Hz, 2H), 6.98-6.97(d, J=2.4 Hz, 1H), 4.75(s, 2H), 3.80-3.77(t, J=4.5 Hz, 2H), 3.66-3.47(m, 16H), 3.11-3.09(d, J=6.3 Hz, 3H), 2.49-2.45(d, J=6 Hz, 2H), 1.94-1.75(m, 6H). MS (ES, m/z): 782 [M+H]$^+$.

Example 9

2-4-(((2-(Diethylamino)ethyl)(methyl)amino)methyl)benzamido-5-(piperidin-1-yl)-N-(1-(3-(trifluoromethyl)phenyl)-1H-pyrazol-3-yl)benzamide Scheme 7. 1. N,N-diethyl-N-methylethylenediamine; 2 EDC·HCl, DMAP, DCM.

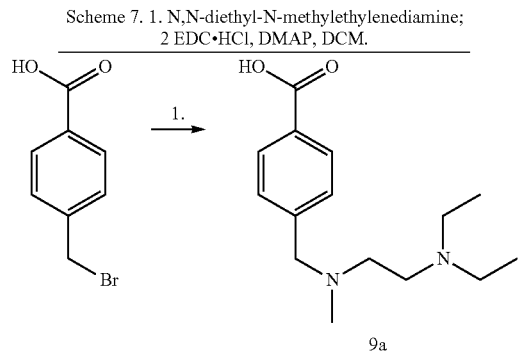

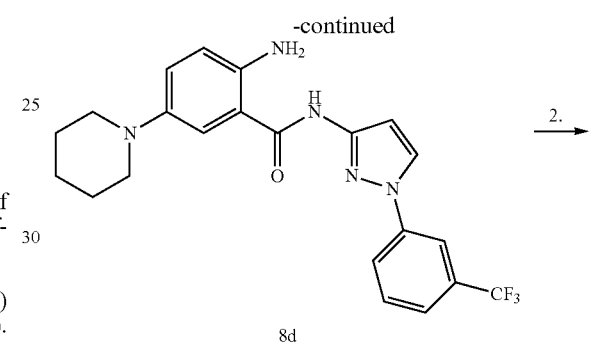

8d

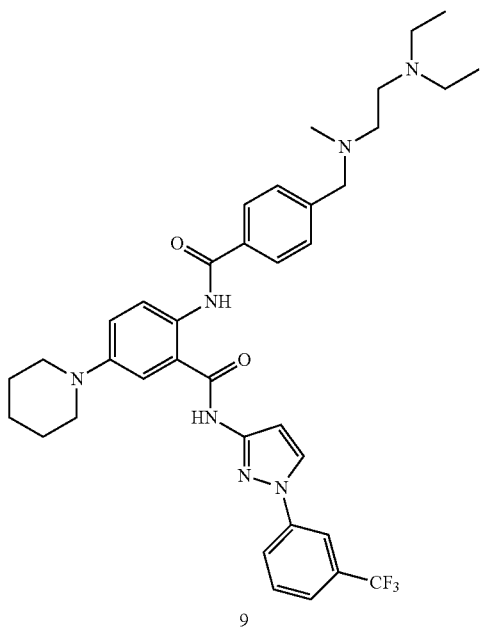

9

J=8.4 Hz, 2H), 7.39(d, J=8.1 Hz, 2H), 3.68(s, 2H), 3.23-3.15 (m, 6H), 2.91(m, 2H), 2.33(s, 3H), 1.33-1.27(m, 6H). MS (ES, m/z): 265 [M+H]$^+$.

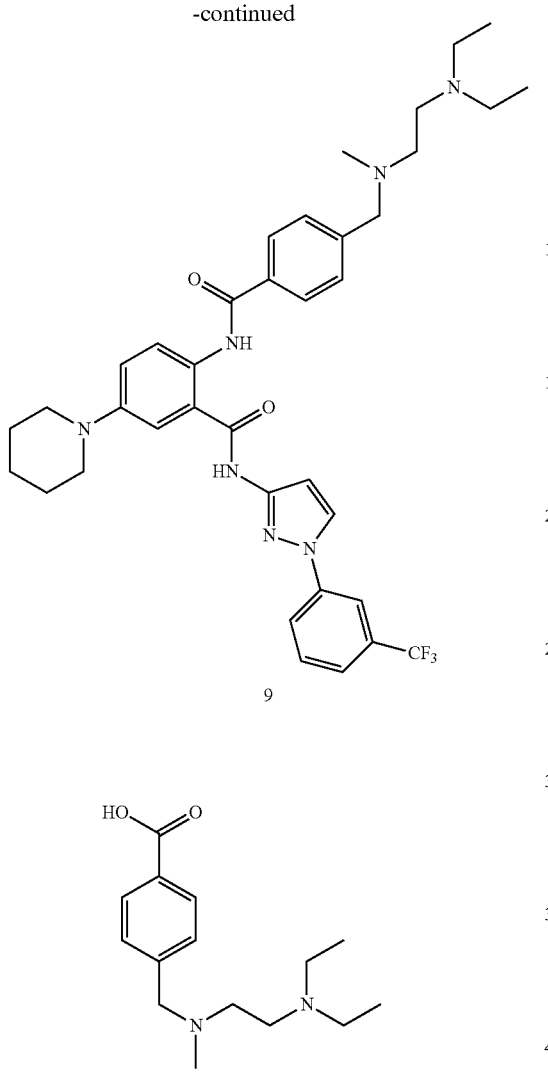

9

Intermediate 9a 4-(((2-(diethylamino)ethyl)(methyl)amino)methyl) benzoic acid

Into a 1000-mL round bottom flask, was placed a solution of N1,N1-diethyl-N2-methylethane-1,2-diamine (10 g, 69.23 mmol, 1.20 equiv, 90%) in N,N-dimethylformamide (500 mL), 4-(chloromethyl)benzoic acid (11.5 g, 67.65 mmol, 1.00 equiv), potassium carbonate (10 g, 71.94 mmol, 3.00 equiv), and potassium iodide (1.95 g, 11.75 mmol, 0.20 equiv). The resulting solution was stirred for 2 h at 90° C. in an oil bath. The solids were filtered out. The resulting mixture was concentrated under vacuum. The crude product (10 g) was purified by reverse phase chromatography eluting with a water/methanol gradient. This resulted in 5 g (27%) of 4-(((2-(diethylamino)ethyl)(methyl)amino)methyl)benzoic acid as a white solid. $^1$H-NMR (300 MHz, CDCl$_3$, ppm): δ 8.00(d,

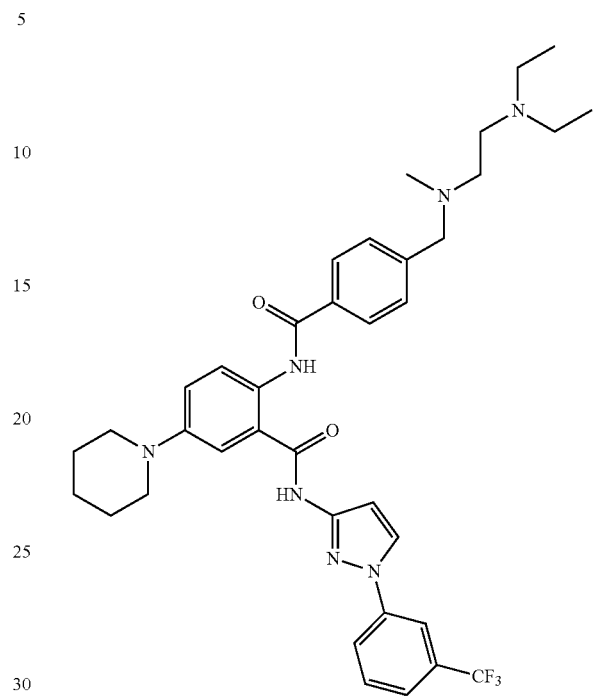

Example 9

2-(4-(((2-(diethylamino)ethyl)(methyl)amino)methyl)benzamido)-5-(piperidin-1-yl)-N-(1-(3-(trifluoromethyl)phenyl)-1H-pyrazol-3-yl)benzamide Into a 5-mL vial, was placed a solution of 2-amino-5-(piperidin-1-yl)-N-(1-(3-(trifluoromethyl)phenyl)-1H-pyrazol-3-yl)benzamide 8d (100 mg, 0.23 mmol, 1.00 equiv) in dichloromethane (5 mL), 4-(((2-(diethylamino)ethyl)(methyl)amino)methyl)benzoic acid (74 mg, 0.28 mmol, 1.20 equiv), EDC.HCl (90 mg, 0.47 mmol, 2.00 equiv), and 4-dimethylaminopyridine (43 mg, 0.35 mmol, 1.50 equiv). The resulting solution was stirred overnight at 30° C. in an oil bath. The reaction progress was monitored by LCMS. The resulting mixture was washed with 3×10 mL of water and 1×10 mL of brine. The mixture was dried over anhydrous sodium sulfate and concentrated under vacuum. The crude product (150 mg) was purified by reverse phase HPLC eluting with a water/CH$_3$CN gradient containing 0.05% TFA. The product was obtained as 57.8 mg (31%) of a light yellow solid. $^1$H-NMR (300 MHz, CD$_3$OD, ppm): δ 8.684(d, J=9 Hz, 1H), 8.392-8.400(m, 1H), 8.179(s, 1H), 8.047-8.075(m, 3H), 7.991-7.999(m, 1H), 7.589-7.727(m, 5H), 7.078-7.087(m, 1H), 4.007(s, 2H), 3.556-3.615(m, 4H), 3.393-3.436(m, 2H), 3.171-3.263(m, 4H), 3.052-3.095(m, 2H), 2.538-2.560(m, 3H), 1.998(m, 4H), 1.788-1.804(m, 2H), 1.286-1.334(m, 6H). MS (ES, m/z): 676 [M+H]$^+$.

Example 10

N1-(2-(2-Hydroxyethoxyl)ethyl)-N3-(4-(piperidin-1-yl)-2-((1-(3-(trifluoromethyl)phenyl)-1H-imidazol-4-yl)carbamoyl)phenyl)isophthalamide Scheme 8. 1. 2-(2-aminoethoxy)ethanol, HATU, DIEA; 2. LiOH•H₂O; 3. 3-(trifluoromethyl)iodobenzene, K₂CO₃, CuI, proline; 4. H₂, Pd/C; 5. EDC•HCl, DMAP, DCM, 5-(1-piperidinyl)-2-nitrobenzoic acid; 5. Intermediate 10b; 6. H₂, Pd/C; 7. 3-((2-2-hydroxyethoxy)ethyl)carbamoyl)benzoic acid, EDC•HCl, DMAP.

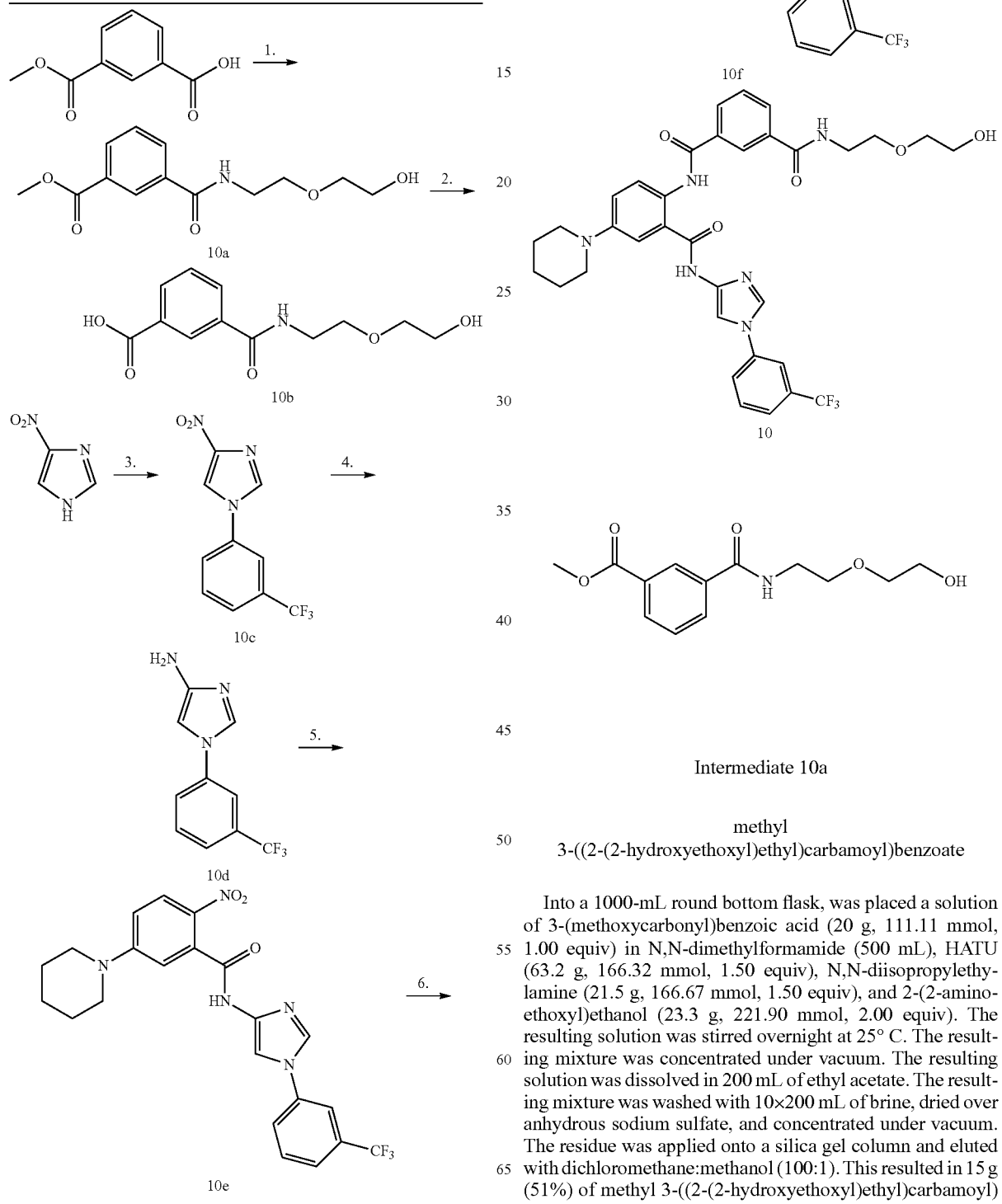

Intermediate 10a methyl 3-((2-(2-hydroxyethoxyl)ethyl)carbamoyl)benzoate

Into a 1000-mL round bottom flask, was placed a solution of 3-(methoxycarbonyl)benzoic acid (20 g, 111.11 mmol, 1.00 equiv) in N,N-dimethylformamide (500 mL), HATU (63.2 g, 166.32 mmol, 1.50 equiv), N,N-diisopropylethylamine (21.5 g, 166.67 mmol, 1.50 equiv), and 2-(2-aminoethoxyl)ethanol (23.3 g, 221.90 mmol, 2.00 equiv). The resulting solution was stirred overnight at 25° C. The resulting mixture was concentrated under vacuum. The resulting solution was dissolved in 200 mL of ethyl acetate. The resulting mixture was washed with 10×200 mL of brine, dried over anhydrous sodium sulfate, and concentrated under vacuum. The residue was applied onto a silica gel column and eluted with dichloromethane:methanol (100:1). This resulted in 15 g (51%) of methyl 3-((2-(2-hydroxyethoxyl)ethyl)carbamoyl)benzoate as red oil.

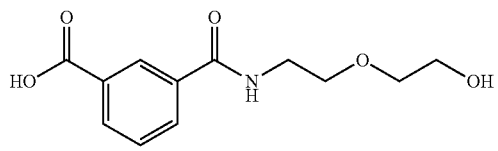 [SMILES: O=C(O)c1cccc(C(=O)NCCOCCO)c1]

Intermediate 10b 3-((2-(2-hydroxyethoxyl)ethyl)carbamoyl)benzoic acid

Into a 500-mL round bottom flask, was placed a solution of methyl 3-((2-(2-hydroxyethoxyl)ethyl)carbamoyl)benzoate (10 g, 37.45 mmol, 1.00 equiv) in tetrahydrofuran (40 mL), and a solution of lithium hydroxide hydrate (23.4 g, 558.33 mmol, 15.00 equiv) in water (30 mL). The resulting solution was stirred overnight at room temperature. The resulting mixture was concentrated under vacuum. The solution was adjusted to pH 3-4 with hydrochloric acid (2 mol/L), extracted with 3×10 mL of ethyl acetate and the organic layers combined. The resulting mixture was washed with 2×10 mL of brine, dried over anhydrous sodium sulfate, and concentrated under vacuum. The residue was applied onto a silica gel column and eluted with dichloromethane:methanol (50:1). This resulted in 5 g (53%) of 3-((2-(2-hydroxyethoxyl)ethyl) carbamoyl)benzoic acid as a yellowish solid. $^1$H-NMR (300 MHz, DMSO, ppm): δ 13.25(s, 1H), 8.71(m, 1H), 8.48(d, J=8.5 Hz 1H), 8.06(m, 2H), 7.62(m, 1H), 4.59(s, 1H), 3.41-3.60 (m, 8H). MS (ES, m/z): 254 [M+H]$^+$.

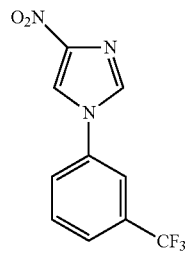 [SMILES: O=[N+]([O-])c1cn(-c2cccc(C(F)(F)F)c2)cn1]

Intermediate 10c 4-nitro-1-(3-(trifluoromethyl)phenyl)-1H-imidazole

Into a 500-mL round bottom flask, was placed a solution of 4-nitro-1H-imidazole (10 g, 88.50 mmol, 1.00 equiv) in DMSO (50 mL), 1-iodo-3-(trifluoromethyl)benzene (24 g, 88.24 mmol, 1.00 equiv), potassium carbonate (25 g, 181.16 mmol, 2.00 equiv), copper(I) iodide (2.5 g, 13.16 mmol, 0.15 equiv), and L-proline (1.53 g, 13.30 mmol, 0.15 equiv). The resulting solution was stirred overnight at 85° C. in an oil bath. The resulting solution was diluted with 1000 mL of ethyl acetate. The solids were filtered out. The filtrate was washed with 2×500 mL of brine, dried over sodium sulfate, and concentrated under vacuum. The residue was applied onto a silica gel column and eluted with ethyl acetate/petroleum ether (1:3) to yield 6.7 g (28%) of 4-nitro-1-(3-(trifluoromethyl)phenyl)-1H-imidazole as a pale solid.

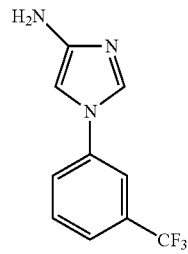

Intermediate 10d 1-(3-(trifluoromethyl)phenyl)-1H-imidazol-4-amine

Into a 100-mL round bottom flask, was placed a solution of 4-nitro-1-(3-(trifluoromethyl)phenyl)-1H-imidazole (1.5 g, 5.54 mmol, 1.00 equiv, 95%) in methanol (30 mL). The mixture was treated with Pd/C (1.5 g) and stirred under a hydrogen atmosphere for 4 h at room temperature. The solids were filtered out. The resulting mixture was concentrated under vacuum. This resulted in 1.2 g (88%) of 1-(3-(trifluoromethyl)phenyl)-1H-imidazol-4-amine as a brown oil.

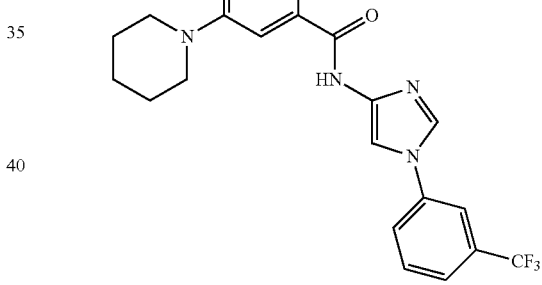

Intermediate 10e 2-nitro-5-(piperidin-1-yl)-N-(1-(3-(trifluoromethyl) phenyl)-1H-imidazol-4-yl)benzamide Into a 250-mL round-bottom flask, was placed a solution of 1-(3-(trifluoromethyl)phenyl)-1H-imidazol-4-amine (1.2 g, 4.49 mmol, 1.00 equiv, 85%) in dichloromethane (30 mL), 2-nitro-5-(piperidin-1-yl)benzoic acid (1.32 g, 5.07 mmol, 1.00 equiv, 96%), EDC.HCl (2 g, 10.42 mmol, 2.00 equiv), and 4-dimethylaminopyridine (1.29 g, 10.57 mmol, 2.00 equiv). The resulting solution was stirred overnight at 28° C. The resulting solution was diluted with 200 mL of dichloromethane. The resulting mixture was washed with 1×30 mL of 10% sodium bicarbonate and 1×30 mL of brine, dried over sodium sulfate, and concentrated under vacuum. The residue was applied onto a silica gel column and eluted with ethyl acetate/petroleum ether (1:1) to give 600 mg (22%) of product as brown oil.

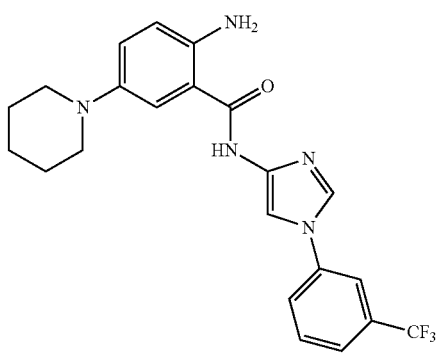 [SMILES: O=C(Nc1cn(-c2cccc(C(F)(F)F)c2)cn1)c1cc(N2CCCCC2)ccc1[N+](=O)[O-]]

Intermediate 10f 2-amino-5-(piperidin-1-yl)-N-(1-(3-(trifluoromethyl)phenyl)-1H-imidazol-4-yl)benzamide Into a 100-mL round-bottom flask, was placed a solution of 2-nitro-5-(piperidin-1-yl)-N-(1-(3-(trifluoromethyl)phenyl)-1H-imidazol-4-yl)benzamide (600 mg, 1.11 mmol, 1.00 equiv, 85%) in methanol/dichloromethane (10/5 mL). The mixture was treated with Pd/C (600 mg) and stirred under an atmosphere of hydrogen overnight at room temperature. The solids were filtered out. The resulting mixture was concentrated under vacuum to give 450 mg (85%) of product as a brown solid.

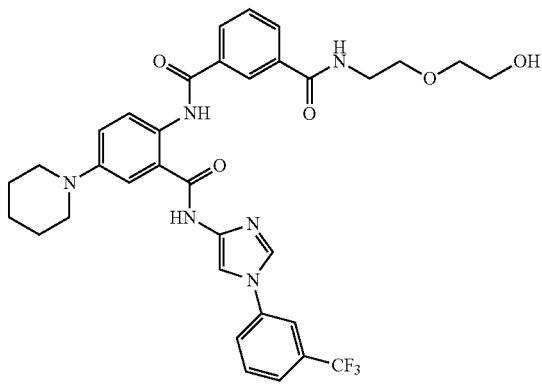 [SMILES: O=C(NCCOCCO)c1cccc(C(=O)Nc2ccc(N3CCCCC3)cc2C(=O)Nc2cn(-c3cccc(C(F)(F)F)c3)cn2)c1]

Example 10

N1-(2-(2-hydroxyethoxy)ethyl)-N3-(4-(piperidin-1-yl)-2-((1-(3-(trifluoro-methyl)phenyl)-1H-imidazol-4-yl)carbamoyl)phenyl)isophthalamideN1-(2-(2-hydroxy-ethoxy)ethyl)-N3-(4-(piperidin-1-yl)-2-((1-(3-(trifluoromethyl)phenyl)-1H-imidazol-4-yl)carbamoyl)phenyl)isophthalamide Into a 50-mL round bottom flask, was placed a solution of 2-amino-5-(piperidin-1-yl)-N-(1-(3-(trifluoromethyl)phenyl)-1H-imidazol-4-yl)benzamide (150 mg, 0.32 mmol, 1.00 equiv, 92%) in dichloromethane (8 mL), 3-((2-(2-hydroxyethoxyl)ethyl)carbamoyl)benzoic acid (133 mg, 0.45 mmol, 1.50 equiv, 85%), EDC.HCl (134 mg, 0.70 mmol, 2.00 equiv), and 4-dimethylaminopyridine (85 mg, 0.70 mmol, 2.00 equiv). The resulting solution was stirred overnight at 25° C. The resulting solution was diluted with 100 mL of dichloromethane. The resulting mixture was washed with 1×20 mL of 10% sodium bicarbonate and 1×20 mL of brine, dried over anhydrous sodium sulfate, and concentrated under vacuum. The residue was applied onto a silica gel column and eluted with dichloromethane/methanol (20:1). The crude product (120 mg) was purified by reverse phase HPLC eluting with a water/CH$_3$CN gradient containing 0.05% TFA. The product was obtained as 67.8 mg (22%) of a light yellow solid. $^1$H-NMR (300 MHz, CD$_3$OD, ppm): δ 8.74 (d, J=9 Hz, 1H), 8.53 (s, 1H), 8.35(s, 1H), 8.01 (m, 6H), 7.74 (m, 3H), 7.44 (m, 1H), 3.66 (m, 12H), 2.06 (m, 4H), 1.83 (m, 2H). MS (ES, m/z): 665 [M+H]$^+$.

Example 11

N1-Methyl-N1-(2-morpholinoethyl)-N3-(4-(piperidin-1-yl)-2-((1-(3-(trifluoromethyl)phenyl)-1H-pyrazol-3-yl)carbamoyl)phenyl)isophthalamide

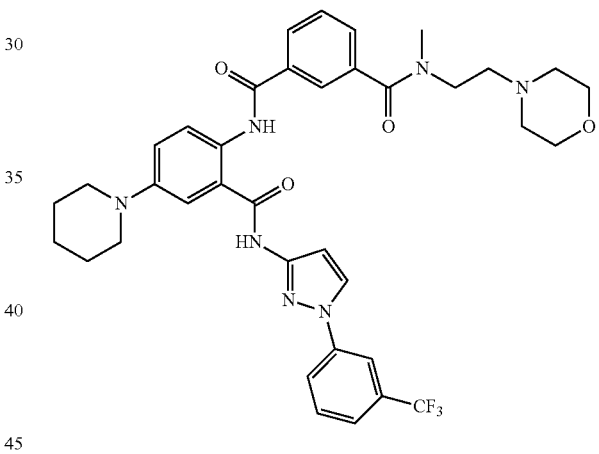

Into a 50-mL round bottom flask, was placed 2-amino-5-(piperidin-1-yl)-N-(1-(3-(trifluoromethyl)phenyl)-1H-pyrazol-3-yl)benzamide 8d (100 mg, 0.23 mmol, 1.00 equiv), 3-(methyl(2-morpholinoethyl)carbamoyl)benzoic acid (130 mg, 0.45 mmol, 1.91 equiv), EDC.HCl (67 mg, 0.35 mmol, 1.50 equiv), 4-dimethylaminopyridine (43 mg, 0.35 mmol, 1.51 equiv), and dichloromethane (5 mL). The resulting solution was stirred for 4 h at 25° C. in an oil bath. The reaction progress was monitored by LCMS. The resulting mixture was washed with 3×10 mL of water and 3×10 mL of aqueous NH$_4$Cl. The mixture was dried over anhydrous sodium sulfate and concentrated under vacuum. The crude product was purified by reverse phase HPLC eluting with a water/CH$_3$CN gradient containing 0.05% TFA. The product was obtained as 108.6 mg (66%) of a white solid. $^1$H-NMR (400 MHz, CD$_3$OD, ppm): δ 8.66-8.64(d, J=8.8 Hz, 1H), 8.39(s, 1H), 8.16 (s, 3H), 8.07-8.05(d, J=7.6 Hz, 1H), 7.99(s, 1H), 7.79(s, 1H), 7.16-7.68 (m, 3H), 7.61(s, 1H), 7.07(s, 1H), 4.11-4.10(d, J=3.2 Hz, 2H), 3.98 (s, 3H), 3.80-3.77(m, 4H), 3.59-3.54 (m, 6H), 3.14(m, 4H), 1.99-1.79(m, 6H). MS (ES, m/z): 704 [M+H]$^+$.

Example 12

2-(3-(((2-(Diethylamino)ethyl)(methyl)amino)methyl)benzamido)-5-(piperidin-1-yl)-N-(1-(3-(trifluoromethyl)phenyl)-1H-pyrazol-3-yl)benzamide Scheme 9. 1. N1,N1-diethyl-N2-methylethane-1,2-diamine, K₂CO₃; 2. EDC·HCl, DMAP, dichloromethane.

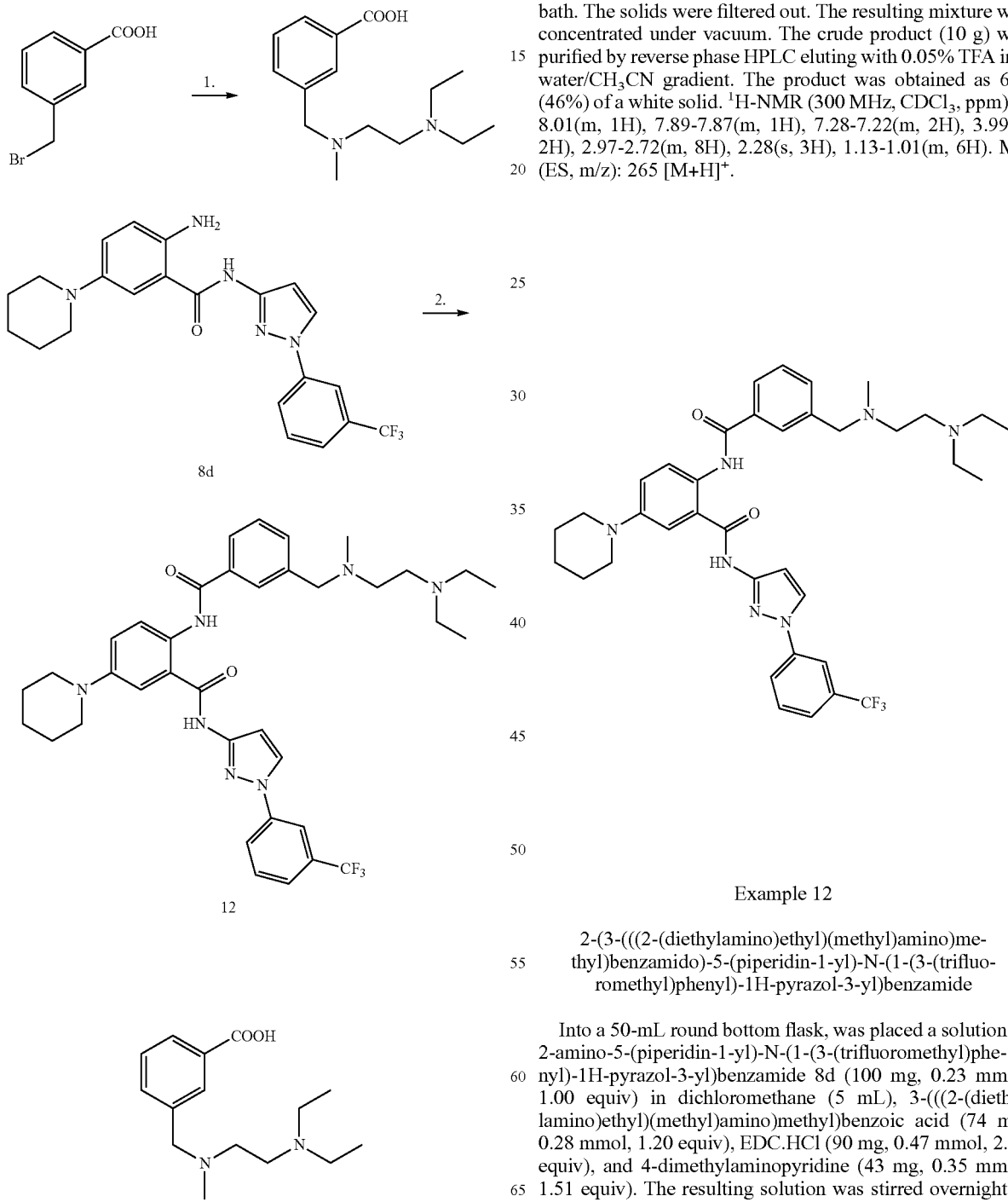

Intermediate 12a 3-4(2-(diethylamino)ethyl)(methyl)amino)methyl)benzoic acid

Into a 1000-mL round bottom flask, was placed a solution of N1,N1-diethyl-N2-methylethane-1,2-diamine (9.1 g, 63.00 mmol, 1.50 equiv, 90%) in N,N-dimethylformamide (500 mL), 3-(bromomethyl)benzoic acid (10 g, 46.51 mmol, 1.00 equiv), potassium carbonate (7.8 g, 56.12 mmol, 1.20 equiv), and potassium iodide (1.55 g, 9.34 mmol, 0.20 equiv). The resulting solution was stirred for 2 h at 90° C. in an oil bath. The solids were filtered out. The resulting mixture was concentrated under vacuum. The crude product (10 g) was purified by reverse phase HPLC eluting with 0.05% TFA in a water/CH₃CN gradient. The product was obtained as 6 g (46%) of a white solid. ¹H-NMR (300 MHz, CDCl₃, ppm): δ 8.01(m, 1H), 7.89-7.87(m, 1H), 7.28-7.22(m, 2H), 3.99(s, 2H), 2.97-2.72(m, 8H), 2.28(s, 3H), 1.13-1.01(m, 6H). MS (ES, m/z): 265 [M+H]⁺.

Example 12

2-(3-(((2-(diethylamino)ethyl)(methyl)amino)methyl)benzamido)-5-(piperidin-1-yl)-N-(1-(3-(trifluoromethyl)phenyl)-1H-pyrazol-3-yl)benzamide Into a 50-mL round bottom flask, was placed a solution of 2-amino-5-(piperidin-1-yl)-N-(1-(3-(trifluoromethyl)phenyl)-1H-pyrazol-3-yl)benzamide 8d (100 mg, 0.23 mmol, 1.00 equiv) in dichloromethane (5 mL), 3-(((2-(diethylamino)ethyl)(methyl)amino)methyl)benzoic acid (74 mg, 0.28 mmol, 1.20 equiv), EDC.HCl (90 mg, 0.47 mmol, 2.01 equiv), and 4-dimethylaminopyridine (43 mg, 0.35 mmol, 1.51 equiv). The resulting solution was stirred overnight at 30° C. in an oil bath. The reaction progress was monitored by LCMS. The resulting mixture was washed with 3×10 mL of water and 1×10 mL of brine. The mixture was dried over sodium sulfate. The solids were filtered out. The resulting mixture was concentrated under vacuum. The crude product (150 mg) was purified by reverse phase HPLC eluting with a water/CH$_3$CN gradient containing 0.05% TFA. The product was obtained as 58.5 mg (32%) of a yellow solid. $^1$H-NMR (300 MHz, CD$_3$OD, ppm): δ 8.502-8.532(d, J=9.0 Hz, 1H), 8.277-8.286(m, 1H), 8.060(s, 1H), 7.851-7.966(m, 4H), 7.475-7.610(m, 5H), 6.949-6.958(m, 1H), 3.922(s, 2H), 3.450-3.485(m, 4H), 3.273-3.316(m, 2H), 3.035-3.108(m, 4H), 2.957-2.998(m, 2H), 2.449-2.475(m, 3H), 1.857-1.872(m, 4H), 1.666-1.683(m, 2H), 1.139-1.200(m, 6H). MS (ES, m/z): 676 [M+H]$^+$.

Example 13

N1-(2-(2-Hydroxyethoxyl)ethyl)-N3-(4-(piperidin-1-yl)-2-((1-(3-(trifluoromethyl)phenyl)-1H-pyrazol-3-yl)carbamoyl)phenyl)isophthalamide

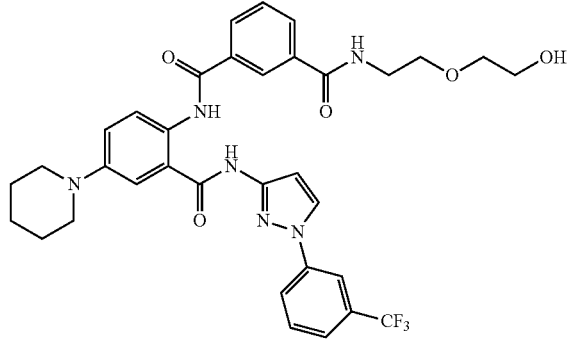 [SMILES: O=C(NCCOCCO)c1cccc(C(=O)Nc2ccc(N3CCCCC3)cc2C(=O)Nc2ccn(-c3cccc(C(F)(F)F)c3)n2)c1]

2-Amino-5-(piperidin-1-yl)-N-(1-(3-(trifluoromethyl)phenyl)-1H-pyrazol-3-yl)benzamide 8d was converted to N1-(2-(2-hydroxyethoxyl)ethyl)-N3-(4-(piperidin-1-yl)-2-((1-(3-(trifluoromethyl)phenyl)-1H-pyrazol-3-yl)carbam-oyl)phenyl)isophthalamide 13 using the procedure described for the preparation of N1-(2-(2-hydroxyethoxyl)ethyl)-N3-(4-(piperidin-1-yl)-2-((1-(3-(trifluoromethyl)phenyl)-1H-imidazol-4-yl)carbamoyl)phenyl)-isophthalamide 10. $^1$H-NMR (300 MHz, CD$_3$OD, ppm): δ 8.683(d, J=9 Hz, 1H), 8.498(s, 1H), 8.382-8.391(m, 1H), 8.151-8.171(m, 2H), 8.039-8.086(m, 3H), 7.655-7.715(m, 3H), 7.592(d, J=7.8 Hz, 1H), 7.128-7.136(m, 1H), 3.579-3.710(m, 12H), 2.002-2.016 (m, 4H), 1.803-1.818(m, 2H). MS (ES, m/z): 665 [M+H]$^+$.

Example 14

N1-(4-Chloro-2-((1-(3-(trifluoromethyl)phenyl)-1H-pyrazol-3-yl)carbamoyl)phenyl)-N3-methyl-N3-(2-morpholinoethyl)isophthalamide 2,2,2-trifluoroacetate

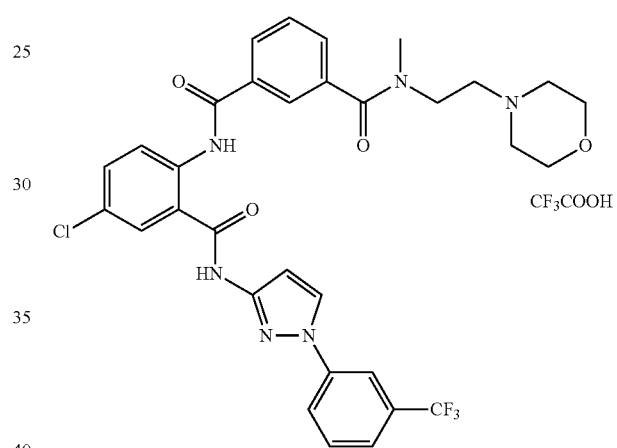

Into a 50-mL round bottom flask, was placed a solution of 2-amino-5-chloro-N-(1-(3-(trifluoromethyl)phenyl)-1H-pyrazol-3-yl)benzamide 6d (150 mg, 0.39 mmol, 1.00 equiv) in dichloromethane (6 mL), and pyridine (93.6 mg, 1.18 mmol, 3.00 equiv). To this was added dropwise, a solution of 3-(methyl(2-morpholinoethyl)carbamoyl)benzoyl chloride 1f (147 mg, 0.47 mmol, 1.20 equiv) in dichloromethane (2 mL) over 10 min with stirring at 0° C. The resulting solution was stirred for 1 h at room temperature. The resulting solution was diluted with 2 mL of water, and adjusted to pH 8 with NH$_3$H$_2$O (2 mol/L). The resulting solution was extracted with 2×5 mL of dichloromethane and the organic layers combined, dried over sodium sulfate, and concentrated under vacuum. The crude product (150 mg) was purified by reverse phase HPLC eluting with a water/CH$_3$CN gradient containing 0.05% TFA. The product was obtained as 67.2 mg (22%) of a white solid. $^1$H-NMR (300 MHz, DMSO, ppm): δ 11.67 (s, 1H), 11.54 (s, 1H), 9.62 (s, 1H), 8.68-8.67 (d, J=2.7 Hz, 1H), 8.71-8.38 (d, J=9.0 Hz, 1H), 8.16-8.02 (m, 5H), 7.79-7.65 (m, 5H), 6.968-6.960 (d, J=2.4 Hz, 1H), 4.01(s, 2H), 3.84 (s, 2H), 3.42 (s, 6H), 3.18 (s, 2H), 2.98(s, 3H). MS (ES, m/z): 655 [M+H]$^+$.

Example 15
2-Methyl-1-oxo-1-(3-((4-(piperidin-1-yl)-2-((1-(3-(trifluoromethyl)phenyl)-1H-pyrazol-3-yl)carbamoyl)phenyl)carbamoyl)phenyl)-5,8,11-trioxa-2-azatetradecan-14-oic acid
Scheme 10: 1. methyl 3-(chlorocarbonyl)benzoate, Et₃N; 2. LiOH·H₂O; 3. tert-butyl 3-(2-(2-(2-methylamino)ethoxy)ethoxy)ethoxy)-propanoate 8b, EDC·HCl, DMAP, then TFA/DCM.
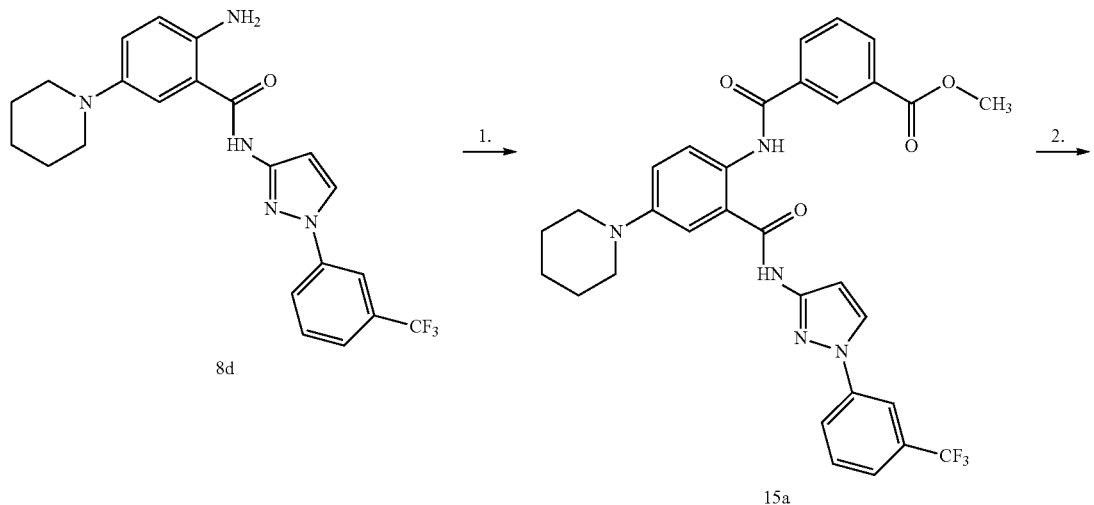
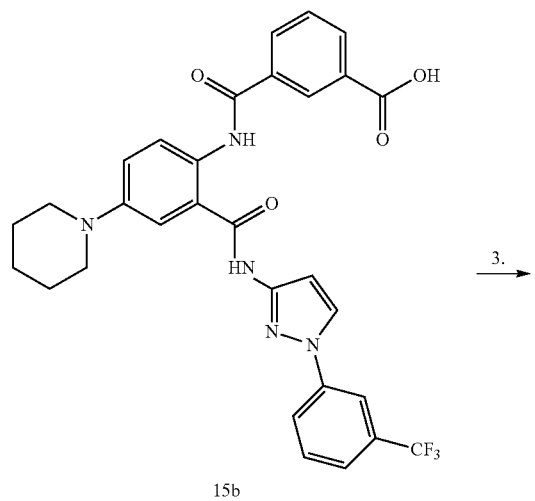

-continued

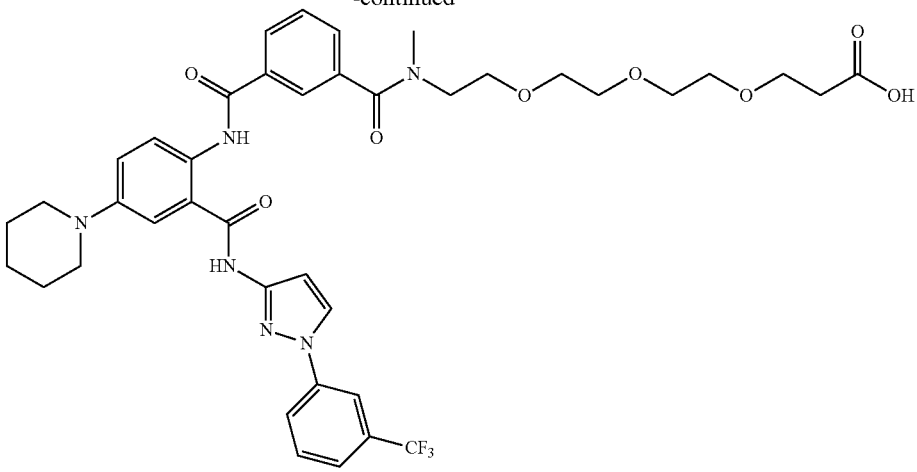

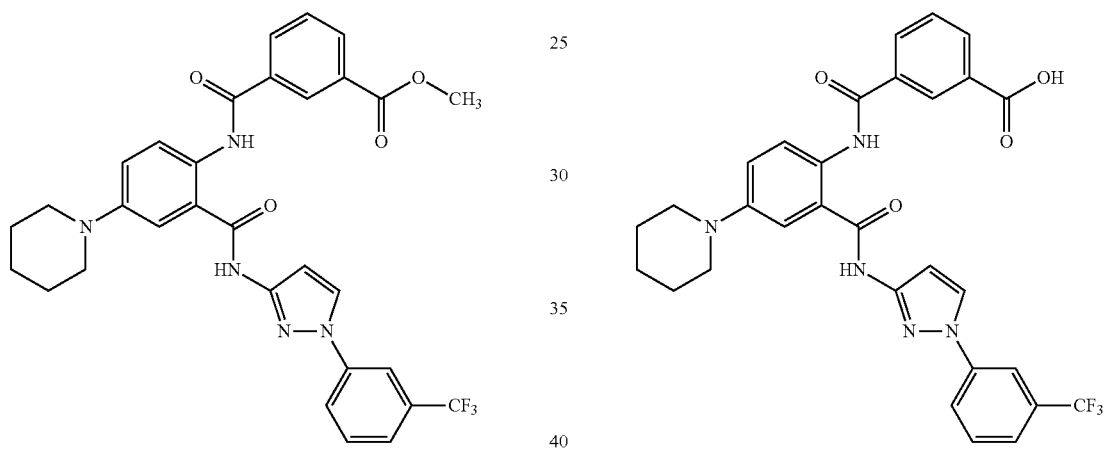

Intermediate 15a methyl 3-((4-(piperidin-1-yl)-2-((1-(3-(trifluoromethyl)phenyl)-1H-pyrazol-3-yl)carbamoyl)phenyl)carbamoyl)benzoate Into a 100-mL 3-necked round bottom flask, was placed a solution of 2-amino-5-(piperidin-1-yl)-N-(1-(3-(trifluoromethyl)phenyl)-1H-pyrazol-3-yl)benzamide (260 mg, 0.61 mmol, 1.00 equiv) in dichloromethane (20 mL), and triethylamine (123 mg, 1.22 mmol, 2.01 equiv). This was followed by dropwise addition of a solution of methyl 3-(chlorocarbonyl)benzoate (144 mg, 0.73 mmol, 1.20 equiv) in dichloromethane (10 mL) with stirring at 0° C. The resulting solution was stirred for 2 h at room temperature, with reaction progress monitored by LCMS. The resulting mixture was washed with 3×20 mL of water and 20 mL of brine, then dried over anhydrous sodium sulfate. The solids were filtered out. The resulting mixture was concentrated under vacuum to give 300 mg of crude product as a brown solid.

Intermediate 15b 3-((4-(piperidin-1-yl)-2-((1-(3-(trifluoromethyl)phenyl)-1H-pyrazol-3-yl)carbamoyl)phenyl)carbamoyl)benzoic acid Into a 100-mL round bottom flask, was placed a solution of methyl 3-((4-(piperidin-1-yl)-2-((1-(3-(trifluoromethyl)phenyl)-1H-pyrazol-3-yl)carbamoyl)phenyl)carbamoyl)benzoate (300 mg, 0.51 mmol, 1.00 equiv) in tetrahydrofuran (30 mL), water (5 mL), and lithium hydroxide hydrate (300 mg, 12.50 mmol, 24.62 equiv). The resulting solution was stirred overnight at room temperature. The reaction progress was monitored by LCMS. The resulting mixture was concentrated under vacuum. The solution was adjusted to pH 2 with hydrochloric acid 1 mol/L). The resulting solution was extracted with 3×30 mL of ethyl acetate and the organic layers combined, washed with 1×30 mL of brine, and dried over anhydrous sodium sulfate. The solids were filtered out. The resulting mixture was concentrated under vacuum. This resulted in 300 mg of crude product as a gray solid.

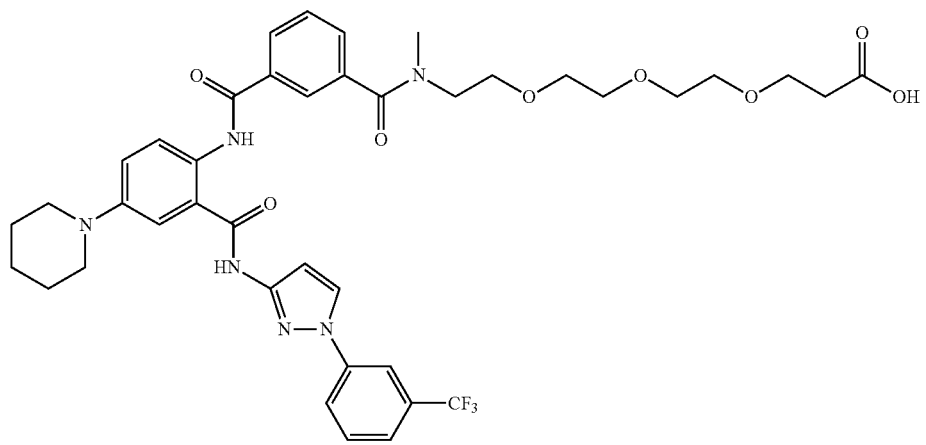 [SMILES: CN(CCOCCOCCOCCC(=O)O)C(=O)c1cccc(C(=O)Nc2ccc(N3CCCCC3)cc2C(=O)Nc2ccn(-c3cccc(C(F)(F)F)c3)n2)c1]

Example 15

2-methyl-1-oxo-1-(3-((4-(piperidin-1-yl)-2-((1-(3-(trifluoromethyl)phenyl)-1H-pyrazol-3-yl)carbamoyl)phenyl)carbamoyl)phenyl)-5,8,11-trioxa-2-azatetradecan-14-oic acid Into a 50-mL round bottom flask, was placed 3-((4-(piperidin-1-yl)-2-((1-(3-(trifluoromethyl)phenyl)-1H-pyrazol-3-yl)carbamoyl)phenyl)carbamoyl)benzoic acid 8d (150 mg, 0.26 mmol, 1.00 equiv), tert-butyl 3-(2-(2-(2-(methylamino)ethoxy)ethoxy)ethoxy)propanoate 8b (75 mg, 0.26 mmol, 0.99 equiv), EDC.HCl (75 mg, 0.39 mmol, 1.51 equiv), 4-dimethylaminopyridine (48 mg, 0.39 mmol, 1.52 equiv), and dichloromethane (5 mL). The resulting solution was stirred for 3 h at 25° C. in an oil bath, with reaction progress monitored by LCMS. The resulting solution was diluted with 10 mL of dichloromethane. The resulting mixture was washed with 3×10 mL of water and 3×10 mL of aqueous $NH_4Cl$. The mixture was dried over anhydrous sodium sulfate and concentrated under vacuum to yield 190 mg (86%) of product as a yellow solid. Into a 50-mL round bottom flask, was placed a solution of this solid (170 mg, 0.20 mmol, 1.00 equiv) in dichloromethane (3 mL), and trifluoroacetic acid (1.5 mL). The resulting solution was stirred for 2 h at room temperature. The reaction progress was monitored by LCMS. The resulting mixture was concentrated under vacuum. The crude product was purified by reverse phase HPLC eluting with a water/$CH_3CN$ gradient containing 0.05% TFA. The product was obtained as 67.2 mg (42%) of a yellow solid. $^1$H-NMR (300 MHz, $CD_3OD$, ppm): δ 8.74-8.71(d, J=9 Hz, 1H), 8.40-8.39(d, J=2.4 Hz, 1H), 8.17(s, 1H), 8.09-8.05(m, 4H), 7.76-7.58(m, 5H), 7.11-7.10(d, J=2.7 Hz, 1H), 3.79(s, 2H), 3.68-3.53(m, 17H), 3.15-3.12(d, J=11.1 Hz, 3H), 2.52-2.48(t, J=6.3 Hz, 2H), 2.04-1.81(m, 6H). MS (ES, m/z): 795 $[M+H]^+$.

Example 16

2-(3-(((3-(2-Methoxyethyl)amino)-3-oxopropyl)(methyl)amino)methyl)benzamido)-5-(piperidin-1-yl)-N-(1-(3-(trifluoromethyl)phenyl)-1H-pyrazol-3-yl)benzamide Scheme 11: 1. 3-(bromomethyl)benzoyl chloride, DIPEA; 1. N-(2-methoxyethyl)-3-(methylamino)propanamide, KI, $K_2CO_3$.

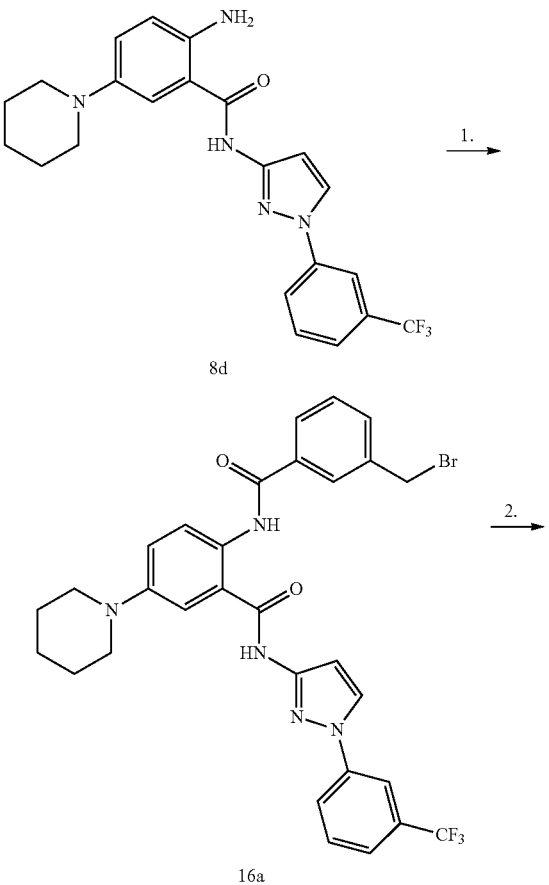

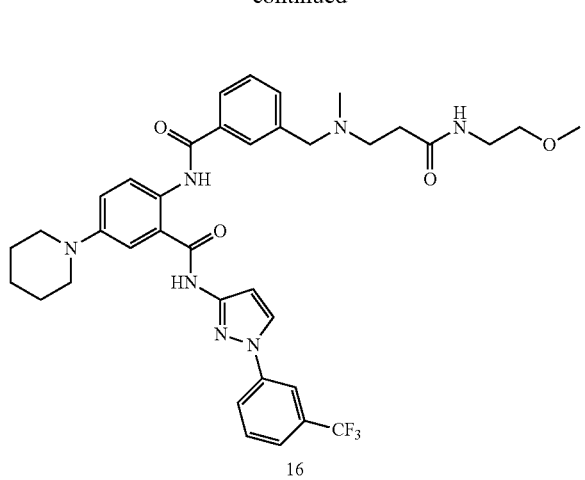

16

Intermediate 16a 2-(3-(bromomethyl)benzamido)-5-(piperidin-1-yl)-N-(1-(3-(trifluoromethyl)phenyl)-1H-pyrazol-3-yl) benzamide Into a 50-mL round bottom flask, was placed 2-amino-5-(piperidin-1-yl)-N-(1-(3-(trifluoromethyl)phenyl)-1H-pyrazol-3-yl)benzamide 8d (100 mg, 0.23 mmol, 1.00 equiv) in tetrahydrofuran (5 mL), and N,N-diisopropylethylamine (60 mg, 0.47 mmol, 2.00 equiv). To this was added 3-(bromomethyl)benzoyl chloride (75 mg, 0.32 mmol, 1.39 equiv), in portions at 0° C. The resulting solution was stirred for 2.5 h at room temperature. The reaction progress was monitored by LCMS/TLC. The resulting mixture was concentrated under vacuum. The resulting solution was diluted with 10 mL of water, extracted with 3×10 mL of ethyl acetate, and the organic layers combined. The resulting mixture was washed with 3×10 mL of brine, dried over anhydrous sodium sulfate, and concentrated under vacuum. This resulted in 160 mg (88%) of product as a brown solid.

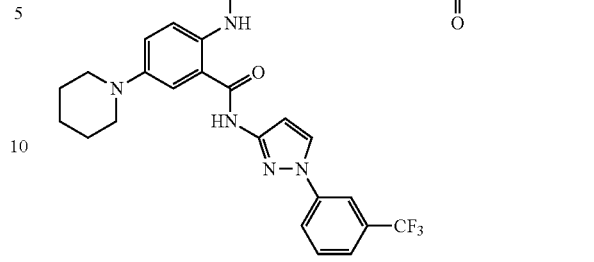

Example 16

2-(3-(((3-((2-methoxyethyl)amino)-3-oxopropyl) (methyl)amino)methyl)-benzamido)-5-(piperidin-1-yl)-N-(1-(3-(trifluoromethyl)phenyl)-1H-pyrazol-3-yl)-benzamide Into a 50-mL round bottom flask, was placed intermediate 16a-2 (160 mg, 0.26 mmol, 1.00 equiv), (123 mg, 0.77 mmol, 3.01 equiv), potassium iodide (21.2 mg, 0.13 mmol, 0.50 equiv), potassium carbonate (70.1 mg, 0.51 mmol, 1.99 equiv), and N,N-dimethylformamide (5 mL). The resulting solution was stirred for 1.5 h at 70° C. in an oil bath. The reaction progress was monitored by LCMS. The resulting solution was diluted with 20 mL of water. The resulting solution was extracted with 3×20 mL of ethyl acetate and the organic layers combined. The resulting mixture was washed with 3×20 mL of brine, dried over anhydrous sodium sulfate, and concentrated under vacuum. The crude product was purified by reverse phase HPLC eluting with a water/CH$_3$CN gradient containing 0.05% TFA. The product was obtained as 88.2 mg (42%) of a yellow solid. $^1$H-NMR (300 MHz, CD$_3$OD, ppm): δ 8.66-8.63(d, J=9.3 Hz, 1H), 8.39-8.38(d, J=2.7 Hz, 1H), 8.16-8.05(m, 3H), 7.98-7.97(d, J=2.4 Hz, 1H), 7.82-7.75(m, 1H), 7.73-7.59(m, 5H), 7.07-7.06 (d, J=2.4 Hz, 1H), 4.54-4.49(m, 2H), 3.60-3.57(t, J=5.1 Hz, 4H), 3.46-3.43(m, 3H), 3.39-3.36 (t, J=5.1 Hz, 2H), 2.88(s, 3H), 2.79-2.74(t, J=6.6 Hz, 2H), 1.99-1.78(m, 6H). MS (ES, m/z): 706 [M+H]$^+$.

Example 17

2-Methyl-1-(3-((4-(piperidin-1-yl)-2-((1-(3-(trifluoromethyl)phenyl)-1H-pyrazol-3-yl)carbamoyl)phenyl)carbamoyl)phenyl)-5,8,11-trioxa-2-azatetradecan-14-oic acid

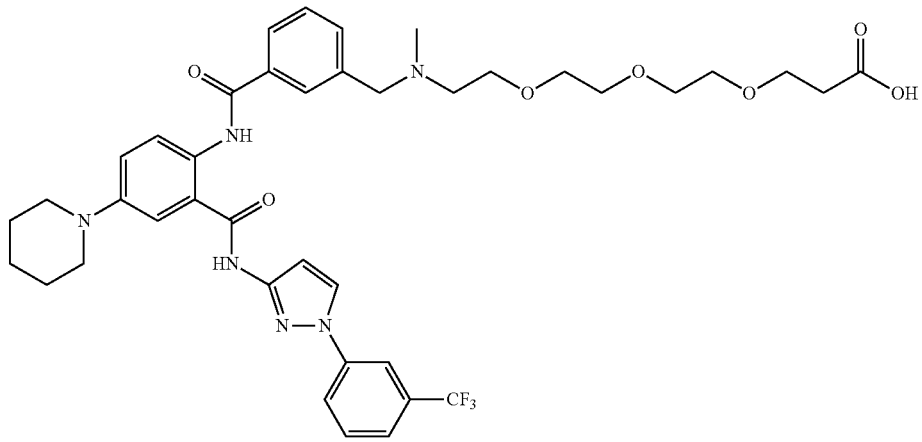 [SMILES: CN(CCOCCOCCOCCC(=O)O)Cc1cccc(C(=O)Nc2ccc(N3CCCCC3)cc2C(=O)Nc2ccn(-c3cccc(C(F)(F)F)c3)n2)c1]

Into a 50-mL round bottom flask, was placed a solution of 2-(3-(bromomethyl)benzamido)-5-(piperidin-1-yl)-N-(1-(3-(trifluoromethyl)phenyl)-1H-pyrazol-3-yl)benzamide 16a(120 mg, 0.19 mmol, 1.00 equiv) in N,N-dimethylformamide (3 mL), tert-butyl 3-(2-(2-(2-(methylamino)ethoxy)ethoxy)ethoxy)propanoate 8b (168 mg, 0.58 mmol, 3.01 equiv), potassium iodide (18 mg, 0.11 mmol, 0.57 equiv), and potassium carbonate (54 mg, 0.39 mmol, 2.04 equiv). The resulting solution was stirred overnight at 70° C. in an oil bath. The reaction progress was monitored by LCMS. The resulting solution was diluted with 20 mL of water. The resulting solution was extracted with 3×20 mL of ethyl acetate and the organic layers combined. The resulting mixture was washed with 3×20 mL of brine, dried over anhydrous sodium sulfate, and concentrated under vacuum. This resulted in 220 mg (96%) of product as a yellow solid.

Into a 50-mL round bottom flask, was placed a solution of 206 mg of this solid in dichloromethane (4 mL), and trifluoroacetic acid (2 mL). The resulting solution was stirred for 1 h at room temperature. The reaction progress was monitored by LCMS. The resulting mixture was concentrated under vacuum. The crude product was purified by reverse phase HPLC eluting with a water/$CH_3CN$ gradient containing 0.05% TFA. The product was obtained as 58.1 mg (26%) of a yellow solid. $^1$H-NMR (300 MHz, $CD_3OD$, ppm): δ 8.61-8.59(d, J=8.7 Hz, 1H), 8.40-8.39(d, J=2.4 Hz, 1H), 8.16-8.12 (m, 3H), 8.08-8.05(d, J=8.4 Hz, 1H), 7.90(s, 1H), 7.81-7.67 (m, 3H), 7.61-7.59(d, J=7.8 Hz, 2H), 7.05-7.04(d, J=2.4 Hz, 1H), 4.53(s, 2H), 3.89-3.85(t, J=4.8 Hz, 2H), 3.69-3.53(m, 15H), 3.41(s, 2H), 2.92(s, 3H), 2.51-2.47(t, J=6 Hz, 2H), 1.95-1.76(m, 6H). MS (ES, m/z): 781 [M+H]$^+$.

Example 18

3-((3-((4-(Piperidin-1-yl)-2-((1-(3-(trifluoromethyl)phenyl)-1H-pyrazol-3-yl)carbamoyl)phenyl)carbamoyl)benzyl)thio)benzoic acid

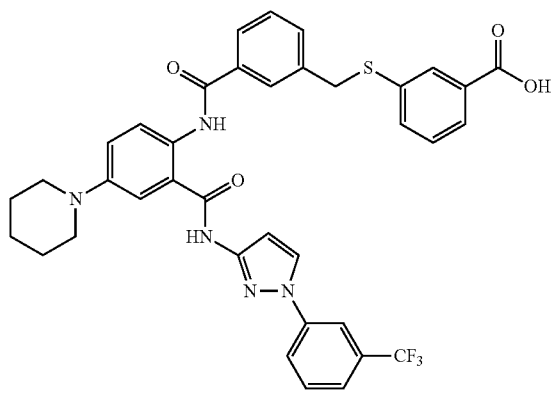 [SMILES: O=C(O)c1cccc(SCc2cccc(C(=O)Nc3ccc(N4CCCCC4)cc3C(=O)Nc3ccn(-c4cccc(C(F)(F)F)c4)n3)c2)c1]

Into a 250-mL round bottom flask, was placed a solution of 2-(3-(chloromethyl)benzamido)-5-(piperidin-1-yl)-N-(1-(3-(trifluoromethyl)phenyl)-1H-pyrazol-3-yl)benzamide 21a (1.6 g, 2.56 mmol, 1.00 equiv) in tetrahydrofuran (100 mL), 3-mercaptobenzoic acid (390 mg, 2.53 mmol, 0.99 equiv), potassium iodide (21.2 mg, 0.13 mmol, 0.05 equiv), and N,N-diisopropylethylamine (660 mg, 5.12 mmol, 2.00 equiv). The resulting solution was stirred for 24 h at 40° C. in an oil bath. The reaction progress was monitored by TLC/LCMS. The resulting mixture was concentrated under vacuum. The resulting solution was diluted with 20 mL of $H_2O$, extracted with 3×20 mL of ethyl acetate and the organic layers combined. The resulting mixture was washed with 1×20 mL of hydrochloric acid (1 mol/L) and 3×20 mL of brine. The mixture was dried over anhydrous sodium sulfate. The residue was applied onto a silica gel column and eluted with ethyl acetate/petroleum ether (1:20-1:1). This resulted in 1.12 g (63%) of product as a yellow to green solid. $^1$H-NMR (400 MHz, $CDCl_3$, ppm): δ 11.68(s, 1H), 9.75(s, 1H), 8.60-8.56(d, J=9.2 Hz, 1H), 8.00(s, 1H), 7.91(s, 3H), 7.88-7.81(m, 2H), 7.80-7.79(d, J=2.1 Hz, 1H), 7.66-7.65(d, J=2.4 Hz, 4H), 7.53-7.38(m, 2H), 7.33-7.25(m, 1H), 7.10-7.08(m, 1H), 4.20 (s, 2H), 3.17(s, 4H), 1.69-1.54(m, 6H). MS (ES, m/z): 700 [M+H]$^+$.

Example 19

3-((3-((4-(Piperidin-1-yl)-2-((1-(3-(trifluoromethyl)phenyl)-1H-imidazol-4-yl)carbamoyl)phenyl)carbamoyl)benzyl)thio)propanoic acid

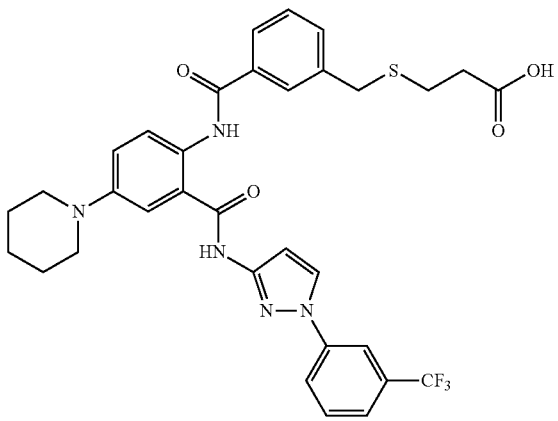 [SMILES: O=C(O)CCSCc1cccc(C(=O)Nc2ccc(N3CCCCC3)cc2C(=O)Nc2ccn(-c3cccc(C(F)(F)F)c3)n2)c1]

Into a 50-mL round bottom flask, was placed a solution of 2-amino-5-(piperidin-1-yl)-N-(1-(3-(trifluoromethyl)phenyl)-1H-imidazol-4-yl)benzamide 10f (140 mg, 0.26 mmol, 1.00 equiv, 80%) in dichloromethane (6 mL), 3-((3-tert-butoxy-3-oxopropylthio)methyl)benzoic acid (97 mg, 0.29 mmol, 1.00 equiv, 90%), EDC.HCl (125 mg, 0.65 mmol, 2.00 equiv), and 4-dimethylaminopyridine (80 mg, 0.66 mmol, 2.00 equiv). The resulting solution was stirred overnight at 28° C. The resulting solution was diluted with 60 mL of ethyl acetate. The resulting mixture was washed with 1×20 mL of 10% sodium bicarbonate and 1×20 mL of brine. The mixture was dried over sodium sulfate and concentrated under vacuum. The residue was applied onto a silica gel column and eluted with ethyl acetate/petroleum ether (1:1). This resulted in 140 mg (64%) of product as brown oil.

Into a 50-mL round bottom flask, was placed a solution of this solid (140 mg) in dichloromethane (5 mL), and 2,2,2-trifluoroacetic acid (1 mL). The resulting solution was stirred overnight at room temperature. The resulting mixture was concentrated under vacuum. The crude product (100 mg) was purified by reverse phase HPLC eluting with a water/$CH_3CN$ gradient containing 0.05% TFA. The product was obtained as 61.2 mg (51%) of a yellow solid. $^1$H-NMR (300 MHz, $CDCl_3$, ppm): δ 12.30 (s, 1H), 11.98 (s, 1H), 8.97 (d, J=9 Hz, 1H), 8.19 (m, 3H), 7.91 (s, 1H), 7.74 (m, 1H), 7.60 (m, 6H), 7.47 (m, 2H), 3.82 (s, 2H), 3.49 (m, 4H), 2.70 (m, 2H), 2.49 (m, 2H), 2.02 (m, 4H), 1.69 (m, 2H). MS (ES, m/z): 652 [M+H]$^+$

Example 20

4-((3-((4-(Piperidin-1-yl)-2-((1-(3-(trifluoromethyl)phenyl)-1H-pyrazol-3-yl)carbamoyl)phenyl)carbamoyl)benzyl)thio)benzoic acid Scheme 13. 1. 3-(chloromethyl)benzoyl chloride, DIPEA; 2 4-mercaptobenzoic acid, K₂CO₃, DMF, rt.

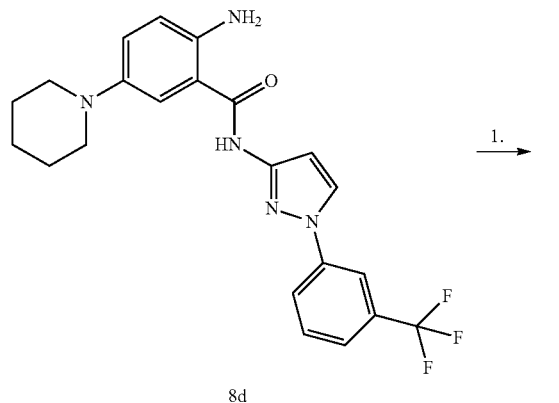

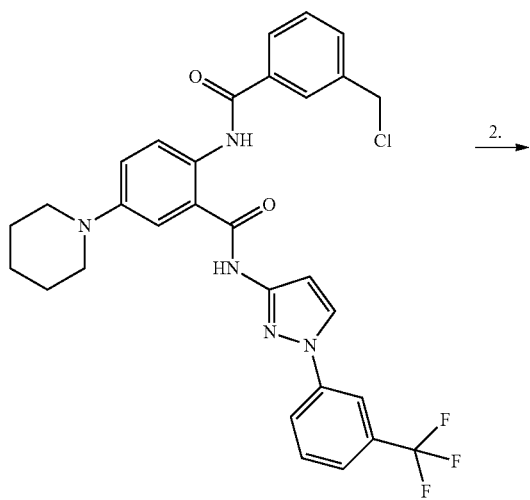

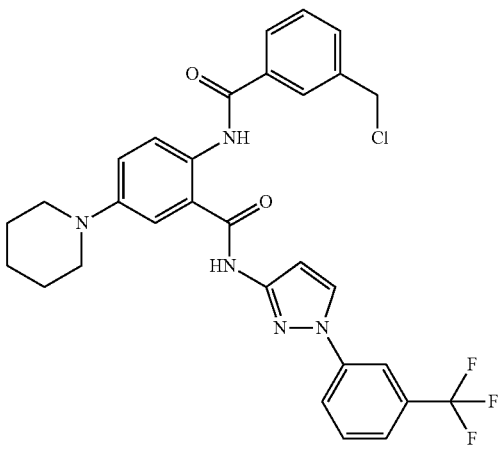 [SMILES: O=C(Nc1ccc(N2CCCCC2)cc1C(=O)Nc1ccn(-c2cccc(C(F)(F)F)c2)n1)c1cccc(CCl)c1]

Intermediate 21a 2-(3-(chloromethyl)benzamido)-5-(piperidin-1-yl)-N-(1-(3-(trifluoromethyl)phenyl)-1H-pyrazol-3-yl)benzamide A mixture of 100 mg of 2-amino-5-(piperidin-1-yl)-N-(1-(3-(trifluoromethyl)phenyl)-1H-imidazol-4-yl)benzamide and 119 mg of DIPEA, in 2 mL of 1:1 THF/dichloromethane was cooled to 0° C. and treated with 48 mg of 3-(chloromethyl)benzoyl chloride. After 30 minutes the solvent was evaporated. The residue was dissolved in dichloromethane, and the solution was washed with 3 N hydrochloric acid, then with an aqueous solution of sodium bicarbonate. The solution was dried (Na₂SO₄) and the solvent was evaporated.

Example 21

4-((3-((4-(piperidin-1-yl)-2-((1-(3-(trifluoromethyl)phenyl)-1H-pyrazol-3-yl)carbamoyl)phenyl)carbamoyl)benzyl)thio)benzoic acid Into a round bottom flask was placed a solution of intermediate 21a (0.0580 mmol, 1 equiv), 4-mercaptobenzoic acid (11 mg, 0.0696 mmol, 1.2 equiv), potassium carbonate (24 mg, 3 equiv), and DMF (1 mL). The solution was stirred at room temperature overnight. The solvent was evaporated at reduced pressure and the residue was partitioned between dichloromethane and water. The organic phase was dried (Na₂SO₄). The solvent was evaporated and the residue was purified by reverse phase HPLC eluting with 0.05% TFA in a water/acetonitrile gradient to give 34 mg of product. $^1$H-NMR (400 MHz, DMSO, ppm): δ 11.55(s, 1H), 11.48(s, 1H), 8.67(d, J=2.6 Hz, 1H), 8.32(d, J=8.3 Hz, 1H), 8.19(S, 1H), 8.16(d, J=7.8 Hz, 1H), 8.01(s, 1H), 7.85-7.71(m, 5H), 7.65(d, J=7.5 Hz, 3H), 7.52(t, J=7.7 Hz, 1H), 7.44(d, J=8.7 Hz, 2H), 7.04(d, J=2.7 Hz, 1H), 4.46(s, 2H), 3.30(s, 4H), 1.70(s, 4H), 1.59(s, 2H). MS (ES, m/z) 700 [M+H]⁺.

Example 21

N1-Methyl-N1-(2-morpholinoethyl)-N3-(2-((1-(3-(trifluoromethyl)phenyl)-1H-pyrazol-3-yl)carbamoyl)thiophen-3-yl)isophthalamide Scheme 14. 1. 2-nitro-5-(piperidin-1-yl)benzoic acid, DIPEA, HATU; 2. H₂, Pd/C; 3. HATU, DMF, DIEA, 3-(methyl(2-morpholinoethyl)carbamoyl)benzoic acid 1e..

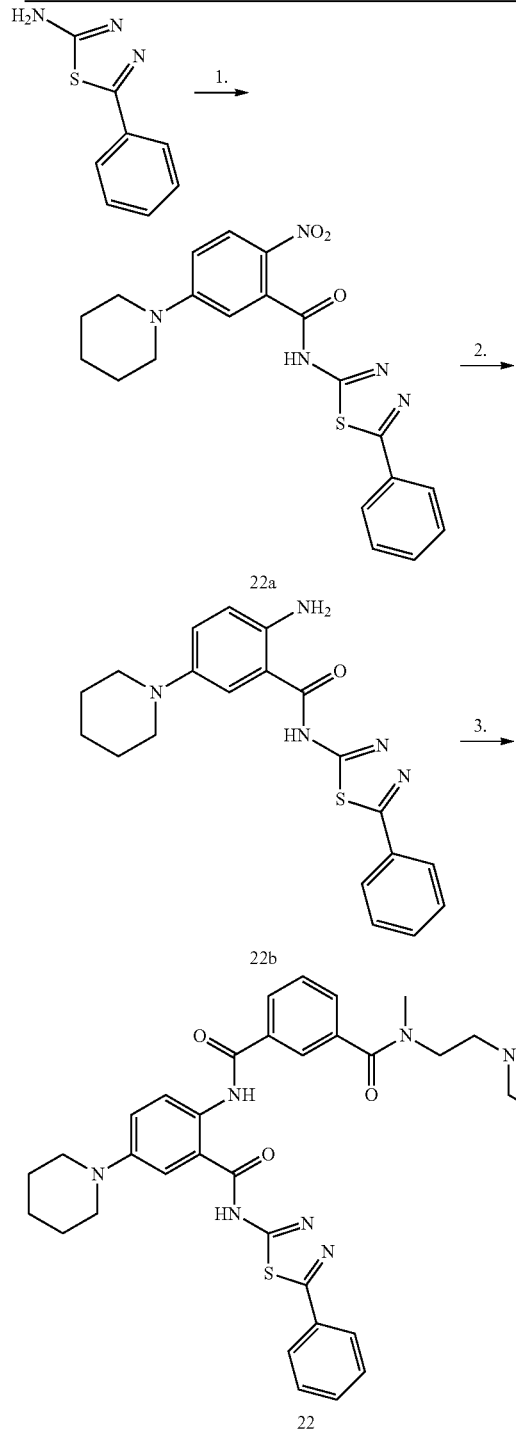

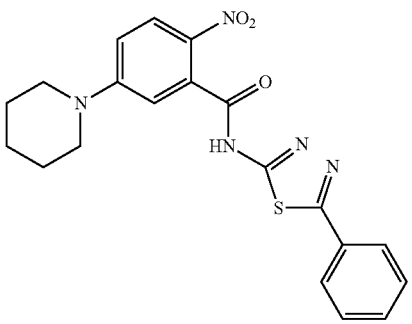 [SMILES: N=C(NC(=O)c1cc(N2CCCCC2)ccc1[N+](=O)[O-])SC(=N)c1ccccc1]

Intermediate 22a 2-nitro-N-(5-phenyl-1,3,4-thiadiazol-2-yl)-5-(piperidin-1-yl)benzamide A solution of 100 mg of 2-nitro-5-(piperidin-1-yl)benzoic acid, 78 mg of 2-amino-5-phenyl-1,3,4-thiazdiazole, and 153 µL of DIPEA in 0.8 mL of DMF was treated with 182 mg of HATU. After stirring for 16 h at 60° C. the mixture was diluted with ethyl acetate and washed with aqueous sodium bicarbonate solution and three times with water. The organic extracts were washed with brine and dried (Na₂SO₄). The solvent was evaporated and the residue was chromatographed on silica gel eluting with a gradient of 0% to 10% ethyl acetate in dichloromethane to give 137 mg of product. MS (ES, m/z) 410.0 [M+H]⁺.

Intermediate 22b 2-amino-N-(5-phenyl-1,3,4-thiadiazol-2-yl)-5-(piperidin-1-yl)-benzamide A solution of 130 mg of intermediate 22a in 2 mL of methanol and 6 mL of ethyl acetate was treated with 50 mg of 10% Pd/C (50% water by weight) and stirred under a hydrogen atmosphere for 3 hours. The mixture was diluted with dichloromethane and filtered. The solvent was evaporated to give 116 mg of yellow powder. MS (ES, m/z) 380.2 [M+H]⁺.

Example 22

N1-methyl-N1-(2-morpholinoethyl)-N3-(2-((1-(3-(trifluoromethyl)phenyl)-1H-pyrazol-3-yl)carbamoyl)thiophen-3-yl)isophthalamide Into a round bottom flask was placed a solution of aniline 22b (10 mg) and 3-(methyl(2-morpholinoethyl)carbamoyl)benzoic acid 1e (9 mg) in DMF (0.8 μL) and DIEA (17 μL). To this was added HATU at room temperature. The resulting solution was stirred overnight. The reaction progress was monitored by TLC/LCMS. The mixture was concentrated. The crude product was purified by reverse phase HPLC eluting with a water/$CH_3CN$ gradient containing 0.05% TFA to yield 8.6 mg of product. $^1$H-NMR (400 MHz, $CD_3OD$, ppm): δ 8.46-8.30 (m, 1H), 8.081-8.035(m, 2H), 7.97-7.92(b, 1H), 7.876-7.849(m, 2H), 7.711-7.692(m, 1H), 7.619(t, J=8 Hz, 1H), 7.522-7.470(m, 1H), 7.460-7.435(m, 3H), 3.873-3.859 (m, 3H), 3.82-3.49(b, 4H), 3.431-3.378(m, 6H), 3.051(s, 3H), 1.837-1.825(m, 4H), 1.668, 1.639(m, 2H). MS (ES, m/z): 654 $[M+H]^+$.

Example 22

2-(3-((3-((4-(Piperidin-1-yl)-2-((1-(3-(trifluoromethyl)phenyl)-1H-pyrazol-3-yl)carbamoyl)phenyl)carbamoyl)benzyl)thio)phenyl)acetic acid

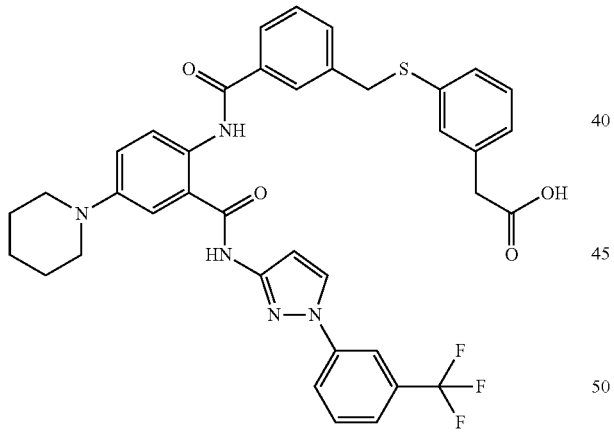

Into a round bottom flask was placed a solution of 2-(3-(chloromethyl)benzamido)-5-(piperidin-1-yl)-N-(1-(3-(trifluoromethyl)phenyl)-1H-pyrazol-3-yl)benzamide 21b (0.23 mmol, 1 equiv) in DMF (1.2 mL), potassium carbonate (127.1 mg, 0.92 mmol, 4 equiv), and (3-mercaptophenyl)acetic acid (42.6 mg, 0.253 mmol, 1.1 equiv). The solution was stirred overnight at room temperature. The reaction progress was monitored by LCMS. After 16.5 h, more (3-mercaptophenyl) acetic acid (7 mg) was added to the solution, and the solution was stirred another 1 h. The solvent was removed. The residue was dissolved with DCM, washed with $H_2O$ and brine, and dried over sodium sulfate. The product was purified by reverse phase HPLC, eluting with 0.05% TFA in a water/acetonitrile gradient. MS (ES, m/z) 714 $[M+H]^+$.

Example 23

2-(3-((3-((4-Chloro-2-((1-(3-(trifluoromethyl)phenyl)-1H-pyrazol-3-yl)carbamoyl)phenyl)carbamoyl)benzyl)thio)phenyl)acetic acid Scheme 15. 1. DIPEA, DCM/THF;
2. (3-mercaptophenyl)acetic acid, $K_2CO_3$, DMF, rt.

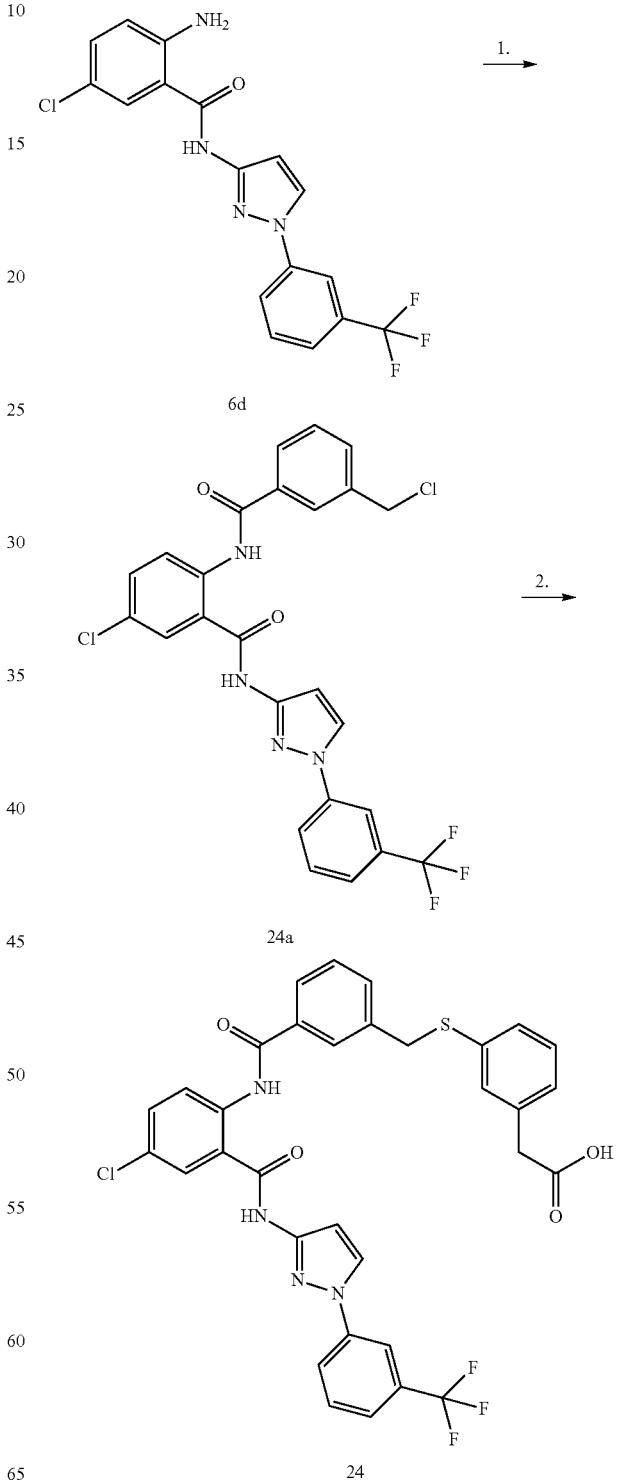

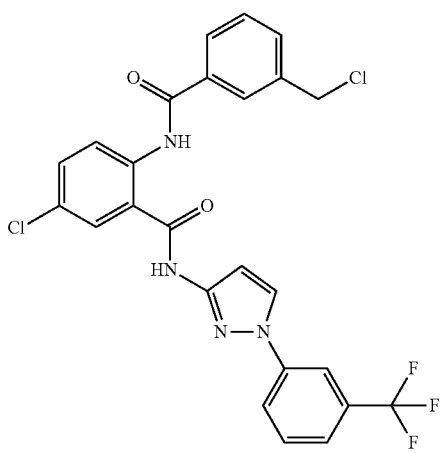 [SMILES: O=C(Nc1ccc(Cl)cc1C(=O)Nc1ccn(-c2cccc(C(F)(F)F)c2)n1)c1cccc(CCl)c1]

Intermediate 24a 2-amino-5-chloro-N-(1-(3-(trifluoromethyl)phenyl)-1H-pyrazol-3-yl)-benzamide Into a round bottom flask was placed a solution of 2-amino-5-chloro-N-(1-(3-(trifluoromethyl)phenyl)-1H-pyrazol-3-yl)benzamide 6d (250 mg) in dichloromethane (2 mL) and tetrahydrofuran (2 mL), and DIPEA (378 mg). The solution was cooled to 0° C. To this was added dropwise 3-(chloromethyl)benzoyl chloride (726 mg). The solution was warmed to room temperature, and stirred for 30 min, and then diluted with dichloromethane. The resulting solution was washed with 5% hydrochloric acid, an aqueous solution of $NaHCO_3$, and $H_2O$, then dried over sodium sulfate. The solvent was removed and the crude product was used directly in the next step.

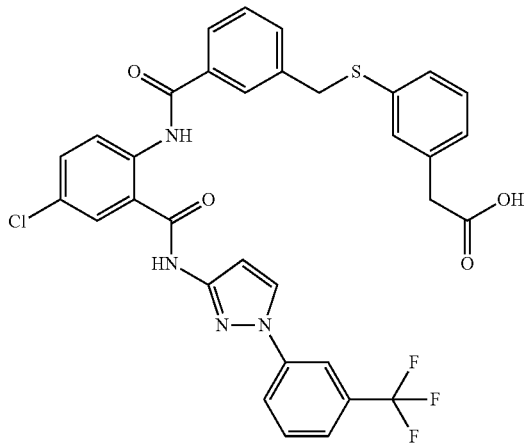 [SMILES: O=C(O)Cc1cccc(SCc2cccc(C(=O)Nc3ccc(Cl)cc3C(=O)Nc3ccn(-c4cccc(C(F)(F)F)c4)n3)c2)c1]

Example 24

2-(3-((3-((4-chloro-2-((1-(3-(trifluoromethyl)phenyl)-1H-pyrazol-3-yl)-carbamoyl)phenyl)carbamoyl)benzyl)thio)phenyl)acetic acid Into a round bottom flask was placed a solution of intermediate 24a (195 mg) in DMF (4 mL), potassium carbonate (152 mg), and (3-mercaptophenyl)acetic acid (68 mg). The solution was stirred overnight at room temperature. The mixture was filtered and the solvent was evaporated at reduced pressure. The product was purified by reverse phase HPLC, eluting with 0.05% TFA in a water/acetonitrile gradient to yield 84 mg (35%) of product. MS (ES, m/z) 663 [M+H]$^+$.

Example 24

1-(3-((4-Chloro-2-((1-(3-(trifluoromethyl)phenyl)-1H-pyrazol-3-yl)carbamoyl)phenyl)carbamoyl)phenyl)-1-oxo-5,8,11-trioxa-2-azatetradecan-14-oic acid Scheme 16. 1. tert-butyl 3-(2-(2-(2-(tosyloxy)ethoxy)ethoxy)ethoxy)propanoate 8b, HATU, 2. oxalyl chloride, DIEA; 3. 2-amino-5-chloro-N-(1-(3-(trifluoromethyl)phenyl)-1H-pyrazol-3-yl)benzamide 6d, pyridine; 4. TFA, DCM.

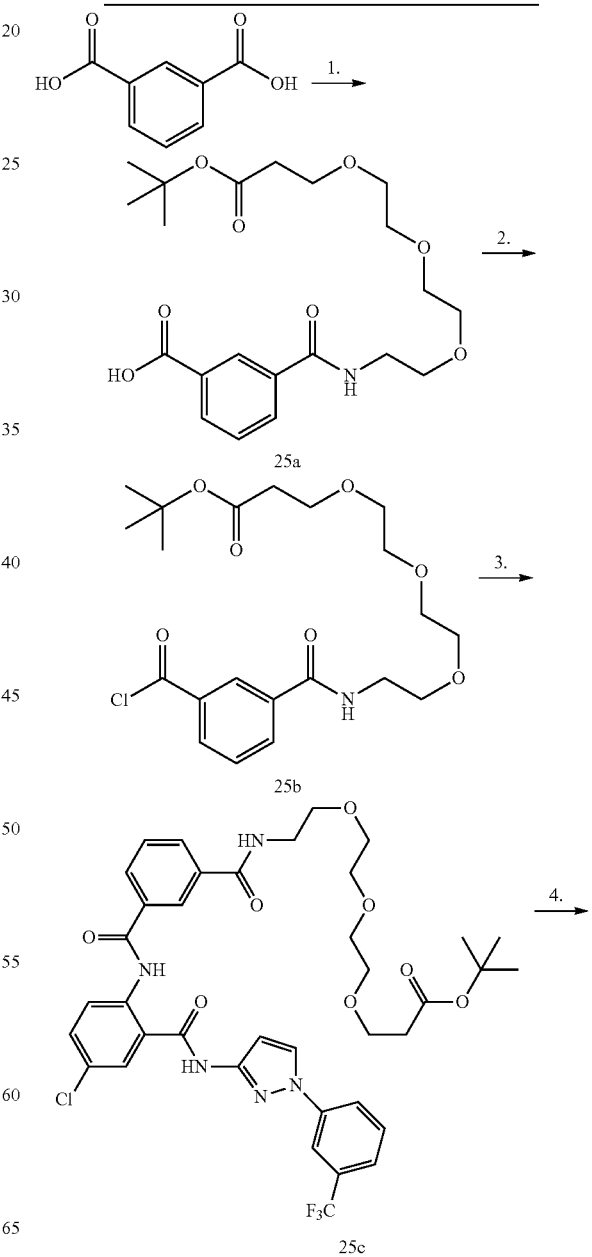

101

-continued

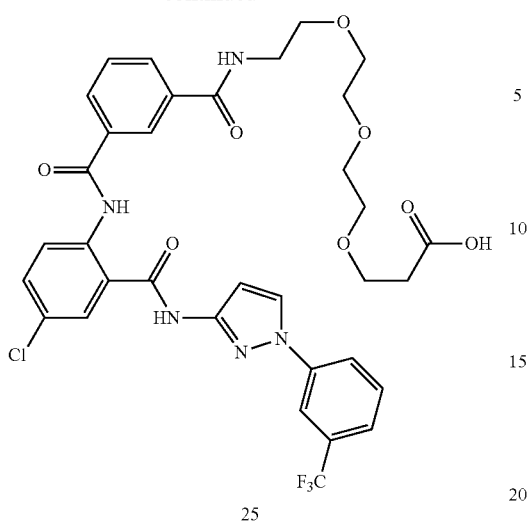

25

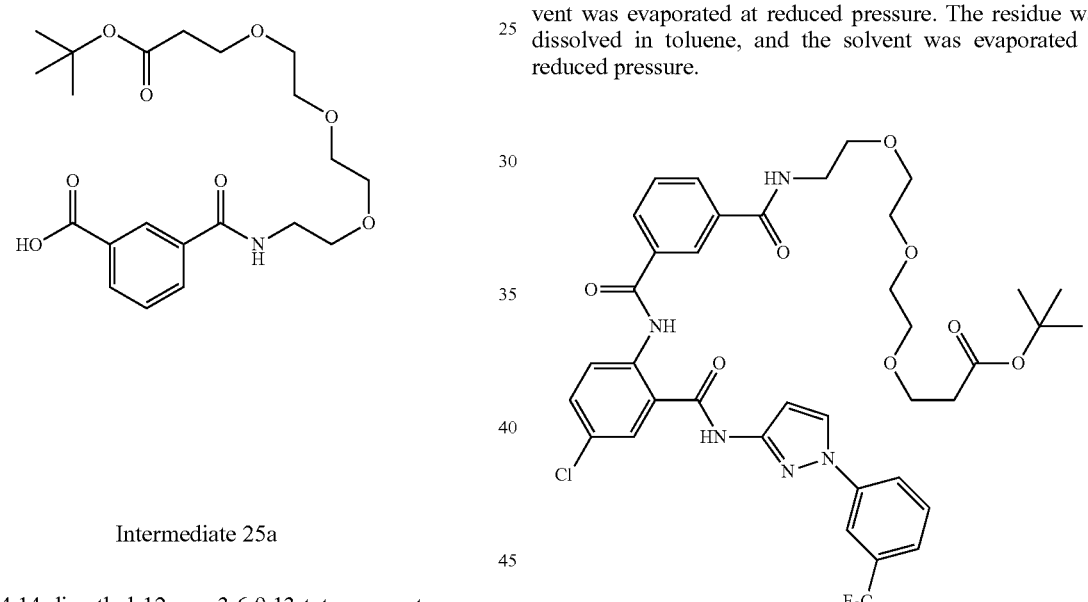

Intermediate 25a 3-((14,14-dimethyl-12-oxo-3,6,9,13-tetraoxapentadecyl)carbamoyl)-benzoic acid Into a 50-mL round-bottom flask, was placed a solution of isophthalic acid (1.7 g, 10.24 mmol, 2.98 equiv) in dichloromethane (10 mL), EDC.HCl (660 mg, 3.44 mmol, 1.00 equiv), 4-dimethylaminopyridine (420 mg, 3.44 mmol, 1.00 equiv), and tert-butyl 3-(2-(2-(2-(methylamino)ethoxy)ethoxy)ethoxy)propanoate 8b (1 g, 3.44 mmol, 1.00 equiv). The resulting solution was stirred for 2 h at room temperature. The resulting mixture was washed with 2×20 mL of water and 1×20 mL of NH$_4$Cl (aq). The mixture was dried over sodium sulfate and concentrated under vacuum. The crude product (1 g) was purified by reverse phase chromatography with a water/methanol gradient to yield 500 mg (33%) of 3-(14,14-dimethyl-12-oxo-3,6,9,13-tetraoxapentadecyl)carbamoyl) benzoic acid. as yellow oil. $^1$H-NMR (300 MHz, CD$_3$OD, ppm): δ 8.087(s, 2H), 7.664-7.560(m, 2H), 3.785-3.499(m, 14H), 3.144-3.705(m, 3H), 2.489-2.448(m, 2H), 1.469-1.456 (s, 9H). MS (ES, m/z): 440 [M+H]$^+$.

102

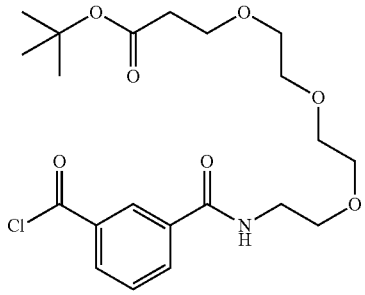 [SMILES: CC(C)(C)OC(=O)CCOCCOCCOCCNC(=O)c1cccc(C(=O)Cl)c1]

Intermediate 25b tert-butyl 1-(3-(chlorocarbonyl)phenyl)-1-oxo-5,8,11-trioxa-2-azatetradecan-14-oate A solution of 68 mg of intermediate 25a and 35 μL of diisopropylethylamine in 1 mL of dichloromethane was treated with 18 μL of oxalyl chloride followed by 5 μL of DMF. The mixture was stirred 30 minutes and then the solvent was evaporated at reduced pressure. The residue was dissolved in toluene, and the solvent was evaporated at reduced pressure.

Intermediate 25c tert-butyl 1-(3-((4-chloro-2-((1-(3-(trifluoromethyl) phenyl)-1H-pyrazol-3-yl)carbamoyl)phenyl)carbamoyl)phenyl)-1-oxo-5,8,11-trioxa-2-azatetradecan-14-oate The residue from the preceding step was dissolved in 1 mL of a 1:1 mixture of dichloromethane and THF. The solution was treated with 57 mg of 2-amino-5-chloro-N-(1-(3-(trifluoromethyl)phenyl)-1H-pyrazol-3-yl)benzamide 6d followed by 78 μL of diisopropylethylamine After 1 hour the mixture was partitioned between dichloromethane and an aqueous solution of sodium bicarbonate. The solution was dried (Na$_2$SO$_4$) and the solvent was evaporated at reduced pressure. The residue was purified by silica gel chromatography eluting with a gradient of 0% to 100% ethyl acetate in dichloromethane. This gave 37 mg of product.

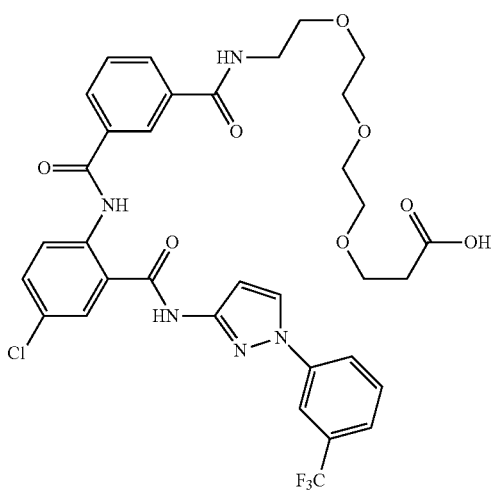 [SMILES: O=C(O)CCOCCOCCOCCNC(=O)c1cccc(C(=O)Nc2ccc(Cl)cc2C(=O)Nc2ccn(-c3cccc(C(F)(F)F)c3)n2)c1]

Example 25

1-(3-((4-chloro-2-((1-(3-(trifluoromethyl)phenyl)-1H-pyrazol-3-yl)-carbamoyl)phenyl)carbamoyl)phenyl)-1-oxo-5,8,11-trioxa-2-azatetradecan-14-oic acid Into a round bottom flask was placed a solution of intermediate 25c (96 mg) in dichloromethane (0.5 mL). To this was added trifluoroacetic acid (0.5 mL). The solution was stirred for 30 min, and then diluted with dichloromethane. The solvent was evaporated and the residue was purified by reverse phase HPLC, eluting with 0.05% TFA in a water/acetonitrile gradient yielding 93 mg of product. $^1$H-NMR (400 MHz, CD$_3$OD, ppm): δ 8.59 (d, J=9.2 Hz, 1H), 8.33 (d, J=2.5 Hz, 1H), 8.13 (s, 1H), 8.04 (d, J=8.2 Hz, 3H), 7.97 (d, J=2.5 Hz, 1H), 7.67-7.54 (m, 5H), 7.03 (d, J=2.4 Hz, 1H), 3.76 (s, 2H), 3.64-3.46 (m, 14H), 3.12-3.09 (m, 3H), 2.46 (t, J=6.3 Hz, 2H). MS (ES, m/z) 768 [M+Na]$^+$.

Example 25

2-Oxo-1-(3-((3-((4-(piperidin-1-yl)-2-((1-(3-(trifluoromethyl)phenyl)-1H-pyrazol-3-yl)carbamoyl)phenyl)carbamoyl)benzyl)thio)phenyl)-6,9,12-trioxa-3-azapentadecan-15-oic acid

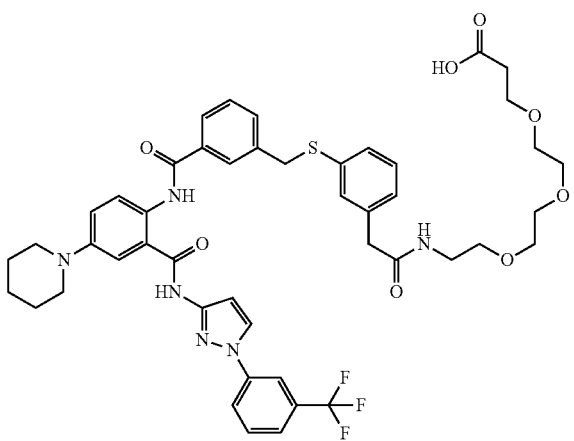 [SMILES: O=C(O)CCOCCOCCOCCNC(=O)Cc1cccc(SCc2cccc(C(=O)Nc3ccc(N4CCCCC4)cc3C(=O)Nc3ccn(-c4cccc(C(F)(F)F)c4)n3)c2)c1]

Into a round bottom flask was placed a solution of 2-(3-((3-((4-(piperidin-1-yl)-2-((1-(3-(trifluoromethyl)phenyl)-1H-pyrazol-3-yl)carbamoyl)phenyl)carbamoyl)benzyl)thio)-phenyl)acetic acid 23 (0.119 mmol, 1 equiv) in acetonitrile (0.5 mL), and DIPEA (78.9 mg, 0.612 mmol, 4 equiv). To this was added a solution of tert-butyl 3-(2-(2-(2-(methylamino)ethoxy)ethoxy)ethoxy)propanoate 8b (33.08 mg, 0.127 mmol, 1.1 equiv) in acetonitrile (0.5 mL), followed by HATU (57.9 mg, 0.153 mmol, 1.2 equiv). The mixture was stirred at room temperature. The reaction progress was monitored by LCMS. After 1 h, more 8b (15 mg) was added to the solution, and the solution was stirred another 30 min. The solvent was removed by evaporation at reduced pressure. The residue was dissolved in DCM (1 mL). To this was added TFA (0.5 mL). The solution was stirred for 1 h and then the solvent was evaporated at reduced pressure. The crude product was purified by reverse phase HPLC eluting with a water/CH$_3$CN gradient containing 0.05% TFA. Lyophilization gave 37 mg of product. $^1$H NMR (400 MHz, dmso) δ 1.55 (s, 1H), 11.46 (s, 1H), 8.65 (d, J=2.6 Hz, 1H), 8.33 (d, J=8.5 Hz, 1H), 8.16 (s, 1H), 8.12 (d, J=7.9 Hz, 1H), 8.05 (t, J=5.2 Hz, 1H), 7.94 (s, 1H), 7.78-7.67 (m, 3H), 7.61 (d, J=7.5 Hz, 2H), 7.55 (d, J=7.4 Hz, 1H), 7.45 (t, J=7.7 Hz, 1H), 7.22 (s, 1H), 7.17 (d, J=4.9 Hz, 3H), 7.01 (s, 3H), 4.30 (s, 3H), 3.54 (t, J=6.4 Hz, 4H), 3.43 (s, 14H), 3.41-3.16 (m, 15H), 3.16-3.09 (m, 3H), 2.39 (t, J=6.4 Hz, 3H), 1.76-1.66 (m, 4H), 1.61-1.52 (m, 2H).MS (ES, m/z) 917 [M+H]$^+$.

Example 26

Procedure for the Measurement of NaP2b-mediated P$_i$ Transport

Materials. HEK293 cells were obtained from the American Type Culture collection and propagated per their instructions. Expression clones for rat and human NaP2b (SLC34A2) were obtained from Open Biosystems (Catalog numbers MRN1768-9510282, and MHS1010-99823026, respectively). The sequence of the human protein was mutated to insert a threonine after residue 37, and to introduce a N39D mutation.

Inhibition of P$_i$ Transport. The rate of phosphate (Pi) uptake into HEK293 cells was measured using a modification of the method described by Mohrmann et al. (Mohrmann, I., Mohrmann, M., Biber, J., and Murer, H. (1986) *Am. J. Phys.* 250(3 Pt 1):G323-30.) Transfected HEK293 cells were treated with a pharmacological agent to minimize endogenous PiT-mediated phosphate transport activity, such that the only remaining sodium-dependent phosphate transport activity is that which was bestowed by introduction of the NaP2b genes.

Cells were seeded into 96-well plates at 25,000 cells/well and cultured overnight. Lipofectamine 2000 (Invitrogen) was used to introduce the NaP2b cDNA, and the cells were allowed to approach confluence during a second overnight incubation. Medium was aspirated from the cultures, and the cells were washed once with choline uptake buffer (14 mM Tris, 137 mM choline chloride, 5.4 mM KCl, 2.8 mM CaCl$_2$, 1.2 mM MgSO$_4$, 100 uM KH$_2$PO$_4$, 1 mg/mL Bovine Serum Albumin, pH 7.4). Cells were then overlayed with either choline uptake buffer or sodium uptake buffer (14 mM Tris, 137 mM sodium chloride, 5.4 mM KCl, 2.8 mM CaCl$_2$, 1.2 mM MgSO$_4$, 100 uM KH$_2$PO$_4$, PiT-silencing agent, 1 mg/mL Bovine Serum Albumin, pH 7.4) containing 6-9 uCi/mL $^{33}$P orthophosphoric acid (Perkin Elmer) and test compound. Each compound was tested at twelve concentrations ranging from 0.1 nM to 30 uM. Assays were run in duplicate.

After incubation for 3-30 minutes at room temperature, assay mixtures were removed, and the cells were washed twice with ice cold stop solution (137 mM sodium chloride, 14 mM Tris, pH 7.4). Cells were lysed by addition of 20 μL 0.1% Tween 80 followed by 100 μL scintillation fluid, and counted using a TopCount (Perkin Elmer).

pIC50 (the negative log of the IC50) values of the test compounds were calculated using GraphPad Prism. Preliminary studies showed that under these conditions, sodium-dependent Pi uptake was linear for at least 30 min and tolerated 0.6% (v/v) DMSO without deleterious effects.

To ascertain if an inhibitor was competitive for binding with phosphate, the procedure was repeated, but raising the concentration of the substrate in the assay mixture from 0.1 to 2.1 mM phosphate. Compounds that maintained their potency for inhibition of NaPi2b in the presence of 2.1 vs 0.1 mM phosphate were considered to not be competitive with respect to phosphate.

TABLE 2

Inhibitory Activity of Compounds Against Rat and Human NaP2b Values Reported a pIC50.

| Example | pIC50 range for rat Nap2b | pIC50 range for human Nap2b* | Competitive with respect to Pi?** |
|---|---|---|---|
| PFA | 2-3 | — | Yes |
| 1 | >6.0 | >6.0 | — |
| 2 | 5.1-6.0 | — | — |
| 3 | >6.0 | — | — |
| 4 | 5.1-6.0 | — | — |
| 5 | 5.1-6.0 | — | — |
| 6 | 5.1-6.0 | — | — |
| 7 | 5.1-6.0 | 5.1-6.0 | — |
| 8 | 5.1-6.0 | — | — |
| 9 | 4.5-5.0 | — | — |
| 10 | 5.1-6.0 | — | — |
| 11 | >6.0 | >6.0 | No |
| 12 | 4.5-5.0 | — | — |
| 13 | 5.1-6.0 | — | — |
| 14 | >6.0 | >6.0 | — |
| 15 | 5.1-6.0 | >6.0 | — |
| 16 | 5.1-6.0 | — | — |
| 17 | 5.1-6.0 | 5.1-6.0 | — |
| 18 | 5.1-6.0 | — | No |
| 19 | 5.1-6.0 | — | — |
| 21 | 5.1-6.0 | — | — |
| 22 | 5.1-6.0 | — | — |
| 23 | >6.0 | >6.0 | — |
| 24 | >6.0 | — | — |
| 25 | >6.0 | >6.0 | — |
| 26 | >6.0 | >6.0 | No |

*A blank indicates not tested
**Indicates compound is considered to not be competitive with respect to phosphate. A blank indicates not tested for competitive inhibition.

Example 27

In vivo Assay: Bolus Phosphorus Challenge

It has been demonstrated that the hyperphosphatemic response to a single oral dose of phosphorus is significantly dampened in mice deficient in the Nap2b gene (Sabbagh et al, J. Am Soc Nephroi., 20(11):2348-58 (2009)). By pretreating animals with a low phosphorus diet followed by the subsequent dosing of a phosphorus bolus, serum phosphorus levels were monitored after 30 minutes as a surrogate for intestinal phosphorus absorption. These investigators showed that as a result of Np2b deletion, the rise in serum phosphorus was reduced by about 40%. This indicates that the theoretical maximum effect on phosphorus absorption a Nap2b inhibitor could have in mice is 40% as indicated by the serum Pi. The in vivo bolus phosphorus challenge model used here mimics this model in rats.

Male, 7-week-old Sprague-Dawley rats (Charles-River laboratories international, Hollister, Calif.) were allowed to acclimatize for a minimum of 3 days before switching to a synthetic low-phosphorus diet (TD.85010, Harlan Teklad, Madison, Wis.) which contains 0.1% phosphorus and 0.6% calcium. At day 5, testing compounds or vehicle alone (as indicated) were orally administered at the indicated dose in a volume of 5 ml/kg, followed by a bolus gavage of monobasic sodium phosphate (1 mmol in 1 ml) 15 min after compound dosing. Serum was collected via retroorbital bleeding 30 min post phosphate bolus and phosphate levels were determined utilizing an ACE ALERA blood chemistry analyzer (Alfa Wassermann Diagnostic Technologies, West Caldwell, N.J.).

The extent of inhibition by test compounds on the elevation of serum phosphate levels in response to the bolus of phosphate is shown in Table 3 (data are expressed as % Inhibition, with 6-10 animals per data point). The differences between groups were evaluated by one-way analysis of variance with Dunnett's post hoc tests.

TABLE 3

Inhibition of Uptake of Phosphate from the Intestine as Measured using the Bolus Phosphate Challenge Model

| Example | Drug Dose | % Inhibition of Serum P elevation | Significance |
|---|---|---|---|
| 11 | 30.0 | 30.0 | *** |
| 7 | 30 | 49 | *** |

*$p < 0.05$, versus vehicle by Dunnett's post hoc test.
**$p < 0.01$, versus vehicle by Dunnett's post hoc test.
***$p < 0.001$, versus vehicle by Dunnett's post hoc test.

Example 28

In vivo Evaluation Procedure: Co-dosing in Chow

Male, 7-week-old Sprague-Dawley rats (Charles-River laboratories international, Hollister, Calif.) were allowed to acclimate for a minimum of 3 days. The experiment was initiated by switching animals to a synthetic diet (0.6% phosphorus and 0.6% calcium, Harlan Teklad TD.84122) for four days. After this time, the animals were placed into metabolic cages for daily monitoring of food and water consumption, as well as urine and fecal collections. Test compounds were incorporated into the powdered diet listed above containing 3% chocolate flavoring (w/w, BioSery #7345) at 1.3 mg test compound per gram of diet to achieve an average daily nominal dose of 100 mg/kg/day. The actual dose received by each animal was later determined by measuring prepared diet consumption and body weight. Urine samples were collected in three daily periods from 24-48, 48-72, and 72-96 hours of drug dosing. Averaging these three 24 h periods allows for the more representative measurements of urination, fecal excretion, food consumption and water uptake for each animal. Phosphorous levels in the urine were determined by anion exchange chromatography using a Dionex ICS-3000 ion chromatography system. Urine samples were diluted 1:500 or 1:1000 and injected onto an IonPac AS18 analytical column (2×250 mm) using a potassium hydroxide eluent. Elution of urine phosphate ions was monitored via conductivity detector and reported as ppm relative to a standard ion solution containing phosphate. Daily urinary P output relative to the P consumed in the prepared diet for each animal was calculated.

The percentage inhibition of phosphorus absorption was estimated by determining the reduction of this ratio compared to the control group (animals with no drug in chow). The differences between the means of control and treated groups were evaluated by t tests. In all experiments, one group was always included that had Renvela powder blended into their chow at 0.9% targeting a dose of 750 mg/kg. Typically this resulted in an approximately 15% inhibition of Urine Pout/P consumed.

TABLE 4

Inhibition of Uptake of Phosphorus from the Intestine as Measured using the Co-Dosing in Chow Model

| Example | Mean drug dose, mg/kg/day | Mean % inhibition Urine Pout/P consumed | t-test |
|---|---|---|---|
| 14 | 105 | 12 | *** |
| 15 | 104 | 9 | ** |

*p < 0.05 versus control;
**p < 0.05 versus control;
***p < 0.05 versus control

Example 29

Stability of Compounds in Simulated Gastric and Intestinal Fluid

Test compounds were incubated at 1-20 µM in simulated gastric fluid (SGF; standard USP solution with 3 mg/mL pepsin) or simulated intestinal fluid (SIF; standard USP solution with 3 mg/mL pancreatin) for 3 hr or 6 hr. HPLC-UV or HPLC-MS were used to determine test compound levels using peak area %. Results (Table 5) were reported as the percentage of test compound remaining after incubation in a given condition relative to test compound present at t=0 in the same condition.

TABLE 5

Percentage of Compound Remaining in Simulated Gastric and Intestinal Fluids

| Example | Incubation Time | % remaining, SIF | % remaining, SGF |
|---|---|---|---|
| 26 | 6 hr | 95 | 91 |
| 14 | 6 hr | 72 | 93 |
| 25 | 6 hr | 95 | 58 |
| 15 | 6 hr | 97 | 100 |

Example 30

Determination of Compound Cmax and AUC

Sprague-Dawley rats were orally gavaged with test article at a nominal dose of 2.5 or 10 mg/kg and blood was collected at 0.5, 1, 2 and 4 h. Blood samples were processed to plasma using $K_2EDTA$ as an anticoagulant. Plasma samples were treated with acetonitrile containing an internal standard, precipitated proteins removed by centrifugation. Supernatants were analyzed by LC-MS/MS and compound concentrations were determined by interpolated from a standard curve prepared in plasma. Table 6 illustrates data from the pharmacokinetic profiling of selected example compounds. All compounds were orally dosed at the dosage shown, and pharmacokinetic parameters determined

TABLE 6

Pharmacokinetic Profiling of Selected Example Compounds

| Example | Actual Oral Dose (mg/kg) | LLOQ (ng/mL) | Cmax (ng/mL) | AUC (ng × hr/mL) |
|---|---|---|---|---|
| 26 | 9.3 | 0.5 | 3 | <3.0 |
| 14 | 10 | 5 | 487 | 788 |
| 25 | 9.7 | 0.5 | 3 | <3.0 |
| 15 | 11 | 0.5 | 10 | 11 |
| 18 | 7.6 | 5.0 | 1821 | 6050 |
| 18 | 1.9 | 0.5 | 678 | 2127 |
| 11 | 10 | 1 | 5 | 9.8 |
| 7 | 8.7 | 5 | 393 | 467.2 |

LLOQ = Lower Limit of Quantification

Example 31

Fecal Recovery of Orally Administered Compounds

Quantitative determination of test compound level in feces after oral gavage was performed using the same set of animals used to determine test compound concentration in plasma (Example 30). The animals were kept in metabolic cages and feces were collected from the time of dosing until 48 hr after dosing. Upon collection, feces was dried by lyophilization and ground to a visually homogenous powder. Duplicate samples of ground feces from each individual animal were weighed out and extracted using organic solvent. Extracted samples were then diluted into mobile phase and test compound levels were quantitatively determined by LC-MS/MS analysis as described in "Example 30" except that the standard curve was prepared in a feces matrix. Extraction conditions were not optimized for individual compounds, and thus may represent a minimal level of recovery.

TABLE 7

Fraction of Orally Administered Compound Recovered in Feces 48 Hours after Dosing

| Example | % recovered in feces |
|---|---|
| 26 | 9.5 |
| 14 | 6.6 |
| 25 | 17 |
| 15 | 17 |
| 18* | 60 |
| 18** | 12 |
| 11 | 47 |
| 7 | 9.5 |

*Dosed at 7.6 mg/kg (see Example 30)
**Dosed at 1.9 mg/kg (see Example 30)

All of the U.S. patents, U.S. patent application publications, U.S. patent applications, foreign patents, foreign patent applications and non-patent publications referred to in this specification are incorporated herein by reference, in their entirety to the extent not inconsistent with the present description.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A pharmaceutical composition comprising:
a compound of structure (I):

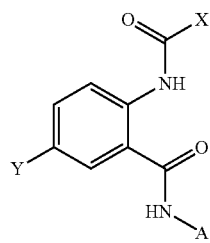

or a stereoisomer or pharmaceutically acceptable salt thereof,
wherein:
A is:

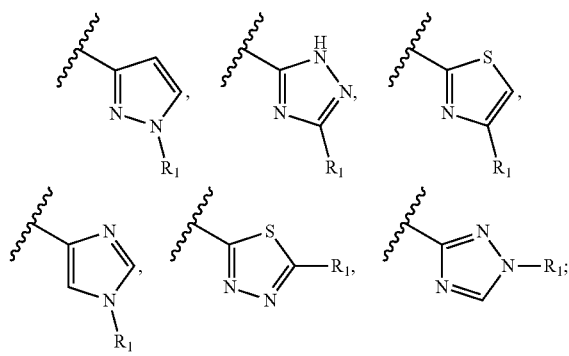

X is substituted aryl or substituted heteroaryl;
Y is halogen, optionally substituted alkylamino, optionally substituted alkoxy, optionally substituted thioalkyl, optionally substituted cycloalkyl, optionally substituted heterocyclyl, optionally substituted aryl, —O(optionally substituted cycloalkyl), —O(optionally substituted heterocyclyl) or —O(optionally substituted aryl); and
$R_1$ is optionally substituted aryl or optionally substituted heteroaryl; and
a pharmaceutically acceptable carrier, diluent, or excipient.

2. The pharmaceutical composition of claim 1 wherein Y is halogen.

3. The pharmaceutical composition of claim 2 wherein Y is chloro.

4. The pharmaceutical composition of claim 1 wherein Y is alkylamino.

5. The pharmaceutical composition of claim 4 wherein Y is diethylamino.

6. The pharmaceutical composition of claim 1 wherein Y is alkoxy.

7. The pharmaceutical composition of claim 1 wherein Y is heterocyclyl.

8. The pharmaceutical composition of claim 7 wherein Y is 1-piperidinyl and the compound has the structure:

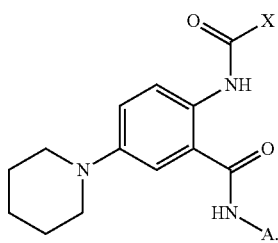

9. The pharmaceutical composition of claim 1 wherein Y is —O(cycloalkyl).

10. The pharmaceutical composition of claim 1 wherein X is —$ZR_2$, and wherein Z is aryl or heteroaryl and $R_2$ is a non-hydrogen substituent.

11. The pharmaceutical composition of claim 10 wherein Z is aryl.

12. The pharmaceutical composition of claim 11 wherein Z is phenyl.

13. The pharmaceutical composition of claim 12 wherein the compound has the structure:

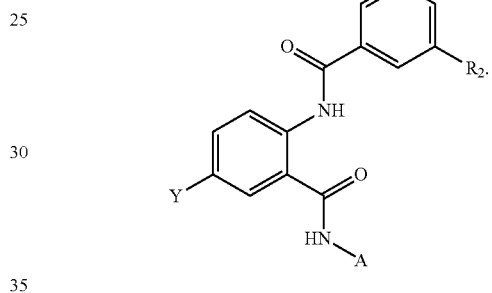

14. The pharmaceutical composition of claim 10 wherein Z is heteroaryl.

15. The pharmaceutical composition of claim 14 wherein Z is pyridinyl.

16. The pharmaceutical composition of claim 15 wherein the compound has the structure:

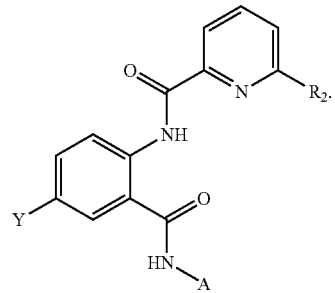

17. The pharmaceutical composition of claim 10 wherein $R_2$ is:
(a) —$CH_2S(O)_{0-2}$(optionally substituted $C_{1-6}$alkyl)C(=O)$NR_6R_3$,
(b) —$CH_2S(O)_{0-2}$(optionally substituted $C_{1-6}$alkyl)$NR_6R_3$,
(c) —$CH_2S(O)_{0-2}$(optionally substituted $C_{1-6}$alkyl)C(=O)$OR_4$,
(d) —$CH_2S(O)_{0-2}$(optionally substituted $C_{1-6}$alkyl)$OR_4$,
(e) —$CH_2S(O)_{0-2}$(optionally substituted $C_{1-6}$alkyl)$R_5$,
(f) —$CH_2S(O)_{0-2}R_5$,
(g) —$CH_2S(O)_{0-2}NR_6R_3$,
(h) —$CH_2S(O)_{0-2}(CH_2CH_2O)_xR_4$, (i) CH₂NR₆(CH₂CH₂O)ₓR₄,
(j) —C(=O)NR₆(optionally substituted C₁₋₆alkyl)C(=O)NR₆R₃,
(k) —C(=O)NR₆(optionally substituted C₁₋₆alkyl)NR₆R₃,
(l) —C(=O)NR₆(optionally substituted C₁₋₆alkyl)C(=O)OR₄,
(m) —C(=O)NR₆(optionally substituted C₁₋₆alkyl)OR₄,
(n) —C(=O)NR₆(optionally substituted C₁₋₆alkyl)R₅, or
(o) —C(=O)NR₆(CH₂CH₂O)ₓR₄;
wherein
R₃ is hydrogen, hydroxyl, alkoxy, optionally substituted C₁₋₆alkyl, optionally substituted aryl, optionally substituted heterocyclyl or optionally substituted heteroaryl;
R₄ is hydrogen, optionally substituted C₁₋₆alkyl, optionally substituted aryl, optionally substituted heterocyclyl or optionally substituted heteroaryl;
R₅ is optionally substituted aryl, optionally substituted heterocyclyl or optionally substituted heteroaryl;
R₆ is hydrogen or optionally substituted C₁₋₆alkyl; and
x is an integer from 2 to 10.

18. The pharmaceutical composition of claim 1 wherein A is:

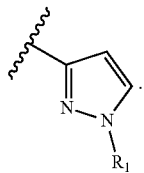

19. The pharmaceutical composition of claim 1 wherein A is:

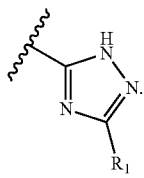

20. The pharmaceutical composition of claim 1 wherein A is:

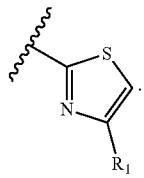

21. The pharmaceutical composition of claim 1 wherein A is:

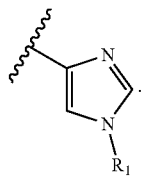

22. The pharmaceutical composition of claim 1 wherein A is:

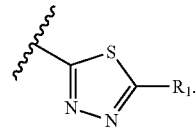

23. The pharmaceutical composition of claim 1 wherein A is:

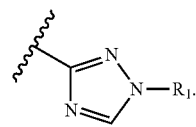

24. The pharmaceutical composition of claim 1 wherein R₁ is optionally substituted aryl.

25. The pharmaceutical composition of claim 24 wherein R₁ is phenyl.

26. The pharmaceutical composition of claim 24 wherein R₁ is substituted phenyl.

27. The pharmaceutical composition of claim 26 wherein R₁ is trifluoromethylphenyl.

28. The pharmaceutical composition of claim 1, further comprising one or more additional biologically active agents.

29. The pharmaceutical composition of claim 28, wherein the additional biologically active agent is selected from vitamin D₂, vitamin D₃, active vitamin D and active vitamin D analogs.

30. The pharmaceutical composition of claim 28, wherein the additional biologically active agent is a phosphate binder, and the compound does not interfere with the phosphate binder.

31. The pharmaceutical composition of claim 30, wherein the phosphate binder is selected from the group consisting of sevelamer carbonate, sevelamer hydrochloride, lanthanum carbonate, calcium carbonate, calcium acetate, MCI-196, ferric citrate, iron magnesium hydroxy carbonate, APS1585, SBR-759 and PA-21.

32. The pharmaceutical composition of claim 1, wherein the compound is substantially active as an inhibitor of Na/phosphate co-transport and the Na/phosphate co-transport is mediated by NaPi2b.

33. The pharmaceutical composition of claim 1 wherein the compound is present in the composition in an amount from 0.2 mg to 2 g per daily dosage.

34. The pharmaceutical composition of claim 33 wherein the compound is present in an amount from 10 mg to 250 mg per daily dosage.

35. The pharmaceutical composition of claim 1 wherein the pharmaceutical composition is a powder, granule, pill, tablet, capsule, liquid, syrup, suspension, emulsion, or aqueous injection solution.

* * * * *